US007981603B2

(12) United States Patent
Feinberg

(10) Patent No.: US 7,981,603 B2
(45) Date of Patent: **\*Jul. 19, 2011**

(54) METHODS FOR IDENTIFYING CANCER RISK

(75) Inventor: Andrew P. Feinberg, Lutherville, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 1397 days.

This patent is subject to a terminal disclaimer.

(21) Appl. No.: 10/629,318

(22) Filed: Jul. 28, 2003

(65) Prior Publication Data

US 2004/0219559 A1    Nov. 4, 2004

Related U.S. Application Data

(63) Continuation-in-part of application No. 10/336,552, filed on Jan. 3, 2003, now Pat. No. 7,611,870.

(60) Provisional application No. 60/398,660, filed on Jul. 26, 2002.

(51) Int. Cl.
*C12Q 1/68* (2006.01)
*C12P 19/34* (2006.01)
*C07H 21/04* (2006.01)

(52) U.S. Cl. ......... 435/6; 435/91.2; 536/23.1; 536/23.5; 536/24.31; 536/24.33; 536/25.32

(58) Field of Classification Search .................. None
See application file for complete search history.

(56) References Cited

U.S. PATENT DOCUMENTS 5,552,277 A   9/1996 Nelson et al.
5,786,146 A   7/1998 Herman et al.
6,235,474 B1  5/2001 Feinberg

OTHER PUBLICATIONS

Ahomadegbe, J.C. et al. Loss of imprinting of H19 and IGF2 genes associated with hypomethylation in invasive breast cancers. Proceedings of the American Association for Cancer Research 37:598 (Mar. 1996).*
Moore, T.F. GenBank Accession No. Y13633 (Dec. 1997).*
Ishihara, K. et al. GenBank Accession No. AF087017 (Oct. 1998).*
Ito, Yet al. Human Molecular Genetics 17(17):2633-2643 (Jun. 2008).*
Jirtle, R.L. Gastroenterology 126(4):1190-1193 (Apr. 2004).*
Jinno, Y. et al. Human Molecular Genetics 5(8):1155-1161 (1996).*
Cui, et al., "Loss of Imprinting in Normal Tissue of Colorectal Cancer Patients with Microsatellite Instabililty", *Nature Medicine*, 4(11):1276-1280 (Nov. 1998).
Cui, et al., "Loss of Imprinting in Colorectal Cancer Linked to Hypomethylation of H19 and IGF2," *Cancer Research*, 62(22):6442-6446 (Nov. 2002).
Nakagawa, et al., "Loss of Imprinting of the Insulin-Like Growth Factor II Gene Occurs by Biallelic Methylation in a Core Region of H19 Associated CTCF-Binding Sites in Colorectal Cancer", *Proceedings of the National Academy Sciences USA*, 98(2):591-596 (Jan. 2001).
Bell, A. C. and Felsenfeld, G., "Methylation of a CTCF—dependent Boundary Controls Imprinted Expression of the Igf2 Gene," *Nature*, vol. 405, pp. 482-485, 2000.
Douc-Rasy, S. et al., "High Incidence of Loss of Heterozygosity and Abnormal Imprinting of H19 and IGF2 Genes in Invasive Cervical Carcinomas. Uncoupling of H19 and IGF2 Expression and Biallelic Hypomethylation of H19," *Oncogene*, vol. 12, pp. 423-430, 1996.
Kaffer, C. R. et al., "A Transcriptional Insulator at the Imprinted H19/Igf2 Locus," *Genes and Development*, vol. 14, pp. 1908-1919, 2000.
Reinhart, B. et al., "Shared Role for Differentially Methylated Domains of Imprinted Genes," *Molecular and Cellular Biol.*, vol. 22, No. 7, pp. 2089-2098, 2002.
Ravenel, J.D., et al., *J. Natl. Cancer Inst.* vol. 93, 2001, pp. 1698-1703.
Rainer et al., *Nature*, vol. 362, 1993, pp. 747-749.
Feinberg, A.P. and Vogelstein, B., "Hypomethylation Distinguishes Genes of Some Human Cancers From Their Normal Counterparts," *Nature* (Lond.), vol. 301, 1983, pp. 89-92.
Feinberg, A.P., et al. "Reduced Genomic 5-Methylcytosine Content in Human Colonic Neoplasia," *Cancer Res.*, vol. 48, 1988, pp. 1159-1161.
Ogawa, O., et al., "Relaxation of Insulin-Like Growth Factor II Gene Imprinting Implicated in Wilm's Tumour," *Nature* (Lond.), vol. 362, 1993, pp. 749-751.
Steelman, M. J., et al., Loss of Imprinting of IGF2 is Linked to Reduced Expression and Abnormal Methylation of H19 in Wilms' Tumour, *Nat. Genet*, vol. 7, 1994, pp. 433-439.
Uegima, H., et al., "Hot-Stop PCR: a Simple and General Assay for Linear Quantitation of Allele Ratios," *Nat. Genet.*, vol. 25, 2000, pp. 375-376.
Sullivan, M.J., et al., "Relaxation of IGF2 Imprinting in Wilms Tumours Associated with Specific Changes in IGF2 Methylation," *Oncogene*, vol. 18, 1999, pp. 7527-7534.
Moore, T, et al., Multiple Imprinted Sense and Antisense Transcripts, Differential Methylation and Tandem Repeats in a Putative Imprinting Control Region Upstream of Mouse $IGF^2$, *Proc. Natl. Acad. Sci. USA*, vol. 94, Nov., 1997, pp. 12509-12514.
Issa, Jean-Pierre J., et al., "Switch from Monoallelic to Biallelic Human $IGF^2$ Promoter Methylation During Aging and Carcinogenesis." *Proc. Natl. Acad. Sci. USA*, vol. 93, Oct. 1996, pp. 11757-11762.

(Continued)

*Primary Examiner* — Diana Johannsen
(74) *Attorney, Agent, or Firm* — DLA Piper LLP (US)

(57) ABSTRACT

The present invention provides methods and kits for identifying an increased risk of developing cancer in a subject. The methods include analyzing a first biological sample, such as a blood sample, from the subject for loss of imprinting of the IGF2 gene. According to the methods a loss of imprinting is indicative of an increased risk of developing cancer. The method can include analyzing genomic DNA from the sample for altered methylation of the IGF2 or the H19 gene. The altered methylation for example includes hypomethylation of a differentially methylated region of IGF2, corresponding to SEQ ID NO:1 and/or a polymorphism or fragment thereof, or hypomethylation of a differentially methylated region of H19 corresponding to SEQ ID NO:6, or a polymorphism, or fragment thereof. In certain aspects, hypomethylation of the H19 DMR or the IGF2 DMR indicates an increased risk of developing colorectal cancer.

12 Claims, 9 Drawing Sheets

OTHER PUBLICATIONS

Nakagawa, H., et al., "Loss of Imprinting of the Insulin-Like Growth Factor II Gene Occurs by Biallelic Methylation in a Core Region of *H19*-Associated CTCF-binding Sites in Colorectal Cancer," *Proc. Natl. Acad. Sci. USA*, Jan. 16, 2001, vol: 98, No. 2, pp. 591-596.

Lee, M.P., et al., "Loss of Imprinting of a Paternally Expressed Transcript, with Antisense Orientation to K,LQT1, Occurs Frequently in Beckwith-Wiedemann Syndrome and is Independent of Insulin-Like Growth Factor II Imprinting," *Proc. Natl. Acad. Sci. USA.*, vol. 96, Apr. 1999, pp. 5203-5208.

Cui, Hengmi, et al., "Loss of Imprinting of *Insulin-like Growth Factor-II* in Wilms' Tumor Commonly Involves Altered Methylation but not Mutations of *CTCF* or Its Binding Site[1]," *Cancer Research*, vol. 61, Jul. 1, 2001, pp. 4947-4950.

Takai, Daiya, et al., "Large Scale Mapping of Methylcytosines in CTCF-binding Sites in the Human *H19* Promoter and Aberrant Hypomethylation in Human Bladder Cancer," *Human Molecular Genetics*, vol. 10, No. 23, 2001, pp. 2619-2626.

Bartolomei, M.S., et al., "Epigenetic Mechanisms Underlying the Imprinting of the Mouse H19 Gene," *Genes & Dev.* 7(9), Sep. 1993, pp. 1663-1673.

Taniguchi, T., et al., "Epigenetic Changes Encompassing the *IGF2/H19* Locus Associated with Relaxation of *IGF2* Imprinting and Silencing of *H19* in Wilms Tumor," *Proc. Natl. Acad. Sci.*, vol. 92, Mar. 1995, pp. 2159-2163.

Catchpoole, D., et al., "Mutation Analysis of *H19* and *NAP1L4* (*hNAP2*) Candidate Gene and *IGF2* DMR2 in Beckwith-Wiedemann Syndrome," *J. Med Genet*, 37(3) Mar. 2000, pp. 212-215.

Nishihara, S., et al., "Multipoint Imprinting Analysis in Sporadic Colorectal Cancers With and Without Microsatellite Instability," *Int. J. Oncol.*, 17(2), Aug. 2000, pp. 317-322.

Hofmann, W.K., et al., "Loss of Genomic Imprinting of Insulin-Like Growth Factor 2 is Strongly Associated with Cellular Proliferation in Normal Hematopietic Cells," *Exp. Hematol*, 30(4), Apr. 2002, pp. 318-323.

Cui, H., et al., "Loss of Imprinting in Colorectal Cancer Linked to Hypomethylation of *H19* and *IGF2*[1]," *Cancer Research*, 62, Nov. 15, 2002, pp. 6442-6446.

Vu, T.H., et al., Symmetric and Asymmetric DNA Methylation in the Human IGF2-H19 Imprinted Region, *Genomics*, 64(2) Mar. 1, 2000, pp. 132-143.

Schoenherr, C.J., et al., "CTCF Maintains Differential Methylation at the *Igf2/H19* Locus," *Nat. Genet*, 33(1), Jan. 2003, pp. 66-69.

Bell, A.C., et al., "The Protein CTCF is Required for the Enhancer Blocking Activity of Vertebrate Insulators," *Cell*, vol. 98, Aug. 6, 1999, pp. 387-396.

Schneider, D.T., et al., "Multipoint Imprinting Analysis Indicates a Common Precursor Cell for Gonadal and Nongonadal Pediatric Germ Cell Tumors[1]," *Cancer Research*, vol. 61, Oct. 1, 2001, pp. 7268-7276.

Uyeno, S., et al., "*IGF2* But not *H19* Shows Loss of Imprinting in Human Glioma[1]," *Cancer Research*, vol. 56, Dec. 1, 1996. pp. 5356-5359.

Yun, K., et al., "Analysis of *IGF2* Gene Imprinting in Breast and Colorectal Cancer by Allele Specific-PCR," *Journal of Pathology*, vol. 187, 1999, pp. 518-522.

\* cited by examiner

TCTGTTGCACCCTGGACCCAGACTCCTCAATCCACCCAGGGTGGTGTCTGTGG
GGAGGGGGTTCACTTCCCCAGGAAGCACAGCCACGCCGTCCCTCACTGGCCT
CGTCAAGCAGAGCTGTGTGTCCAGTGGCTTTTGCTGGGGCCCCCTCCTTATCT
CCTTCCAAGGTGGGGGTGTTTGGAGGTGGAGGAGGCTTTCATATTCCGTGCC
ATGACCCCTCAAGGCGGGCCATTCGTGTGCACCCTCCACCCCCAGT

FIG. 1

```
GCAACAGTGATGTAATCCTAGGAGCAATTTGAGGAGGTTAAAAATCTTTC
AGCCTCCAGATGTGTGACTCCATGACTCCTAAACCATAATTTCTAATCTGT
GGCTAATTTGTTAGTCCTGAAAGTCTAGTCCCCAGGCAGGAAGAGGGTCT
GTCCTGGGAAGGGCTGTTATTGTCTTTGTTTCAAAGATAAACTATAAACT
AAGTTCTTCCCAAAGTTAGTCCAGCCTGCACCCAGAAATGAATAAGAAGG
CAAGACAGAGTTGGTTACGTCAGATCTCTTTCATTGTCATAATTTTCTGTT
ATATATTTTTTTTTTTGAGACAGAGTTTCGCTCTTATCATCCAGGCTGGA
GTCCAATGGCTCGATCTTGGCTCACTGCAACCTCCACCTCCGGAGTTCAG
TGATTCTCCTGCCTCAGCCTCCCAAGTAGCTGGGATTACAGGCGCCCACCA
CCATGCCCAGCTAATTTTTGTATTTTTAGTAGAGATGGGATTTCGTCAGGT
TGGCCAGGTTGGTCTTGAACTCCTGACCTCAGGTGATCCACCCACCTCGGC
CTCCCAAACTGCTGGGATTACAGGCATGAGCCACCATCGCCGGCCGATTT
TCTGTAATAATTTTTGCAGAGGCGGTTTCACCAGGAGAACCAAGCATTAA
TGCGCTGTGGCTGATGTGTAGTAGAGCGGCATTTCCCAATGGGAGAACCC
TGGGGCTGTCTAGGAGCCCATGCATGGCTGGGAGCCTAATCCCAGGGACA
CCACCGATGACAGCTCCCATAGCACGTAGGACAGTGGATACTTGGAGGCA
AAGAGAAATCTCTGTTCTGCAGTGGTCATGACTTGGACCCCAAAGAACTT
GAGCCCAAGGTCCAGAGGGAGACCCTCCCAACAAGGCCTCCAGCAGGAA
CAGGGATCGTGGGAGCCTGCCAAGCACAGCGCACAGGTATTTCTGGAGGC
TTCCCATTCAGTCTTGGATGCCAGCCTCACCAAGGGCGGCCCATCTTGCTG
ACCTCACCAAGGGAGGCCCGTCTCACTGCCCTGATGGCGCAGAATCGGCT
GTACGTGTGGAATCAGAAGTGGCCGCGCGGCGGCAGTGCAGGCTCACACA
TCACAGCCCGAGCACGCCTGGCTGGGGTTCACCCACAGAAACGTCCCAGG
TCTCCCAGGCCAGGTGCCGCATTGGTTCCCGAGGGTTGTCAGAGATAGAC
ACTCATGCGACTAACATCGGGCTATGTGTTTGATTCACCCCAGGGTGCATT
GTTGAAGGTTGGGGAGATTGGAGGAGATGCTTGGGGGACAATGAGGTGTC
CCAGTTCCTTGGATGATAGGGATCTCGGCCTAAGCGTGAGACCCCTCCTAC
AGGGTCTCTGGCAGGCACAGAGCCTGGGGGCTCTTGCATAGCACATGTGT
ATTTCTGGAGGCTTCCCCTTCGGTCTCACCGCCCCGATGGTGCAGAATCGG
TTGTAGTTGTGGAATCGGAAGTGGCCGCGCGGCGGCAGTGCAGGCTCCCA
CATCACAGCTCAAGCCCGCCCAGCTGAGGTTCACCCGCGGAAACGTCCC
GGGTCACGCAAGCTAGGTGCCGCAAGGTTCACGGGGGTAGTGAGGGATA
GAACACTCATGGGAGCCACATTGGGCTACGTGTCTGATTCACCCCAGGGT
GCACTATTGAGGGTTGGGGAGATGAGATACTTTGGTGACAATGAGGTGTC
CCCATTCTTTGGATGATGGGGATCTCGGCCTCAGCGTGAGGCCCCTCCCAC
AGGGTCTCTGGCAGGCACAGAAACTGGGGGCTCTTGCGTAGCACATGGGT
ATTTGTGGACGCTTCCCCTTCTGTCTCACCACCCGGATGGCACAGAATCGG
TTGTAAGTGTGGACTCAAAAGTGGCCGCGCGGCGGCAGTGCAGGCTCACA
CATCACAGCCCAAGCCCTCCTGGATGGGGTTCGCCCGCGGAAACGTCCT
GGGTCACCCAAGCCAGGTGCCGCAGGGTTCTCGGAGGTCTTCTGGGAATA
GGACGCTCATGGGAGCCACACCACGTCTTCGTATCGGGCCATATCCACGG
CCGCGTGGCCCCAGGTCACACTCTGAGGGCTTCAGTGTCATGGCCTGGGA
CTCAAGTCACGCCTACCCGCGTGATGAGCACAGCAAATTCCAACAAAAGC
TTATACTTTCCACATCCATCCCAGAGCACAGATCCGACTAAGGACAGCCC
```

FIG. 3-1

```
CCAAATCCCGAGCCTTTTTCTGAACTGACAATTGCCTCCCCAGTGAACACT
CTGAGCTTGTCAATCTTAAGTGGCCAGACATTAACATTCCCATTCAGTGCA
GGTTTGAGATGCTAATTTAGGAGCTTGAGATGCTAAAGAGCTGGGAGTGC
CACTGCTGCTTTATTCTGGGGTCTAGGATCCTTGTGTTGGCTGAGATAATC
TGCTAATGTGGGTGCAGCAGACATCCCGCGGTTTGTGGAATCGATAAAGG
ATGGGGATCAATGGTGTTTGTGCACTGTGCGGTCTGTGCCCAATTGCCTGC
CTTGTGCTGTGGAATCTGTACACCTGGCCAACATGTGCTTGTGTGAGCCTG
ACAGTGCATTTCCAGAGCCTCACCTCGGCTCTGCCCTGGAGGCTCTGTGC
TGCTGGAATCAGACTCAAGGACCTCATCAGAGGACCATGGCCCCGTATCA
CCTGGGTCAGGCACTGAAGCTGGGACAGGAGAGCAGAGACTTCCAAAAT
GAGGGATCCCTGTGTTCTGAGGTGATCATGACTGGGACCCAAGGACTCAA
GCGCATGCTCCAGAGGGAATCGTTTCCCACAAGGCCTTTGGCAGGAACAG
GGATCCTGGGAGCCTGCCAAGCAGAGCGCACAGTGTTCCTGGAGTCTCGC
TGCCCAGATGCCACGGAATCAGTTGAAGGTATGGAAACACAGGTGGCCAC
GTGGTAGCAGGGCAGGCTCAGGCGTCATAGCCCGAGCCCGGCTACCTGTG
GTTTGCCTGCAGAAACATCCCGGGTCAACAGGCCAGGCACCGCATTGGTT
CGCGAGGGTCATCGGGGGTAGGACCCTTGTACGAGCCACATCGGGCTACG
TGCCTGATTCACCCCAGGGTGCACTGTTGAAGGTTGGGGAGATGAGAGGA
GATACTTGGGGGACAGTGAAGTGTCCCCATTCTTTGGATGATGGGGATCT
CGGCCTCAGCGTGAGACCCCTCCCACAGGGTCTCTGGCAGGCTCAAGAGC
CCAGGGGCTCTTGCATAGCACATGAATATTTCTGGAGGCTTCCCCTTCAGT
CTCACCACCCGGATGGTGCAGAATTGGTTGTAGCTGTGGAATCGGAAGTG
GCCGCGTGGCGGCAGTGCAGGCTCACACATCACAGCCCGAGCCCACCCCA
GCTGGGGTTCGCCCGCGGAAACGTCCCGGGTCCCGCAAGCCAGGCGCCGC
AGGGTTCACGGGGGTCATCAGGGATAGGACATTCATGGGAGCCACATCGG
GCTATGTGTCTGATTCACCCCAGGGTGCACTATTGAGGGTTGGGAAGATG
AGAGGAGATGCTTGGGGGACAATGAAGTGTCCCCATTCTTTGGATGATGG
GGATCTTGGCCTCAGGGTGAGATCCTTCTTGCAGGGTCTATGGCAGGCAC
AGAGCCCGGGGGCTCTTGCATAGCACATGTGTATTTCTGGAGGCTTCCCCT
TCAGTCTCACCGCCCGGATGGCACGGAATTGGTTGTAGTTGTGGAATCGG
AGGTGGCTGCGCGGCGGCAGTGCAGGCTCACACATCACAGCCCGAGCCCG
CCCCAGCTGGGGTTCGCCCGTGGAAACATCCCAGGTCATCCAAGCCGGGC
GCCACAGGGTTCACAGGGGTCGTGAGGTATAGGACACTCATGGGAGCCAT
ATCGGGCTACGTGTCTGATTCACCCCAGGGTGCACTGTTGAAGGTTGGGG
AGATGGGAGGAGATACTAGGGGAACAATGAGGTGTCCCAGTTCCATGGAT
GATGGGGATCTCGGCCCTAGTGTGAAACCCTTCTCGCAGGGTCTCTGGCA
GGCACAGAGCCCGGGGGCTCTTGCATAGCACATGGGTATTCTGGAGGCT
TCTCCTTCGGTCTCACCGCCTGGATGGCACGGAATTGGTTGTAGTTGTGGA
ATCGGAAGTGGCCGCGCGGCGGCAGTGCAGGCTCACACATCACAGCCCGA
GCCCGCCCCAACTGGGGTTCGCCCGTGGAAACGTCCCGGGTCACCCAAGC
CACGCGTCGCAGGGTTCACGGGGGTCATCTGGGAATAGGACACTCATAGG
AGCCGCACCAGATCTTCAGGTCGGGCATTATCCACAGCCCCGTGGCCCCG
GGTCACACTCCGAGGGCTTCAGTGTCATGGCCTGGGACTCAAGTCACGCC
TACTTATGTGATGATCACAGTGTGTTCCACCAAAATCTTACATTTTCCACA
```

FIG. 3-2

```
TCTATCCCAGAGCACAGCTCCGACTCCGTCTAAGGACAGCCCCCAAATCC
CCAGCCTTTTACTGAACTGACAATTGCCTCCCCAGTGAACACTCTGATCTC
CTCAGCCCTAAGTGGCCAGACATTAACATTCTCATTCAATGCAGGTTTGAG
GTGCTAATTCAGGAGCTTAAGATGCTAAAGAGCTGGGAGCGCCACTGCTG
CTTTATTCTCTGGTCCAGGATCCTTGTGTTGCTGGAGATAATCCATTATCGT
GGGTGCAGCAGACACCCTGCGGCTTGTGGACTCGGTACGGGGTGGGGATC
CTGATGGGGTTAGGATGTTCGATGGCTCGGGTGTGCTCCACGCTCAGGGA
TCATCACGTCCGGCCGGCGGTAGTTGGCACGTGGAGAGGTGAATTTGCCC
ACAGGTGTTCCCCGTGCCTGCGCATTGCTGGCAGCACGACCGGATCCTGT
GCTAGCCCCTCCCACAATGCCTGGAGCAGGAGCGAGGGGCCTGGGGAGCC
GCCTTGCCTGGAGCATTTGTATTTCCGGAGTATTTCCTGAGTCTCCCCTTG
GGTCTTGGGTGCTGTCCCCAGTGAGCCCATCTCCCAGCGATGGCACAGAA
TCGGTTGTGGCTGTGGAGACGGAAATGGCCGAGAGGCGGCAGTGGTGACT
CACATCACAGTCTGAAGGTGACCCAAGGCTGGACTCCACTTTTAGCAAAA
TGTGGGGGTCTGCCTTGGTCTCCTAACTTGGGGGTCCACTCATGGAAAAGC
CTGAGAATTTTCATGCCATGGAAATTCCCCCATGTCGTGGGGTTCACGCAC
GACAAAGCCCGGCGGTCAGTGCTCAGCAGGCAAGCACTCAGCCCTTTCCG
GTGGGGCCATGGGAACAGAGGGTTTGCCGAAGGCGCGGCCAGCCCTTCCA
CATCCCAGAGGGCCTGCTGCGTGATTGGACCCGTGAACTCTGGGTCCCTTG
GCCCTGGTGCTCCCCTTCACGGCTTTGACACTCGAGACTTGAGGTGAACCC
CAGGGACTGCAGGGCCCCAACAACCCTCACCAAAGGCCAAGGTGGTGAC
CGACGGACCCACAGCGGGGTGGCTGGGGGAGTCGAAACTCGCCAGTCTCC
ACTCCACTCCCAACCGTGGTGCCCCACGCGGGCCTGGGAGAGTCTGTGAG
GCCGCCCACCGCTTGTCAGTAGAGTGCGCCCGCGAGCCGTAAGCACAGCC
CGGCAACATGCGGTCTTCAGACAGGAAAGTGGCCGCGAATGGGACCGGG
GTGCCCAGCGGCTGTGGGGACTCTGTCCTGCGGAAACCGCGGTGACGAGC
ACAAGCTCGGTCAACTGGATGGGAATCGGCCTGGGGGGCTGGCACCGCGC
CCACCAGGGGGTTTGCGGCACTTCCCTCTGCCCCTCAGCACCCCACCCCTA
CTCTCCAGGAACGTGAGTTCTGAGCCGTGATGGTGGCAGGAAGGGGCCCT
CTGTGCCATCCGAGTCCCCAGGGACCCGCAGCTGGCCCCAGCCATGTGC
AAAGTATGTGCAGGGCGCTGGCAGGCAGGGAGCAGCAGGCATGGTGTCC
CCTGAGGGGAGACAGTGGTCTGGGAGGGAGAAGTC
```

FIG. 3-3

METHODS FOR IDENTIFYING CANCER RISK

RELATED APPLICATION DATA

This application claims the benefit of priority under 35 U.S.C. §119(e) of U.S. Ser. No. 60/398,660, filed Jul. 26, 2002, the entire contents of which is incorporated herein by reference. This application is a continuation-in-part application of U.S. Ser. No. 10/336,552, filed on Jan. 3, 2003, now U.S. Pat. No. 7,611,870.

STATEMENT OF GOVERNMENT SUPPORT

This invention was made in part with government support under Grant No. R01 CA65145 and K07 CA092445 awarded by the National Institutes of Health. The United States government has certain rights in this invention.

BACKGROUND OF THE INVENTION

1. Field of the Invention

The present invention relates generally to methods for detecting the presence of or risk of developing cancer and more specifically to methods for detecting the presence of hypomethylation of the H19 gene and the IGF2 gene.

2. Background Information

The single greatest impediment to cancer diagnosis is the general requirement that the tumor itself must be detected directly. Efforts to identify genetic abnormalities in normal tissues of patients with cancer or at risk of cancer have been disappointing. For example, BRCA1 mutations are present in only about 1% of breast cancers. A small fraction of patients with colorectal cancer have predisposing mutations in the APC gene (>1%), causing adenomatous polyposis coli. An even smaller fraction show mutations in genes responsible for replication error repair (>2% of colon cancer patients, or much less than 1% of the population), show mutations in genes responsible for nucleotide mismatch error repair causing hereditary nonpolyposis colorectal cancer (HNPCC or Lynch syndrome).

Diagnostic methods such as microsatellite instability, require for identification that a patient already have a tumor. For example, microsatellite instability compares microsatellite marker length between the monoclonal tumor cell population and normal tissue derived from the same patient.

Family history still remains the most reliable diagnostic procedure for identifying patients at risk of cancer. A molecular diagnostic approach that might identify patients with cancer or at risk of cancer, using only normal tissue, would offer a decisive advantage for intervention and treatment.

Except for rare hereditary cancer syndromes, the impact of molecular genetics on cancer risk assessment and prevention has been minimal. Cancer surveillance has been effective for some cancers in which risk can be identified, for example colorectal cancer in familial adenomatous polyposis coli and hereditary nonpolyposis colorectal cancer (Markey, L., et al., *Curr. Gastroenterol. Rep.* 4, 404-413 (2002)), but these syndromes cumulatively account for less than 1% of cancer patients (Samowitz, W. S., et al., *Gastroenterology* 121, 830-838 (2001); Percesepe, A., et al., *J. Clin. Oncol.* 19, 3944-3950 (2001)). Nevertheless, genetics is thought to contribute substantially to cancer risk, since the odds ratio for malignancy increases in patients with first degree relatives with cancer, e.g., 2 to 3-fold in colorectal cancer (Fuchs, C. S., et al., *N. Engl. J. Med.* 331, 1669-1674 (1994)). Therefore, there remains a need to develop genetic tests to identify these patients.

Accordingly, no tests are available for identifying common cancer risk in the general population. As discussed above, genetic abnormalities that are known to predispose to cancer are rare. At the same time, advances in cancer treatment have had a small impact on morbidity and mortality. A major advance in cancer requires identification of patients at risk (i.e. identifies patients before they develop cancer), which could be combined with increased surveillance and chemoprevention, similar to the modern approach to cardiovascular medicine.

Thus, there remains a need for a diagnostic method for detecting and/or screening for the presence of diseases and/or the risk of developing a disease. In particular, there remains a need for a method for detecting and/or screening for the presence of cancer, for example colorectal cancer. There also remains a need for a method of detecting and/or screening for the presence of cancer and/or the risk of developing cancer that can be applied to a wide section of the population.

Epigenetic alterations in human cancer, i.e., alterations in the genome other than the DNA sequence itself, were first described in 1983 by Feinberg and Vogelstein (A. P. Feinberg et al., *Nature* (Lond.), 301: 89-92, 1983), who found widespread hypomethylation of genes in CRCs and in premalignant adenomas. Epigenetic abnormalities identified subsequently include global genomic hypomethylation (A. P. Feinberg et al., *Cancer Res.*, 48: 1159-1161, 1988), promoter hypermethylation of CpG islands (S. B. Baylin, et al., *Cancer Res.*, 46: 2917-2922, 1986; A. Merlo et al, *Nat. Med.*, 1: 686-692, 1995), and LOI (Rainier S. Johnson et al, *Nature* (Lond.), 362: 747-749, 1993; O. Ogawa et al., *Nature* (Lond.), 362: 749-751, 1993), or loss of the normal parent of origin-dependent gene silencing, affecting at least the genes IGF2, PEG1, p73, and LIT1 (S. Rainier et al., *Nature* (Lond.), 362: 747-749, 1993; O. Ogawa et al., *Nature* (Lond.), 362: 749-751, 1993; I. S. Pedersen et al, *Cancer Res.*, 59: 5449-5451, 1999; M. P. Lee et al, *Proc. Natl. Acad. Sci.* USA, 96: 5203-5208, 1999; M. Kohda et al, *Mol. Carcinog.*, 31: 184-191, 2001; Y. C., Cai et al., *Carcinogenesis* (Lond.), 21: 683-689, 2000; K. Tanaka et al, *Oncology*, 60: 268-273, 2001). LOI of IGF2 causes overexpression of IGF2 (J. D. Ravenel et al, *J. Natl. Cancer Inst.*, 93: 1698-1703, 2001), an important autocrine growth factor in cancer. LOI was first identified in embryonal tumors in childhood, including Wilms' tumor, in which it is the most common molecular alteration (S. Rainier et al, *Nature* (Lond.), 362: 747-749, 1993; O. Ogawa et al, *Nature* (Lond.), 362: 749-751, 1993), as well as rhabdomyosarcoma (S. Zhan et al, *J. Clin. Investig.*, 94: 445-448, 1994) and hepatoblastoma (S. Rainier et al, *Cancer Res.*, 55: 1836-1838, 1995). LOI was also later found in common adult malignancies including ovarian (H. T. Kim et al, *Am. J. Med. Genet.*, 80: 391-395, 1998), colon (H. Cui et al, *Nat. Med.*, 4: 1276-280, 1998), lung (M. Kondo et al, *Oncogene*, 10: 1193-1198, 1995), and bladder cancer (M. Elkin et al, *FEBS Lett.*, 374: 57-61, 1995), as well as chronic myelogenous leukemia (G. S. Randhawa et al, *Blood*, 91: 3144-3147, 1998). In CRC, LOI is particularly important because it is found commonly in both the tumor and normal tissue of patients with CRC, at ~3-fold higher frequency then in patients without colon tumors (H. Cui et al, *Nat. Med.*, 4: 1276-280, 1998), and, thus, LOI may represent the only common alteration linked to cancer that is found in normal tissue.

In Wilms' tumors, approximately half of tumors appear to arise by an epigenetic mechanism involving LOI rather than genetic alterations involving, for example, WT1 mutations and LOH, and the tumors with LOI appear in children who develop cancer at a later age, accounting for the bimodal age distribution of Wilms' tumor (J. D. Ravenel et al, *J. Natl. Cancer Inst.*, 93: 1698-1703, 2001). LOI was linked to increased methylation, because Wilms' tumors with LOI of IGF2, i.e., activation of the normally silent maternal allele, show aberrant methylation of the normally unmethylated maternal allele of a DMR upstream of the H19 gene on the same chromosome (M. J. Steenman et al, *Nat. Genet.*, 7: 433-439, 1994; T. Moulton et al, *Nat. Genet.*, 7: 440-447, 1994). This result is consistent with the enhancer competition model for regulation of H19 imprinting. By this model, IGF2 and H19 promoters compete on the same chromosome for a shared enhancer, and access of the maternal IGF2 allele to this enhancer is blocked by the H19 DMR when unmethylated, likely because of the insulator activity of CTCF binding to the unmethylated H19 DMR (P. A. Leighton et al, *Nature* (Lond.), 375: 34-39, 1995; R. Ohlsson et al, *Trends Genet.*, 17: 520-527, 2001; W. Reik et al, *Nature* (Lond.), 405: 408-409, 2000; A. T. Hark et al, *Nature* (Lond.), 405: 486-489, 2000; A. C. Bell et al, *Nature* (Lond.), 405: 482-485, 2000). Consistent with this, it has been observed that in Wilms' tumor, methylation of the maternal H19 DMR includes CTCF-binding sites (H. Cui et al, *Cancer Res.*, 61: 4947-4950, 2001). These results would suggest that increased or ectopic activity of a DNA methyltransferase might lead to aberrant methylation of the maternal H19 DMR.

Therefore, it was surprising to observe that HCT116, a CRC line with normal imprinting of IGF2, is hypermethylated at H19 and retains normal imprinting after somatic cell knockout of the maintenance DNA methyltransferase DNMT1 but loses imprinting after subsequent somatic cell knockout of DNMT3B (*Nature* (Lond.), 416: 552-556, 2002), a de novo methyltransferase, i.e., that is able to methylate unmethylated sequences and is necessary for normal imprinting (M. Okano et al, *Cell*, 99: 247-257, 1999; K. Hata et al, *Development* (Camb.), 129:1983-1993, 2002). Therefore, there remains a need to determine the relationship between methylation state of IGF2 and H19 and loss of imprinting and/or cancer risk, such as colorectal cancer risk, and to devise methods for identifying cancer risk based on this relationship The results described herein differ from past studies, and suggest a model of IGF2 imprinting in at least the colon that differs from the conventional view of enhancer competition between IGF2 and H19.

SUMMARY OF THE INVENTION

The present invention provides methods and kits that are based on the finding of an association between loss of imprinting (LOI) and family history of colorectal cancer (CRC) and between LOI and present or past personal history of colorectal neoplasia. Furthermore, the present invention provides methods, kits, and nucleic acid primers, that are based on the finding that hypomethylation of both the IGF2 gene and the H19 gene is correlated with loss if imprinting of the IGF2 gene. Loss of imprinting of IGF2 is correlated with the presence and increased risk for developing cancer, especially colorectal cancer.

Accordingly, methods of the present invention analyze LOI, especially LOI of the IGF2 gene, for example by analyzing hypomethylation of the IGF2 gene or H19 gene, to identify an increased risk of developing cancer in a subject.

Accordingly, in one embodiment, the present invention provides a method for identifying loss of imprinting of the IGF2 gene in a subject. The method in this embodiment includes analyzing a biological sample from the subject for hypomethylation of a differentially methylated region (DMR) of the H19 gene and/or the IGF2 gene, or a polymorphism and/or fragment of the H19 DMR and/or IGF2 DMR. Typically, the subject is a human subject. Furthermore, in certain aspects, the H19 DMR or fragment thereof, includes a CTCF binding site, for example, CTCF binding site 1 or CTCF binding site 6.

In certain aspects of this embodiment, the subject is an apparently normal subject. Furthermore, in certain aspects, hypomethylation is analyzed in a DNA region corresponding to SEQ ID NO:6, an H19 DMR. In certain aspects the method comprises analyzing the biological sample for hypomethylation of positions within the region of the H19 DMR that are analyzed using the nested primer pairs SEQ ID NOs:23 and 24, followed by SEQ ID NOs:25 and 26, as illustrated in the Examples herein. Furthermore, in certain aspects, hypomethylation is analyzed in a DNA region corresponding to SEQ ID NO:1, an IGF2 DMR. In certain aspects the method comprises analyzing the biological sample for hypomethylation of positions within the region of the IGF2 DMR that are analyzed using the nested primer pairs SEQ ID NOs:2 and 3, followed by SEQ ID NOs:4 and 5, or the region analyzed using primer pairs SEQ ID NOs: 27 and 28, followed by SEQ ID NOs:29 and 30, as illustrated in the Examples herein.

In another embodiment, the present invention relates to a method for identifying an increased risk of developing cancer in a subject. The method includes analyzing a biological sample from the subject for hypomethylation of a differentially methylated region (DMR) of an H19 gene, or a polymorphism and/or fragment of the H19 DMR. In certain aspects of the invention, the cancer is colorectal cancer. In certain aspects, the method further includes analyzing the biological sample for hypomethylation of a DMR of the IGF2 gene, SEQ ID NO:1, or a polymorphism and/or fragment thereof.

In another embodiment, the present invention provides a method for identifying an increased risk of developing cancer in a subject. The method includes analyzing a biological sample from the subject for loss of imprinting of the IGF2 gene. According to the method a loss of imprinting is indicative of an increased risk of developing cancer. In certain embodiments, the method includes analyzing the genomic DNA for hypomethylation of a differentially methylated region (DMR) of IGF2 and/or a DMR of H19, or a polymorphism and/or fragment of the IGF2 DMR and/or the H19 DMR. The region analyzed in one aspect of the invention corresponds to SEQ ID NO:1 or a polymorphism thereof, or SEQ ID NO:6, or a polymorphism thereof. The method can be performed during routine clinical care, on a subject having no apparent or suspected hyperproliferative disorder such as cancer. The first biological sample can be a blood sample, for example.

In one aspect, the method can further include analysis of a second biological sample from the subject at a target tissue for loss of imprinting of the IGF2 gene, wherein a loss of imprinting in the second sample is indicative of an increased risk of developing cancer in the target tissue. In certain embodiments, the second biological sample is not a blood sample. For example, the first biological sample can be a blood sample and the second biological sample can be isolated from colorectal tissue. In embodiments where the second biological sample is isolated from colorectal tissue, the cancer is typically colorectal cancer.

In another embodiment, the present invention provides a method for managing health of a subject. The method includes performing the method discussed above, and then performing a traditional cancer detection method on the subject if the subject has an increased risk for developing cancer. The traditional cancer detection method can be, for example, colonoscopy, especially where the subject has an increased risk of developing colorectal cancer.

In yet another embodiment, the present invention provides a method for prognosing cancer risk of a subject. The method includes analyzing a first biological sample from the subject for altered methylation of a differentially methylated region (DMR) of the IGF2 gene and/or of the H19 gene, or a polymorphism and/or fragment of the IGF2 DMR and/or the H19 DMR. In certain aspects, the method analyzes SEQ ID NO:1 or SEQ ID NO:6. Hypomethylation is indicative of an increased risk of developing cancer. In this embodiment, the first biological sample is typically a blood sample.

In one embodiment, the present invention provides a method for identifying predisposition to colorectal cancer of a subject. The method includes identifying a loss of imprinting in a biological sample from the subject and correlating the loss with a predisposition to colorectal cancer. Loss of imprinting is associated with an increased predisposition to colorectal cancer.

In another embodiment, the present invention provides a kit for determining a methylation status of a differentially methylated region (DMR) of IGF2 corresponding to SEQ ID NO:1 or a polymorphism or fragment thereof, or of the DMR of H19, corresponding to SEQ ID NO:6, or a polymorphism or fragment thereof. The kit includes an oligonucleotide probe, primer, or primer pair, or combination thereof, capable of binding to the DMR with or without prior bisulfite treatment of the DMR. In certain aspects, the kit includes one or more detectable labels.

The kit, in certain aspects, also includes a plurality of oligonucleotide probes, primers, or primer pairs, or combinations thereof, capable of binding to the DMR of IGF2 or H19 with or without prior bisulfite treatment of the DMR. The kit can include an oligonucleotide primer pair that hybridizes under stringent conditions to all or a portion of the DMR only after bisulfite treatment. The kit can include instructions on using kit components to identify an increased risk of developing cancer. In certain embodiments the instructions are directed at subjects of the general population. The kit for example, includes one or both of a primer pair corresponding to the primer pair SEQ ID NO:23 and SEQ ID NO:24 and the primer pair SEQ ID NO: 25 and SEQ ID NO:26. In another aspect, the kit for example, includes one or both of a primer pair corresponding to the primer pair SEQ ID NO:27 and SEQ ID NO:28, and the primer pair SEQ ID NO: 29 and SEQ ID NO:30.

In another embodiment, the present invention provides isolated oligonucleotides and primer pairs corresponding to SEQ ID NO:23 and SEQ ID NO:24; SEQ ID NO:25 and SEQ ID NO:26; SEQ ID NO:27 and SEQ ID NO:28; and SEQ ID NO:29 and SEQ ID NO:30, and isolated nucleic acids that correspond to a region of the IGF2 or H19 DMRs that is amplified by SEQ ID NO:23 and SEQ ID NO:24; SEQ ID NO:25 and SEQ ID NO:26; SEQ ID NO:27 and SEQ ID NO:28; and SEQ ID NO:29 and SEQ ID NO:30.

BRIEF DESCRIPTION OF THE DRAWINGS

FIG. 1 provides the sequence of a differentially methylated region (DMR) of the IGF2 gene. The sequence corresponds to SEQ ID NO:1. The IGF2 DMR corresponds to residues −566 bp to −311 bp relative to human IGF2 exon 3, which corresponds to positions 661 to 916 of GenBank accession no. Y13633.

FIG. 3 provides the sequence of a differentially methylated region (DMR) of the H19 gene. The sequence corresponds to SEQ ID NO:6 The H19 DMR corresponds to nucleotides 2057 to 8070 of Genbank accession no. AF087017 (SEQ ID NO:37).

DETAILED DESCRIPTION OF THE INVENTION

Figure 2A:
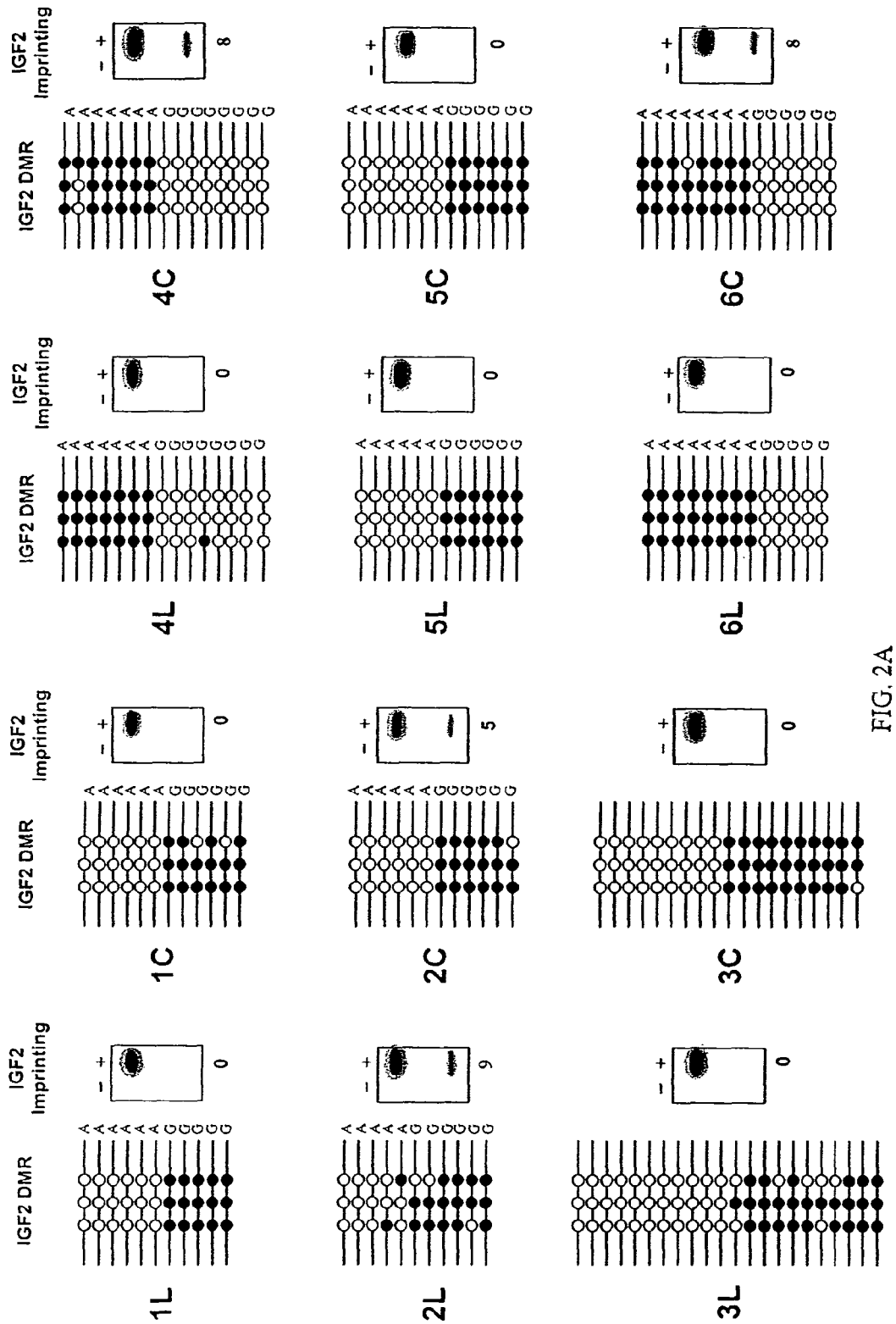
FIGS. 2A and 2B show methylation status and imprinting analysis of the IGF2 DMR of SEQ ID NO:1, in PBL and normal colonic mucosa with either normal imprinting or LOI of IGF2. (A) IGF2 DMR shows normal methylation in PBL and normal colonic mucosa with normal imprinting of IGF2. Shown are the methylation states of individual PCR products subcloned after bisulfite treatment and PCR. In some cases, individual alleles can be distinguished by single nucleotide polymorphisms on the same PCR product (shown at right). Ten to 20 clones were sequenced depending on heterozygosity at the SNP site. Filled circles represent methylated cytosine and open circles represent unmethylated cytosine. Imprinting analysis was performed by hot-stop PCR (Uejima, H., et al., Nat. Genet. 25, 375-376 (2000)), and is shown without (−) and with (+) reverse transcriptase. LOI index is displayed numerically (LOI index=(less active allele/more active allele)×100%). LOI is defined as an LOI index>25 (Cui, H., et al., Nat. Med. 4, 1276-1280 (1998)). Patient samples are matched PBL (Patient number includes "L") and colon from the same individuals (Patent number includes "C"). Single nucleotide polymorphisms distinguishing alleles are shown on the left. (B) IGF2 DMR shows biallelic hypomethylation in PBL and normal colonic mucosa with LOI of IGF2, except for one sample that displays partial methylation of both alleles.
Figure 2B:
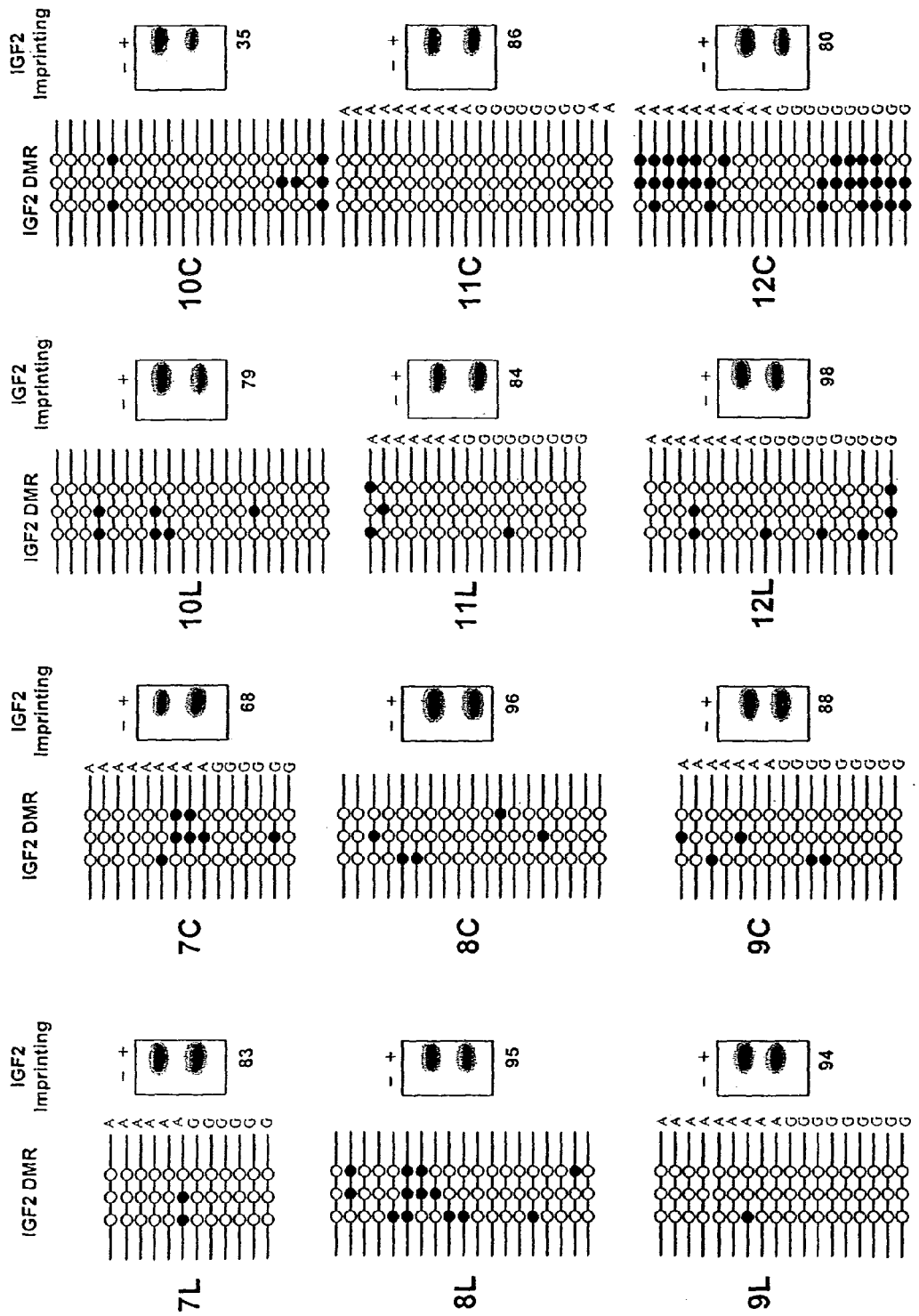

Epigenetic alterations in human cancers include global DNA hypomethylation, gene hypomethylation and promoter hypermethylation, and loss of imprinting (LOI) of the insulin-like growth factor-II gene (IGF2). A mechanism for LOI described previously is hypermethylation of a differentially methylated region (DMR) upstream of the H19 gene, allowing activation of the normally silent maternal allele of IGF2. The present specification discloses that this mechanism does not apply to colorectal cancers, which show hypomethylation of the H19 DMR as well as the DMR upstream of exon 3 of IGF2. This hypomethylation is found in both colorectal cancers and normal mucosa from the same patients, and in cell lines with somatic cell knockout of DNA methyltransferases DNMT1 and DNMT3B. These data suggest that hypomethylation is a mechanism for LOI, that the popular IGF2-H19 enhancer competition model for IGF2 imprinting does not apply to the human colon, and that an alternative model for LOI would involve a transcriptional repressor acting on the normally silent maternal allele of IGF2.

Accordingly, in one embodiment, the present invention provides a method for identifying loss of imprinting of the IGF2 gene in a subject. The method in this aspect includes analyzing a biological sample from the subject for hypomethylation of a differentially methylated region (DMR) of the H19 gene and/or the IGF2 gene, and/or a polymorphism and/or fragment of the H19 DMR and/or the IGF2 DMR.

Typically, the subject is a human subject. Furthermore, in certain aspects, the H19 DMR or portion thereof, includes a CTCF binding site, for example, CTCF binding site 1 or CTCF binding site 6.

In certain aspects of this embodiment, the subject is an apparently normal subject. Therefore, in certain aspects, the subject is not known to have a colorectal neoplasm. Furthermore, in certain aspect, hypomethylation is analyzed in a DNA region corresponding to SEQ ID NO:6, an H19 DMR.

In certain aspects, the method further includes analyzing the biological sample for hypomethylation of a DMR of the IGF2 gene that corresponds to SEQ ID NO:1.

In one embodiment, the present invention relates to a method for identifying an increased risk of developing cancer in a subject. The method includes analyzing a biological sample from the subject for hypomethylation of a differentially methylated region (DMR) of an H19 gene, or a polymorphism and/or fragment of the H19 DMR. In certain aspects of the invention, the cancer is colorectal cancer.

One IGF2 DMR corresponds to SEQ ID NO:1, and is located at position −566 bp to −311 bp relative to exon 3 of IGF2 (i.e., nucleotides 661 to 916 of GenBank accession no. Y13633 (SEQ ID NO:35), incorporated herein in its entirety by reference). The DMR of SEQ ID NO:1 is analyzed for hypomethylation in preferred embodiments of the present invention. Other DMRs have been reported for the IGF2 gene, for example, a DMR around exon 3 (Sullivan M J et al., *Oncogene,* (1999) 18(52):7527-34.). Residues which are methylated within SEQ ID NO:1, typically CpG residues, can be identified using methods such as bisulfite genomic sequencing, as known in the art and as discussed in further detail herein (See e.g., Vu et al., *Genomics,* 64:132-43 (2000), incorporated herein in its entirety by reference). In preferred embodiments, methods of the present invention analyze 3 CpG residues displaying differential methylation that correspond to positions 747, 750 and 766 of the Genbank entry Y13633, incorporated herein in its entirety by reference (SEQ ID NO:35) (See FIGS. 4-6).

One DMR of H19 corresponds to SEQ ID NO:6 (i.e., nucleotides 2057 to 8070 of Genbank accession no. AF087017, incorporated herein by reference in its entirety (SEQ ID NO:37); which correspond in variant form to nucleotides 3829 to 9842 of AF125183 (SEQ ID NO:36) (See Cui et al., *Canc. Res.,* 61:4947-4950 (2001), incorporated herein by reference in its entirety; See also Cui et al., *Canc. Res.,* 62:6442-6446 (2002), incorporated herein by reference in its entirety)). The DMR of H19 is analyzed for hypomethylation in preferred embodiments of the present invention. Furthermore, it is known that DMRs are found in the human in all seven CTCF binding sites that showed differential methylation upstream of H19 gene. In addition, the H19 promoter region also has been shown to be differentially methylation. (Hark A T et al, *Nature.* (2000);405(6785):486-9., Bell A C et al., *Nature.* (2000) 405(6785):482-5. Steenman M J et al., *Nat Genet.* (1994) 7(3):433-9.). Residues which are methylated within SEQ ID NO:6, typically CpG residues, can be identified using methods such as bisulfite genomic sequencing, as known in the art and as discussed in further detail herein (See e.g., Vu et al., Genomics, 64:132-43 (2000)). All of the CpG residues within SEQ ID NO:6 show differential methylation (See FIGS. 4-6).

It will be recognized that in certain aspects, methods of the invention can determine methylation status by utilizing primers that bind the IGF2 gene or H19 gene at regions outside of the IGF2 DMR or the H19 DMR, but that allow analysis of a region of the IGF2 gene or H19 gene that includes the DMR. For example, primers can be selected which bind to regions within SEQ ID NOs:35 or 36 outside of the DMR region, but which can be used to analyze all or a portion of a DMR. Accordingly, certain aspects of the present invention analyze a DMR that consists essentially of SEQ ID NO:1 or SEQ ID NO:6, which indicates that a region of the IGF2 or H19 genes, respectively, is analyzed, that includes SEQ ID NO:1 or SEQ ID NO:6, but that also includes other sequences that flank SEQ ID NO:1 or SEQ ID NO:6. For example, 25, 50, 100, 200, or 250 additional flanking nucleotides can be included in the analysis of the DMRs of SEQ ID NO:1 or SEQ ID NO:6.

Hypomethylation of a DMR is present when there is a measurable decrease in methylation of the DMR. Methods for determining methylation states are provided herein. For example, the H19 DMR can be determined to be hypomethylated when it is methylated at less than 10, less than 5, or less than 3 sites of all of the greater than 25 methylation sites within the H19 DMR. Alternatively, as illustrated in the Examples provided herein, hypomethylation of the H19 DMR can be identified when less than 50% or less than 75% of the methylation sites analyzed are not methylated.

A fragment or portion of a H19 or IGF2 DMR is a fragment or portion of SEQ ID NO:6 or SEQ ID NO:1, respectively, that for the IGF2 DMR includes at least one methylation site, and preferably includes at least 2, and more preferably at least 3 methylation sites. In certain examples of the H19 and the IGF2 DMR, the fragment includes at least 1, 2, 3, 4, 5, 6, 7, 8, 9, 10, 11, 12, 13, 14, 15, 16, 17, 18, 19, 20, 21, 22, 23, 24, or 25 methylation sites. Methylation sites correspond to positions that are methylated in vivo in a normally methylated, aberrantly methylated, or hypermethylated state. The fragment includes a sufficient number of methylation sites to provide information regarding the methylation status of the entire H19 or IGF2 DMR or an important region of the H19 or IGF2 DMR. (See e.g., Nakagawa et al., *Proc. Natl. Acad. Sci.,* 98:591-96 (2001), incorporated by reference in its entirety). As illustrated in Example 2, many of the sites of methylation with the IGF2 DMR and H19 DMR are typically methylated in a coordinated manner. Therefore, methylation state can be analyzed for these DMRs by analyzing less than all of the methylation sites within the DMR. In certain aspects, the methylation sites are those sites for IGF2 that are located within the fragments amplified by the nested primer pairs SEQ ID NO:2 and SEQ ID NO:3 followed by SEQ ID NO:4 and SEQ ID NO:5, or SEQ ID NO:27 and SEQ ID NO:28 followed by SEQ ID NO:29 and SEQ ID NO:30. For H19, in certain aspects methylation sites of fragments of the present invention are those found within nested primer pairs SEQ ID NO:23 and SEQ ID NO:24 followed by SEQ ID NO:25 and SEQ ID NO:26.

A fragment of the H19 DMR or IGF2 DMR can be the region of the H19 DMR or IGF2 DMR that is amplified and/or flanked by primers that correspond to SEQ ID NOS:2-34. For example, the fragment of the H19 DMR can be the region of the H19 DMR that is amplified by the primer pair recited in SEQ ID NOS:23 and 24, or the primer pair recited in SEQ ID NOS:25 and 26, or by the nesting of SEQ ID NOS:23 and 24 followed by SEQ ID NOS:25 and 26. As another example, the fragment of the IGF2 DMR can be the region of the IGF2 DMR that is amplified by the primer pair recited in SEQ ID NOS: 27 and 28, or the primer pair recited in SEQ ID NOS:29 and 30, or by the nesting of SEQ ID NOS:27 and 28 followed by SEQ ID NOS:29 and 30. As another example, the fragment of the IGF2 DMR can be the region of the IGF2 DMR that is amplified by the primer pair recited in SEQ ID NOS: 2 and 3, or the primer pair recited in SEQ ID NOs:4 and 5, or by the nesting of SEQ ID NOS:2 and 3 followed by SEQ ID NOs:4 and 5. In certain aspects the present invention includes analyzing the biological sample for hypomethylation of positions within the region of the H19 DMR that are analyzed using the nested primer pairs SEQ ID NOs:23 and 24, followed by SEQ ID NOs:25 and 26, as illustrated in the Examples herein. Furthermore, in certain aspects, hypomethylation is analyzed in a DNA region corresponding to SEQ ID NO:1, an IGF2 DMR. In certain aspects the method includes analyzing the biological sample for hypomethylation of positions within the region of the IGF2 DMR that are analyzed using the nested primer pairs SEQ ID NOs:2 and 3, followed by SEQ ID NOs:4 and 5, or the region analyzed using primer pairs SEQ ID NOs: 27 and 28, followed by SEQ ID NOs:29 and 30, as illustrated in the Examples herein.

The fragment of an H19 DMR or IGF2 DMR in certain aspects, is 25, 50, 100, 150, 200, 250, 500, 1000, 2000, 3000, 4000, 50000, or 60000 nucleotides in length. In certain aspects, methods of the invention analyze methylation of a H19 DMR or IGF2 DMR sequence that binds under stringent conditions to the H19 DMR (SEQ ID NO:6) or the IGF2 DMR (SEQ ID NO:1). Furthermore, in certain aspects, methods of the invention analyze methylation of an H19 DMR or IGF2 DMR, or a fragment thereof, that is at least 75%, 80%, 85%, 90%, 95%, 96%, 97%, 98%, 99%, or 99.9% identical to SEQ ID NO:6 or SEQ ID NO:1, respectively, or a portion of SEQ ID NO:6 or SEQ ID NO:1.

In certain aspects, the H19 DMR or fragment thereof, includes at least one CTCF binding site, for example CTCF binding site 1 or CTCF binding site 6 (corresponding to nucleotides 7855-8192 of Genbank accession no. AF125183, incorporated herein in its entirety by reference) (SEQ ID NO:36) (See Bell, et al., *Nature* 405:482-85 (2000) (incorporated herein by reference); Hark et al., *Nature* 405:486-89 (2000) (incorporated herein by reference); and Bell et al., *Cell* 98, 387-96 (1999) (incorporated herein by reference)). CTCF binding sites can be identified by aligning sequences of the IGF2 or H19 DMR to known CTCF binding sites (See e.g., Bell et al. 1999, supra, at FIG. 6). In one example, a fragment of an H19 DMR includes a fragment of the H19 DMR that includes the canonical CTCF binding sites, nucleotides 3010 to 3172 of SEQ ID NO:6, which corresponds to a portion of the H19 DMR from −5315 to −5153 bp upstream of the start site of transcription of H19 (Cui et al., *Canc. Res.,* 61:4947-4950 (2001), incorporated herein in its entirety by reference). One of the effects of methylation of the DMR upstream of the H19 gene, also referred to herein as the H19 DMR, that has been reported is the abrogation of binding of the transcription factor CTCF (Kanduri et al., *Curr. Biol.,* 10:853-56 (2000); Szabo et al., *Curr. Biol.,* 10:607-10 (2000); Hark et al., *Nature,* 405:486-89 (2000); and Bell et al., *Nature,* 405:482-85 (2000)). CTCF binding can discriminate differentially methylated DMRs on the paternal versus maternal alleles in vivo (Kanduri et al., *Curr. Bio.,* 10: 853-856 (2000)).

A fragment of an H19 DMR, in certain aspects includes less than all of the repeats found in the H19 gene (Nakagawa et al., 2001, supra). The H19 DMR includes 2 copies of a repeat unit, which includes one 450-bp repeat and seven 400-bp repeats (Id.). Therefore, in one example, a fragment of an H19 DMR includes one copy of the H19 DMR repeat unit. In another example, a fragment of an H19 DMR includes at least one copy of the 450-bp repeat and at least one copy of the 400 base pair repeat (Id.).

Polymorphisms of the H19 DMR and the IGF2 DMR have been identified. For example, in the H19 DMR, a polymorphism has been identified at nucleotide 8008 (C/A), nucleotide 8097 (G/A), and nucleotide 8217 (C/G) of accession no. AF125183 (SEQ ID NO:36) (Nakagawa et al., *Proc. Nat. Acad. Sci.,* 98:591-96 (2001), incorporated herein by reference). Furthermore, the annotations of Genbank AF125183 (SEQ ID NO:36) identify nucleotides 4489, 4593, 6368, 7342, 7523, 7547, 7591, 7966, 8008, 8097, 8217, 8271, 9554, and 9839 as sites of nucleotide variations. A skilled artisan will recognize that polymorphic versions of the IGF2 DMR or the H19 DMR, or polymorphic versions of fragments of these DMRs can be analyzed in the methods of the present invention. Polymorphisms or mutations in the H19 DMR or IGF2 DMR can be identified using methods known in the art.

Although many conventional genetic mutations have been observed in human cancer, most do not occur at high frequency in the general population. Certain embodiments of the present invention are based on the finding of an association between loss of imprinting (LOI) of the IGF2 gene and family history of colorectal cancer (CRC) and between LOI of the IGF2 gene and present or past personal history of colorectal neoplasia. Accordingly, methods of the present invention analyze common molecular markers of cancer risk to identify an increased risk of developing cancer in a subject. In certain embodiments, the method is a DNA-based blood test for the general population.

Certain embodiments of the present invention are based on the finding that loss of imprinting of the IGF2 gene is associated with cancers such as colorectal cancer, and that loss of imprinting of the IGF2 gene is correlated with hypomethylation of both the IGF2 gene and the H19 gene. Accordingly, methods of certain embodiments of the present invention analyze hypomethylation in the IGF2 gene and/or the H19 gene to identify loss of imprinting of the IGF2 gene and to identify an increased risk of developing cancer.

Accordingly, the present invention relates to a method for identifying an increased risk of developing cancer in a subject. The method includes analyzing a first biological sample from the subject for loss of imprinting of the IGF2 gene and/or the H19 gene. According to the method, a loss of imprinting is indicative of an increased risk of developing cancer.

A method of the present invention can also be used to infer a cancer risk of a subject. As discussed above, the method can include analyzing a first biological sample from the subject for loss of imprinting of the IGF2 gene. According to the method, imprinting status is associated with a cancer risk, for example in certain embodiments a loss of imprinting is indicative of an increased risk of developing cancer.

A method of the invention can include analyzing genomic DNA for altered methylation of the IGF2 gene or the H19 gene. The method for example, includes analyzing genomic DNA from the sample for hypomethylation of the IGF2 gene or the H19 gene, wherein hypomethylation is associated with an increased risk of developing cancer. Additionally, the altered methylation can occur upstream of a coding region of a gene, or within either exons or introns. For example, hypomethylation of a DMR in the second intron of the IGF2 gene, or of a DMR upstream of the H19 gene, can be associated with cancer.

As illustrated in the Example section, especially Example 1, the present invention in certain embodiments, provides a prognostic test for cancer risk, especially colorectal cancer risk. The population frequency of the hypomethylation of IGF2 is approximately 8% when the sample is a blood sample. In embodiments involving a second sample isolated from colorectal tissue, an additional 10% of the population are positive. Therefore, the present invention provides methods that identify cancer risk at high frequency in the general population. A positive blood test confers an increased risk of colorectal cancer, and potentially can be used to identify high risk patients in the general population, for increased cancer surveillance. The method provides an additional advantage in that a negative test excludes patients from repeat colonoscopic examination who may have a positive family history. Furthermore, the test can be performed on RNA or DNA samples.

Loss of imprinting, an epigenetic alteration affecting the insulin-like growth factor II gene (IGF2), is found in normal colonic mucosa of approximately 30% of colorectal cancer (CRC) patients, compared to 10% of those without colorectal neoplasia (Cui, H., et al., *Nat. Med.* 4, 1276-1280 (1998)). Therefore, LOI occurs at a relatively high rate in CRC patients and in patients without colorectal neoplasia. Before the present invention, however, it was not known, whether LOI in normal cells identifies patients with a history of, presence of, or positive family history for colorectal neoplasia in a population not selected for colorectal cancer.

In the study provided in Example 1, 11 of 123 (9.0%) of patients with no family history of CRC showed LOI in lymphocytes, compared to 13 of 49 (27%) with a positive family history (adjusted odds ratio 4.41, 95% CI 1.62-12.0, p=0.004). Similarly, 7 of 106 (6.6%) patients without past or present colonic neoplasia showed LOI, compared to 12 of 56 (21%) patients with adenomas, and 5 of 9 (56%) patients with CRC (adjusted odds ratios 4.10 [95% CI 1.30-12.8, p=0.016] and 34.4 [95% CI 6.10-194, p<0.001], respectively). These data support the usefulness and effectiveness of methods of the present invention in identifying an increased risk of developing cancer.

For a blood test of risk assessment to be most practical, a DNA rather than RNA-based test can be used. Accordingly, in certain embodiments, methods of the present invention include analyzing the genomic DNA for hypomethylation of a differentially methylated region (DMR) of IGF2 corresponding to SEQ ID NO:1 and/or a polymorphism of a region of a genome corresponding to SEQ ID NO:1, or a fragment of SEQ ID NO:1 or a polymorphism thereof. As illustrated herein, the vast majority of tissues with LOI (i.e., 11 of 12 tissues analyzed herein) show hypomethylation of IGF2, whereas tissues with normal imprinting show normal methylation of IGF2. Thus, LOI in lymphocytes is linked to hypomethylation of a differentially methylated region of IGF2.

Since the present specification discloses that hypomethylation of H19 is associated with loss of imprinting of IGF2, in certain aspects, methods of the present invention include analyzing the genomic DNA for hypomethylation of a differentially methylated region (DMR) of H19, such as the DMR corresponding to SEQ ID NO:6, a polymorphism of a region of a genome corresponding to SEQ ID NO:6, or a fragment of SEQ ID NO:6 or a polymorphism thereof. As illustrated in Example 2, the majority of tissues with LOI show hypomethylation of H19, whereas tissues with normal imprinting, in general show normal methylation of H19. Thus, LOI in lymphocytes is correlated with hypomethylation of a differentially methylated region of H19.

A method according to the present invention can be performed during routine clinical care, for example as part of a general regular checkup, on a subject having no apparent or suspected neoplasm such as cancer. Therefore, the present invention in certain embodiments, provides a screening method for the general population. The methods of the present invention can be performed at a younger age than present cancer screening assays, for example where the method can be performed on a subject under 65, 55, 50, 40, 35, 30, 25, or 20 years of age.

If the biological sample of the subject in question is found to exhibit LOI, for example as the result of hypomethylation of the DMR of IGF2 corresponding to the polynucleotide of SEQ ID NO:1 or hypomethylation of the DMR of H19 corresponding to SEQ ID NO:6, then that subject is identified as having an increased probability of having cancer. In these embodiments, further diagnostic tests may be carried out to probe for the possibility of cancer being present in the subject. Examples of such further diagnostic tests include, but are not limited to, chest X-ray, carcinoembryonic antigen (CEA) or prostate specific antigen (PSA) level determination, colorectal examination, endoscopic examination, MRI, CAT scanning, or other imaging such as gallium scanning, and barium imaging. Furthermore, the method of the invention can be coincident with routine sigmoidoscopy/colonoscopy of the subject. The method could involve use of a very thin tube, or a digital exam to obtain a colorectal sample.

The method of the present invention, especially when used to detect local LOI, can be repeated at regular intervals. While not wanting to be limited to a particular theory, methods directed to detecting local LOI by analyzing a blood sample for LOI, typically identify germline mutations. Therefore, typically one test is sufficient. However, for methods used to detect local LOI, a third sample can be isolated, for example from colorectal tissue, for example at least 2 months after isolation of the second sample For example, the third sample can be isolated at about 1 year after the second sample was isolated. In fact, the method can be repeated annually, for example at an annual routine physical exam. Using this regular testing, a method of the present invention is used to screen for an increased risk of developing colorectal cancer by a method that includes analyzing the third sample from the subject for loss of imprinting of the IGF2 gene or the H19 gene.

Additional diagnostic tests can be performed in the future, even if no cancer is present at the time LOI is detected. For example, if LOI is detected in a biological sample of a subject and indicates an increased risk of contracting cancer, periodic (e.g., every 1 to 12 months) chest X-rays, colorectal examinations, endoscopic examination, MRI, CAT scanning, other imaging such as gallium scanning, and/or barium imaging can be scheduled for that subject. Therefore, in these embodiments, LOI is used as a screening assay to identify subjects for whom more frequent monitoring is justified.

The biological sample can be virtually any biological sample, particularly a sample that contains RNA or DNA from the subject. The biological sample can be a tissue sample which contains 1 to 10,000,000, 1000 to 10,000,000, or 1,000,000 to 10,000,000 somatic cells. However, it is possible to obtain samples that contain smaller numbers of cells, even a single cell in embodiments that utilize an amplification protocol such as PCR. The sample need not contain any intact cells, so long as it contains sufficient biological material (e.g., protein or genetic material, such as RNA or DNA) to assess the presence or absence of LOI of IGF2 or H19, such as LOI of the IGF2 gene caused by hypomethylation of IGF2 or H19 in the subject.

According to the present invention, the biological or tissue sample can be drawn from any tissue that is susceptible to cancer. For example, the tissue may be obtained by surgery, biopsy, swab, stool, or other collection method. The biological sample for methods of the present invention can be, for example, a sample from colorectal tissue, or in certain embodiments, can be a blood sample, or a fraction of a blood sample such as a peripheral blood lymphocyte (PBL) fraction. Methods for isolating PBLs from whole blood are well known in the art. An example of such a method is provided in the Example section herein. In addition, it is possible to use a blood sample and enrich the small amount of circulating cells from a tissue of interest, e.g., colon, breast, etc. using a method known in the art.

When the method of the present invention provides a method for identifying an increased risk of developing colorectal cancer, a biological sample can be isolated from the colon. Such a tissue sample can be obtained by any of the above described methods, or by the use of a swab or biopsy. In the case of stomach and esophageal cancers, the tissue sample may be obtained by endoscopic biopsy or aspiration, or stool sample or saliva sample. In the case of leukemia, the tissue sample is typically a blood sample.

As disclosed above, the biological sample can be a blood sample. The blood sample can be obtained using methods known in the art, such as finger prick or phlebotomy. Suitably, the blood sample is approximately 0.1 to 20 ml, or alternatively approximately 1 to 15 ml with the volume of blood being approximately 10 ml.

Accordingly, in one embodiment, the identified cancer risk is for colorectal cancer, and the biological sample is a tissue sample obtained from the colon, blood, or a stool sample. In another embodiment, the identified cancer risk is for stomach cancer or esophageal cancer, and the tissue may be obtained by endoscopic biopsy or aspiration, or stool sample or saliva sample. In another embodiment, the identified cancer risk is esophageal cancer, and the tissue is obtained by endoscopic biopsy, aspiration, or oral or saliva sample. In another embodiment, the identified cancer risk is leukemia/lymphoma and the tissue sample is blood.

In the present invention, the subject is typically a human but also can be any mammalian organism, including, but not limited to, a dog, cat, rabbit, cow, bird, rat, horse, pig, or monkey.

As mentioned above, for certain embodiments of the present invention, the method is performed as part of a regular checkup. Therefore, for these methods the subject has not been diagnosed with cancer, and typically for these present embodiments it is not known that a subject has a hyperproliferative disorder, such as a colorectal neoplasm.

Methods of the present invention identify a risk of developing cancer for a subject. A cancer can include, but is not limited to, colorectal cancer, esophageal cancer, stomach cancer, leukemia/lymphoma, lung cancer, prostate cancer, uterine cancer, breast cancer, skin cancer, endocrine cancer, urinary cancer, pancreas cancer, other gastrointestinal cancer, ovarian cancer, cervical cancer, head cancer, neck cancer, and adenomas. In one aspect, the cancer is colorectal cancer.

A hyperproliferative disorder includes, but is not limited to, neoplasms located in the following: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital. Typically, as used herein, the hyperproliferative disorder is a cancer. In certain aspects, the hyperproliferative disorder is colorectal cancer.

The method can further include analysis of a second biological sample from the subject at a target tissue for loss of imprinting of the IGF2 gene, wherein a loss of imprinting in the second sample is indicative of an increased risk of developing cancer in the target tissue. In certain embodiments, the second biological sample is not a blood sample. For example, the first biological sample can be a blood sample and the second biological sample can be isolated from colorectal tissue. In these embodiments analysis of the blood sample can be performed to identify overall risk of developing cancer, whereas the colorectal sample can be analyzed to identify subjects that have an increased risk of developing colorectal cancer. In certain embodiment, the DMRs of both IGF2 and H19 are analyzed for hypomethylation, wherein hypomethylation of one or both of the DMRs is associated with an increased risk of developing cancer.

In another embodiment, the present invention provides a method for managing health of a subject. The method includes performing the method for identifying an increased risk of developing cancer discussed above and performing a traditional cancer detection method. For example a traditional cancer detection method can be performed if the method for identifying cancer risk indicates that the subject is at an increased risk for developing cancer. Many traditional cancer detection methods are known and can be included in this aspect of the invention. The traditional cancer detection method can include, for example, one or more of chest X-ray, carcinoembryonic antigen (CEA) level determination, colorectal examination, endoscopic examination, MRI, CAT scanning, or other imaging such as gallium scanning, and barium imaging, and sigmoidoscopy/colonoscopy, a breast exam, or a prostate specific antigen (PSA) assay.

In another embodiment, the present invention provides a method for prognosing cancer risk of a subject. The method includes analyzing a first biological sample from the subject for altered methylation of the IGF2 gene or the H19 gene. In certain aspects of the invention, the altered methylation is hypomethylation of SEQ ID NO:1, or a polymorphism and/or fragment thereof, or hypomethylation of SEQ ID NO:6, or a polymorphism and/or fragment thereof. Hypomethylation of either or both genes is indicative of an increased risk of developing cancer. In this aspect of the invention, the first biological sample is typically a blood sample.

In another aspect, the present invention provides a method for identifying predisposition to colorectal cancer of a subject. The method includes identifying a loss of imprinting in a biological sample from the subject and correlating the loss with a predisposition to colorectal cancer. Loss of imprinting is associated with an increased predisposition to colorectal cancer. The method includes analyzing a first biological sample from the subject for hypomethylation of a differentially methylated region DMR of IGF2 corresponding to SEQ ID NO:1, or a polymorphism or fragment thereof, or hypomethylation of a DMR of H19 corresponding to SEQ ID NO:6, or a polymorphism or fragment thereof. Hypomethylation of either or both of these DMRs is indicative of an increased risk of developing cancer. In this aspect of the invention, the first biological sample is typically a colorectal sample.

In another embodiment, the present invention provides to a method for screening a subject for cancer. The method includes analyzing a first biological sample from the subject for loss of imprinting of the IGF2 gene. According to the method, a loss of imprinting is indicative of an increased risk of developing cancer. The method can include analyzing genomic DNA from the sample for hypomethylation of the IGF2 gene or the H19 gene.

As disclosed herein, methods of the present invention involve analyzing a biological sample for loss of imprinting of IGF2 gene. Genomic imprinting is an epigenetic modification of a specific parental chromosome in the gamete or zygote that leads to monoallelic or differential expression of the two alleles of a gene in somatic cells of the offspring. Imprinting affects various essential cellular and developmental processes, including intercellular signaling, RNA processing, cell cycle control, and promotion or inhibition of cellular division and growth.

Genomic imprinting is a parent of origin-specific gene silencing that is epigenetic in origin, i.e. not involving the DNA sequence per se but methylation and likely other modifications heritable during cell division (Feinberg, A. P., in *The Metabolic and Molecular Bases of Inherited Disease,* C. R. Scriver, et al., Eds. (McGraw-Hill, New York, 2002)). Loss of imprinting (LOI) of IGF2 was first discovered in embryonal tumors of childhood, such as Wilms tumor (WT), but is one of the most common alterations in cancer, including ovarian, lung, liver, and colon (Feinberg, A. P., in *The Metabolic and Molecular Bases of Inherited Disease,* C. R. Scriver, et al., Eds. (McGraw-Hill, New York, 2002)). The consequence of LOI is best understood in WT. Here it serves as a gatekeeper in about half of tumors, especially those that occur with relatively late onset, and leads to increased expression of IGF2 (Ravenel, J. D., et al., *J Natl. Cancer Inst.* 93, 1698-1703 (2001)), an important autocrine growth factor in a wide variety of cancers including CRC (Lahm, H., et al., *Br. J. Cancer* 65, 341-346 (1992); M. C. Gelato and J. Vassalotti, *J. Clin. Endocrinol. Metab.* 71, 1168-1174 (1990); El-Badry, O. M., et al., *Cell Growth Diff.* 1, 325-331 (1990); Yee, D., et al., *Cancer Res.* 48, 6691-6696 (1988); Lamonerie, T., et al., *Int. J. Cancer* 61, 587-592 (1995); and Pommier, G. J., et al., *Cancer Res.* 52, 3182-3188 (1992)).

Loss of imprinting can be caused by hypomethylation or hypermethylation of a gene. The present invention includes methods wherein loss of imprinting is identified by hypomethylation of the IGF2 gene or the H19 gene. For example, the loss of imprinting can be the result of hypomethylation of a DMR within the IGF2 gene, corresponding to SEQ ID NO:1, or a polymorphism and/or fragment thereof, particularly positions 87, 90, and 106 within SEQ ID NO:1. or hypomethylation of a DMR within the H19 gene, or a polymorphism and/or fragment thereof, corresponding to SEQ ID NO:6.

Methods for detecting loss of imprinting are typically quantitative methods for analyzing imprinting status. The presence or absence of LOI may be detected by examining any condition, state, or phenomenon which causes LOI or is the result of LOI. Such conditions, states, and phenomena include, but are not limited to:

1. Causes of LOI, such as the state or condition of the cellular machinery for DNA methylation, the state of the imprinting control region on chromosome 11, the presence of trans-acting modifiers of imprinting, the degree or presence of histone deacetylation;

2. State of the genomic DNA associated with the genes or gene for which LOI is being assessed, such as the degree of DNA methylation;

3. Effects of LOI, such as:
   a. Relative transcription of the two alleles of the genes or gene for which LOI is being assessed;
   b. Post-transcriptional effects associated with the differential expression of the two alleles of the genes or gene for which LOI is being assessed;
   c. Relative translation of the two alleles of the genes or gene for which LOI is being assessed;
   d. Post-translational effects associated with the differential expression of the two alleles of the genes or gene for which LOI is being assessed;
   e. Other downstream effects of LOI, such as altered gene expression measured at the RNA level, at the splicing level, or at the protein level or post-translational level (i.e., measure one or more of these properties of an imprinted gene's manifestation into various macromolecules); changes in function that could involve, for example, cell cycle, signal transduction, ion channels, membrane potential, cell division, or others (i.e., measure the biological consequences of a specific imprinted gene being normally or not normally imprinted (for example, QT interval of the heart). Another group of macromolecular changes include processes associated with LOI such as histone acetylation, histone deacetylation, or RNA splicing.

When detecting the presence or absence of LOI by relying on any one of these conditions, states, or phenomena, it is possible to use a number of different specific analytical techniques. In particular, it is possible to use any of the methods for determining the pattern of imprinting known in the art. It is recognized that the methods may vary depending on the gene to be analyzed.

Conditions, states, and phenomena which may cause LOI and may be examined to assess the presence or absence of LOI include the state or condition of the cellular machinery for DNA methylation, the state of the imprinting control region on chromosome 11, the presence of trans-acting modifiers of imprinting, the degree or presence of histone deacetylation or histone deacetylation, imprinting control center, transacting modulatory factors, changes in chromatin caused by polycomb-like proteins, trithorax-like proteins, human homologues of other chromatin-affecting proteins in other species such as Su(var) proteins in *Drosophila,* SIR proteins in yeast, mating type silencing in yeast, or XIST-like genes in mammals.

It is also possible to detect LOI by examining the DNA associated with the gene or genes for which the presence or absence of LOI is being assessed. By the term "the DNA associated with the gene or genes for which the presence or absence of LOI is being assessed" it is meant the gene, the DNA near the gene, or the DNA at some distance from the gene (as much as a megabase or more away, e.g., methylation changes can be that far away, since they act on chromatin over long distances). Typically, for the present invention LOI is identified or analyzed or detected by detecting hypomethylation of a DMR of the IGF2 gene and/or of a DMR of the H19 gene, as described herein.

The degree of methylation in the DNA, associated with the gene or genes for which the presence or absence of LOI is being assessed, can be measured or identified using a number of analytical techniques. As discussed above, the method in certain aspects of the invention, detects LOI by detecting hypomethylation of a DMR of the IGF2 gene, which corresponds to SEQ ID NO:1, or a polymorphism and/or fragment thereof. In certain aspects of the invention also discussed above, the method detects LOI by detecting hypomethylation of a DMR of the H19 gene, which corresponds to SEQ ID NO:6, or a polymorphism and/or fragment of the H19 DMR.

Numerous methods for analyzing methylation status of a gene are known in the art and can be used in the methods of the present invention to identify either hypomethylation or hypermethylation of the H19 gene or the IGF2 gene. As illustrated in the Examples herein, analysis of methylation can be performed by bisulfite genomic sequencing. Accordingly, denatured genomic DNA can be treated with freshly prepared bisulfite solution at 55° C. in the dark overnight, followed by column purification and NaOH treatment, as described in more detail in the Examples section. Bisulfite treatment modifies DNA converting unmethylated, but not methylated, cytosines to uracil. In aspects of the invention in which the IGF2 DMR is analyzed, treated DNA can be amplified by PCR, using primers 5'-GGTGAG-GATGGGTTTTTGTT-3' (SEQ ID NO:2) and 5'-CTACTCTCCCAACCTCCCTAA-3' (SEQ ID NO:3), annealing at 55° C., followed by nested PCR using primers 5'-ATTGGGGGTGGAGGGTGTAT-3' (SEQ ID NO:4) and 5'-TCTATTACACCCTAAACCCAA-3' (SEQ ID NO:5), annealing at 52° C. Other conditions can include those described previously (Cui, H., et al., *Nat. Med.* 4, 1276-1280 (1998)).

In another aspect, the IGF2 DMR sequence analyzed corresponds to GenBank nucleotides 631-859 (accession no. Y13633) and can be analyzed after bisulfite treatment using primers 5'-GGGAATGTTTATTTATGTATGAAG-3' (SEQ ID NO:27) and 5'-TAAAAACCTCCTCCACCTCC-3' (SEQ ID NO:28), annealing at 55° C. followed by 5'-TAATTTATT-TAGGGTGGTGTT-3' (SEQ ID NO:29) and 5'-TCCAAA-CACCCCCACCTTAA-3' (SEQ ID NO:30), annealing at 50° C. Other conditions can be those described in Cui et al., *Cancer Research*, 61:4847-4950 (2001) (incorporated herein in its entirety by reference).

In another aspect, the bisulfite genomic sequencing can be performed of the H19 DMR using the following primers after bisulfite treatment:

| | |
|---|---|
| 5'-GAGTTTGGGGGTTTTTGTATAGTAT-3' and | (SEQ ID NO: 23) |
| 5'-CTTAAATCCCAAACCATAACACTA-3', followed by | (SEQ ID NO: 24) |
| 5'-GTATATGGGTATTTTTGGAGGT-3' and | (SEQ ID NO: 25) |
| 5'-CCATAACACTAAAACCCTCAA-3', | (SEQ ID NO: 26) | both annealing at 50° C. Other conditions can be those described in Cui et al., *Cancer Research*, 61:4847-4950 (2001).

In another aspect, the bisulfite genomic sequencing can be performed of the H19 DMR using the following primers after bisulfite treatment:

| | |
|---|---|
| 5'-GTATAGGTATTTTTGGAGGTTTTTTA-3' and | (SEQ ID NO: 31) |
| 5'-CCTAAAATAAATCAAACACATAACCC-3'. | (SEQ ID NO: 32) |
| The second PCR primers were: | |
| 5'-GAGGTTTTTTATTTTAGTTTTGG-3' and | (SEQ ID NO: 33) |
| 5'-ACTATAATATATAAAGGTACAC-3'. | (SEQ ID NO: 34) |

In another aspect, genomic sequencing can be performed on the H19 DMR using the following primer pairs:

| | | |
|---|---|---|
| H1 | 5'-ATCTTGCTGACCTCACCAAGG-3' and | (SEQ ID NO: 7) |
| | 5'-CGATACGAAGACGTGGTGTGG-3'; | (SEQ ID NO: 8) |
| H2 | 5'-CCGACTAAGGACAGCCCCCAAA-3' and | (SEQ ID NO: 9) |
| | 5'-TGGAAGTCTCTGCTCTCCTGTC-3'; | (SEQ ID NO: 10) |
| H3 | 5'-ACAGTGTTCCTGGAGTCTCGCT-3' | (SEQ ID NO: 11) |
| | 5'-CACTTCCGATTCCACAGCTACA-3'; | (SEQ ID NO: 12) |
| H4 | 5'-ACAGGGTCTCTGGCAGGCTCAA-3' | (SEQ ID NO: 13) |
| | 5'-ATGAGTGTCCTATTCCCAGATG-3'; | (SEQ ID NO: 14) |
| H5 | 5'-AACTGGGGTTCGCCCGTGGAA -3' | (SEQ ID NO: 15) |
| | 5'-CAAATTCACCTCTCCACGTGC-3'; | (SEQ ID NO: 16) |
| H6 | 5'-GATCCTGATGGGGTTAGGATGT-3' | (SEQ ID NO: 17) |
| | 5'-GGAATTTCCATGGCATGAAAAT-3'; | (SEQ ID NO: 18) |
| H7 | 5'-GGTCTGCCTTGGTCTCGTAACT-3' | (SEQ ID NO: 19) |
| | 5'-GGCCAGTTTCCTGTCTGAAGAC-3'; and | (SEQ ID NO: 20) |
| H8 | 5'-CAGTCTCCACTCCACTCCCAAC-3' | (SEQ ID NO: 21) |
| | 5'-GACCTCTCCCTCCCAGACCACT-3'. | (SEQ ID NO: 22) |

It will be recognized for the primers of the invention that depending on the site bound by the primer and the direction of extension from a primer, that the primers listed above can be used in different pairs. Furthermore, it will be recognized that additional primers can be identified within the IGF2 and H19 DMRs, especially primers that allow analysis of the same methylation sites as those analyzed with primers that correspond to SEQ ID NOs:1-5, and 7-34. In certain aspects, primers allow analysis of the same methylation sites as the primer pairs that correspond to SEQ ID NOs:2 and 3, 4 and 5, 23 and 24, 25 and 26, 27 and 28 and the primer pair that corresponds to SEQ ID NOS: 29 and 30. The regions amplified and/or otherwise analyzed using the above primer pairs can be readily identified by a skilled artisan using sequence comparison tools and/or by analyzing nucleotides fragments that are replicated using the primers. Some of the primers are intended for use after bisulfite treatment. These primer pairs include SEQ ID NOS:2 and 3, 4 and 5, 23 and 24, 25 and 26, 27 and 28, 29 and 30, 31 and 32, and the primer pair corresponding to SEQ ID NOs:33 and 34. Therefore, it will be understood that identification of the binding sites for these primers using computational methods, will take into account that the primers can preferably bind to a polynucleotide whose sequence is modified by bisulfite treatment. For example, for IGF2 DMR analysis, the primers that correspond to SEQ ID NOs:27-30 bind to the following positions, based on the Genbank Y13633 sequence, incorporated herein by reference in its entirety (SEQ ID NO:35): F1: 631-654, R1: 840-859, F2: 688-708, R2: 823-842. As another example, for H19 DMR analysis, the primers that correspond to SEQ ID NOs:31-34 (which for example are used to analyze CTCF binding site 1) bind to the following positions, based on the Genbank AF087017 sequence, incorporated herein by reference (SEQ ID NO:37), F1: 2995-3020, R1: 3284-3309, F2: 3010-3031, R2: 3151-3172. As another example, for H19

DMR analysis, the primers that correspond to SEQ ID NOs: 23-26 (which for example are used to analyze CTCF binding site 6) bind to the following positions, based on the Genbank AF087017 sequence, incorporated herein by reference, F1: 6083-6107, R1: 6397-6420, F2: 6104-6125, R2: 6387-6407.

Bisulfite treatment can be carried out using the CpG Genome DNA Modification kit (Intergen, Purchase, N.Y.) with the following modifications of the manufacturer's protocol: denatured genomic DNA (4 μg) can be incubated at 55° C. in the dark overnight in 1100 μl of freshly prepared Reagent I, with subsequent column purification with the QIAquick PCR purification kit (Qiagen). Purified DNA can be treated at 37° C. for 15 min with freshly prepared 3 M NaOH to a final concentration of 0.3 M NaOH. Then the DNA can be precipitated with ethanol and dissolved in 40 μl of 10 mM Tris (pH 8)-1 mM EDTA for nested PCR. PCR products were purified on 2% agarose gels for direct sequencing as described above. The annealing temperature was 55° C. For sequencing individual clones, the PCR products can be subcloned into a TA Cloning vector (Invitrogen, Carlsbad, Calif.) according to the manufacturer's instructions, and a series of clones, such as 10-15 clones, can be selected for sequencing.

PCR products can be purified using the QIAEX II gel extraction kit (Qiagen) and directly sequenced with an ABI Prism 377 DNA sequencer using the BigDye™ Terminator Cycle Sequencing kit following the manufacturer's protocol (PE Applied Biosystems, Foster City, Calif.).

Certain embodiments of the present invention provide the above-listed primer pairs, typically in an isolated form, and/or the above-listed primers. Accordingly, in these embodiments, the present invention provides isolated oligonucleotides and primer pairs corresponding to SEQ ID NOS:2 and SEQ ID NO:3, SEQ ID NO:4 and SEQ ID NO:5, SEQ ID NO:6 and SEQ ID NO:7, SEQ ID NO:8, and SEQ ID NO:9, SEQ ID NO:9 and SEQ ID NO:10, SEQ ID NO:11 and SEQ ID NO:12, SEQ ID NO:13 and SEQ ID NO:14; SEQ ID NO:15 and SEQ ID NO:16, SEQ ID NO:17 and SEQ ID NO:18, SEQ ID NO:19 and SEQ ID NO:20, SEQ ID NO:21 and SEQ ID NO:22, SEQ ID NO:23 and SEQ ID NO:24, SEQ ID NO:25 and SEQ ID NO:26, SEQ ID NO:27 and SEQ ID NO:28, SEQ ID NO:29 and SEQ ID NO:30. In certain aspects the present invention provides isolated primer pairs, including SEQ ID NO:2 and SEQ ID NO:3; SEQ ID NO:4 and SEQ ID NO:5; SEQ ID NO:23 and SEQ ID NO:24; SEQ ID NO:25 and SEQ ID NO:26; SEQ ID NO:27 and SEQ ID NO:28; and SEQ ID NO:29 and SEQ ID NO:30.

Altered methylation can be identified by identifying a detectable difference in methylation. For example, hypomethylation can be determined by identifying whether after bisulfite treatment a uracil or a cytosine is present at residues corresponding to position 87, 90, and 106 of SEQ ID NO:1. If uracil is present after bisulfite treatment, then the residue is unmethylated. Hypomethylation is present when there is a measurable decrease in methylation, for example a measurable decrease in methylation of residues corresponding to positions 87, 90, and 106 of SEQ ID NO:1, as illustrated in the Example section herein, or a measurable decrease in methylation of residues corresponding to methylated positions within the polynucleotides analyzed using the primers disclosed herein.

In an alternative embodiment, the method for analyzing methylation of the DMR can include amplification using a primer pair specific for methylated residues within a DMR of the IGF2 gene or the H19 gene. In these embodiments, selective hybridization or binding of at least one of the primers is dependent on the methylation state of the target DNA sequence (Herman et al., Proc. Natl. Acad. Sci. USA, 93:9821 (1996)). For example, the amplification reaction can be preceded by bisulfite treatment, and the primers can selectively hybridize to target sequences in a manner that is dependent on bisulfite treatment. For example, one primer can selectively bind to a target sequence only when one or more base of the target sequence is altered by bisulfite treatment, thereby being specific for a methylated target sequence.

Other methods are known in the art for determining methylation status of a gene, such as the IGF2 gene or the H19 gene, including, but not limited to, array-based methylation analysis and Southern blot analysis.

Methods using an amplification reaction, for example methods above for detecting hypomethylation of the IGF2 DMR or the H19 DMR, can utilize a real-time detection amplification procedure. For example, the method can utilize molecular beacon technology (Tyagi S., et al., *Nature Biotechnology*, 14: 303 (1996)) or Taqman™ technology (Holland, P. M., et al., *Proc. Natl. Acad. Sci. USA*, 88:7276 (1991)).

Also methyl light (Trinh B N, Long T I, Laird P W. DNA methylation analysis by MethyLight technology, Methods, 25(4):456-62 (2001), incorporated herein in its entirety by reference), Methyl Heavy (Epigenomics, Berlin, Germany), or SNuPE (single nucleotide primer extension) (See e.g., Watson D., et al., *Genet Res.* 75(3):269-74 (2000)). Can be used in the methods of the present invention related to identifying altered methylation of IGF2.

As used herein, the term "selective hybridization" or "selectively hybridize" refers to hybridization under moderately stringent or highly stringent physiological conditions, which can distinguish related nucleotide sequences from unrelated nucleotide sequences.

As known in the art, in nucleic acid hybridization reactions, the conditions used to achieve a particular level of stringency will vary, depending on the nature of the nucleic acids being hybridized. For example, the length, degree of complementarity, nucleotide sequence composition (for example, relative GC:AT content), and nucleic acid type, i.e., whether the oligonucleotide or the target nucleic acid sequence is DNA or RNA, can be considered in selecting hybridization conditions. An additional consideration is whether one of the nucleic acids is immobilized, for example, on a filter. Methods for selecting appropriate stringency conditions can be determined empirically or estimated using various formulas, and are well known in the art (see, for example, Sambrook et al., supra, 1989).

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, for example, high stringency conditions, or each of the conditions can be used, for example, for 10 to 15 minutes each, in the order listed above, repeating any or all of the steps listed.

The present invention can include performing more than one assay for detecting LOI of the IGF2 gene or the H19 gene. For example, a method for detecting LOI of the IGF2 gene by detecting hypomethylation of a DMR of the IGF2 gene corresponding to SEQ ID NO:1 can be performed along with detection of hypomethylation of a DMR of the H19 gene corresponding to SEQ ID NO:6, and/or along with methods that analyze expression of alleles that are affected by imprinting to increase the accuracy and/or sensitivity of the assay.

Methods of the present invention in certain aspects, involve analyzing genomic DNA for hypomethylation of a core sequence within SEQ ID NO:1 or within SEQ ID NO:6. Sequences present on a genome, typically the human genome, within the portion of the IGF2 gene corresponding to SEQ ID NO:1, likely will show variable alteration, as found near the H19 and other DMRs in development (Davis, T. L., et al., *Hum. Mol. Genet* 9, 2885-2894 (2000)). In view of the present disclosure, an ordinary artisan can use standard techniques to identify a core sequence within SEQ ID NO:1 for hypomethylation. For example, the amplification product of the amplification reaction disclosed above, can be sequenced with and without bisulfite treatment. An analysis of the sequence will reveal the individual residues that are methylated. As another example, a series of primers can be constructed that selectively hybridize to a series of target sequences within SEQ ID NO:1 or SEQ ID NO:6, in a manner that depends on the methylation state of the target sequence before bisulfite treatment.

The degree of methylation in the DNA associated with the gene or genes for which the presence or absence of LOI is being assessed, may be measured by fluorescent in situ hybridization (FISH) by means of probes which identify and differentiate between genomic DNAs, associated with the gene for which the presence or absence of LOI is being assessed, which exhibit different degrees of DNA methylation. FISH is described in the Human chromosomes: principles and techniques (Editors, Ram S. Verma, Arvind Babu Verma, Ram S.) 2nd ed., New York: McGraw-Hill, 1995, and de Capoa A., Di Leandro M., Grappelli C., Menendez F., Poggesi I., Giancotti P., Marotta, M. R., Spano A., Rocchi M., Archidiacono N., Niveleau A. Computer-assisted analysis of methylation status of individual interphase nuclei in human cultured cells. *Cytometry.* 31:85-92, 1998 which is incorporated herein by reference. In this case, the biological sample will typically be any which contains sufficient whole cells or nuclei to perform short term culture. Usually, the sample will be a tissue sample that contains 10 to 10,000, or, for example, 100 to 10,000, whole somatic cells.

Additionally, as mentioned above, methyl light, methyl heavy, and array-based methylation analysis can be performed, by using bisulfite treated DNA that is then PCR-amplified, against microarrays of oligonucleotide target sequences with the various forms corresponding to unmethylated and methylated DNA.

As mentioned above, methods for detecting LOI can identify altered methylation patterns. However, other methods for detecting LOI are known. For example, certain methods for detecting LOI identify allele-specific gene expression and rely upon the differential transcription of the two alleles. For these methods, RNA is reverse transcribed with reverse transcriptase, and then PCR is performed with PCR primers that span a site within an exon where that site is polymorphic (i.e., normally variable in the population), and this analysis is performed on an individual that is heterozygous (i.e., informative) for the polymorphism. A number of detection schemes can be used to determine whether one or both alleles is expressed. See also, Rainier et al. (1993) *Nature* 362:747-749; which teaches the assessment of allele-specific expression of IGF2 and H19 by reverse transcribing RNA and amplifying cDNA by PCR using new primers that permit a single round rather than nested PCR; Matsuoka et al. (1996) *Proc. Natl. Acad Sci USA* 93:3026-3030 which teaches the identification of a transcribed polymorphism in p57$^{KIP2}$; Thompson et al. (1996) *Cancer Research* 56:5723-5727 which teaches determination of mRNA levels by RPA and RT-PCR analysis of allele-specific expression of p57$^{KIP2}$; and Lee et al. (1997) *Nature Genet.* 15:181185 which teaches RT-PCR SSCP analysis of two polymorphic sites. Such disclosures are herein incorporated by reference. In this case, the biological sample will be any which contains sufficient RNA to permit amplification and subsequent reverse transcription followed by polymerase chain reaction. Typically, the biological sample will be a tissue sample which contains 1 to 10,000,000, 1000 to 10,000,000, or 1,000,000 to 10,000,000, somatic cells.

Quantitative analysis of IGF2 or H19 imprinting status can be performed by Hot-stop PCR on cDNA (Uejima, H., et al., *Nat. Genet.* 25, 375-376 (2000)), as illustrated in the Example section herein. LOI index can be calculated by quantitating the PCR product of a less active allele, or a more active allele, ×100%. LOI can be defined as an LOI index greater than 25 (Cui, H., et al., *Nat. Med.* 4, 1276-1280 (1998)). In certain embodiments, methods of the present invention that analyze LOI are performed in subjects that are informative for either an APA I or CA repeat polymorphism within exon 9 of IGF2 (Cui, H., et al., *Cancer Research* 62, 6442-6 (2002)).

Methods that detect hypomethylation or hypermethylation have the advantage over some other LOI assays in that they are not restricted to subjects with imprinted polymorphisms that have altered transcription levels.

It is also possible to utilize allele specific RNA-associated in situ hybridization (ASISH) to detect the presence or absence of LOI by relying upon the differential transcription of the two alleles. In ASISH, the relative abundance of transcribed mRNA for two alleles is assessed by means of probes which identify and differentiate between the mRNA transcribed from the two alleles. Typically, the probes are tagged with fluorescent labels which results in a high sensitivity and easily quantifiable results. ASISH is described in Adam et al. (1996) "Allele-specific in situ hybridization (ASISH) analysis: a novel technique which resolves differential allelic usage of H19 within the same cell lineage during human placental development," *Development* 122:8347, which is incorporated herein by reference. In this case, the biological sample will typically be any which contains sufficient whole cells or nuclei to perform histological section and in situ hybridization. Usually, the sample will be a tissue sample which contains for example, 10-100,000, or 100-1000, whole somatic cells.

According to the present invention, it is also possible to detect LOI by examining allele-specific post-transcriptional effects (i.e., effects after transcription and before translation), like alternate splicing that depends on which allele was transcribed, and detection of secondary structure of the RNA.

It is also possible, according to the present invention, to detect LOI by examining the relative translation of the two alleles of the gene or genes for which the presence or absence of LOI is being measured. In this case, the presence or relative abundance of the two polypeptides arising from the expression of the two alleles is measured directly. This approach can be effected by any known technique for detecting or quantifying the presence of a polypeptide in a biological sample. For example, allele-specific translational effects may be examined by quantifying the proteins expressed by the two alleles using antibodies specific for each allele (transcribed, translated polymorphism). Such effects may be measured and/or detected by such analytical techniques as Western blotting, or use of an ELISA assay. In this case, the biological sample will be any which contains a sufficient amount of the polypeptide(s) encoded by the gene(s) for which the presence or absence of LOI is being measured.

LOI may also be detected by examining post-translational effects, such as secondary modifications that are specific to one allele, like glycosylation or phosphorylation. For example, one allele may be modified, say by phosphorylation or glycosylation, and the other one not. Because the polymorphism encodes a recognition motif, then one can readily distinguish the difference by a Western blot, detecting alternate migration of the polypeptide or protein; use of antibodies specific for the modified form; radioactive incorporation of phosphoryl group or glycosyl group or other modification (i.e., in living cells, followed by the detection of a band at a varying location).

LOI may also be detected by reliance on other allele-specific downstream effects. For example, depending on the metabolic pathway in which lies the product of the imprinted gene; the difference will be 2× versus 1× (or some number in between) of the product, and therefore the function or a variation in function specific to one of the alleles. For example, for IGF2, increased mitogenic signaling at the IGF1 receptor, increased occupancy of the IGF1 receptor, increased activity at the IGF2 catabolic receptor, decreased apoptosis due to the dose of IGF2; for KvLQT1, change in the length of the QT interval depending on the amount and isoform of protein, or change in electrical potential, or change in activity when the RNA is extracted and introduced into *Xenopus* oocytes.

It is also possible to detect LOI by detecting an associated haplotype, i.e., linked polymorphisms that identify subjects whose genes are prone to LOI.

LOI can be detected by relying on a polymorphism, i.e., a genetic difference between the two alleles. However, it will be recognized that many of the techniques described above may be used to detect LOI even when there is no polymorphism in the two alleles of the gene or genes for which the presence or absence of LOI is being measured. For example, LOI may be detected by reliance on allele-specific DNA methylation (polymorphism independent); histone acetylation; other modifications to DNA; or alterations in replication timing, when the imprinted allele shows "replication timing asynchrony" i.e. the two alleles replicate at different times. When the two alleles replicate at the same time, LOI may be detected by FISH. Since imprinted alleles pair in the late S phase, LOI may be detected by the absence of such pairing in the late S as observed by FISH.

On the other hand certain techniques are more conveniently used when there is a polymorphism in the two alleles of the gene or genes for which the presence or absence of LOI is being measured. For example, RT-PCR followed by SSCP (single strand conformational polymorphism) analysis; restriction enzyme digestion analysis followed by electrophoresis or Southern hybridization; or radioisotopic PCR; PCR; allele-specific oligonucleotide hybridization; direct sequencing manually or with an automated sequencer; denaturing gradient gel electrophoresis (DGGE); and many other analytical techniques can be used to detect LOI when relying on a polymorphism.

In another embodiment of the present invention the method involves measuring the degree of LOI such as by measuring the degree of hypomethylation of a DMR for a particular gene or set of genes. In certain embodiments, the method includes measuring the degree of hypomethylation of the DMR of IGF2 gene corresponding to SEQ ID NO:1 or a polymorphism thereof, or a fragment thereof. In another embodiment, the method includes measuring the degree of hypomethylation of the DMR of the H19 gene corresponding to SEQ ID NO:6 or a polymorphism thereof, or a fragment thereof.

As used herein, when hypomethylation is measured, "the degree of LOI" means the percentage of methylation compared to a fully methylated DMR. As used herein, when expression of different polymorphisms is compared, "the degree of LOI" means total expression (as measured by actual expression or transcription) attributable to the allele which is normally imprinted. The degree of LOI may be calculated by allele ratio, i.e., the more abundant allele divided by the less abundant allele. The degree of LOI may be determined by any method which allows the determination of the relative expressions of the two alleles. For example, a degree of LOI of 100% reflects complete LOI (equal expression of both alleles), while a degree of LOI of 0% reflects no LOI (expression of only one allele). Any method of measuring the relative expression of the two alleles is considered to be included in the present invention.

The degree of LOI can be measured for the IGF2 gene or the H19 gene when screening for the presence of colorectal cancer, or other cancers, e.g., the degree of LOI is measured for the IFG2 gene or the H19 gene when screening for the presence of stomach cancer, esophageal cancer, or leukemia.

The degree of LOI can be measured by measuring the degree of hypomethylation of the DMR of IGF2 or the DMR of H19 or a fragment thereof, or a polymorphism thereof, in a blood sample, for example a PBL sample, wherein a high degree of hypomethylation is indicative of an increased risk for cancer. For example, a series of genomic clones can be analyzed that are derived from the subject. These clones can be analyzed for hypomethylation of the DMR of IGF2 or the DMR of H19. The degree of hypomethylation can be determined by identifying the methylation frequency of possibly methylated sites. Possible methylated sites are cytosine residues that are typically methylated in a subject, but become unmethylated in certain subjects that are at an increased risk of developing cancer. For example, residues corresponding to positions 87, 90, and 106 of SEQ ID NO:1. If uracil is present after bisulfite treatment, then the residue is unmethylated. Hypomethylation is present when in a series of clones of genomic DNA, there is a measurable decrease in methylation, such as a measurable decrease in methylation of positions 87, 90, and 106 of SEQ ID NO:1.

A linear detection platform can be employed to quantitate LOI. A linear detection platform is a detection platform that allows quantitation because the amount of target present and signal detected are linearly related. In this regard, a PhosphorImager (model 445SI, manufactured by Molecular Dynamics), which detects radioactive emissions directly from a gel, can be used. Other linear detection systems include carefully titrated autoradiography followed by image analysis, beta-emission detection analysis (Betascan). Another linear detection platform is an automated DNA sequencer such as ABI 377 analyzer. Another linear detection platform is an array based system with appropriate software. Another is SNuPE.

In addition to measuring the degree of imprinting when an imprinted polymorphism is present in a gene, it is possible to assess the degree of LOI in a particular gene even when an imprinted polymorphism is not present in that gene. For example, imprinting can be assessed by the degree of methylation of CpG islands in or near an imprinted gene (e.g., Barletta, Cancer Research, op. cit). In addition, imprinting can be assessed by changes in DNA replication timing asynchrony, e.g. White L M, Rogan P K, Nicholls R D, Wu B L, Korf B. Knoll J H, Allele-specific replication of 15q11-q 13 loci: a diagnostic test for detection of uniparental disomy. *American Journal of Human Genetics.* 59:423-30, 1996.

On the other hand, certain techniques are more conveniently used when there is a polymorphism in the two alleles of the gene or genes for which the presence or absence of LOI is being measured. For example, RT-PCR, followed by gel electrophoresis to distinguish length polymorphisms, or RT-PCR followed by restriction enzyme digestion, or by automated DNA sequencing, or by single strand conformational polymorphism (SSCP) analysis, or denaturing gradient gel electrophoresis, etc.; or, completely DNA based methods that exploit, for example DNA methylation, which require no RT step, to convert RNA to cDNA prior to PCR).

Once the degree of LOI, such as the level of hypomethylation, has been measured for the gene or genes in question, the risk of having cancer is then assessed by comparing the degree of LOI for that gene or genes to a known relationship between the degree of LOI and the probability of the presence of the particular type of cancer or other disease. The relationship between the degree of LOI and the probability of the presence of a particular type of cancer may be determined for any combination of a normally imprinted gene or genes and a particular type of cancer by determining.

When the degree of LOI is measured, such as the degree of IGF2 hypomethylation, the measured degree of LOI is compared to a known relationship between the degree of LOI and the probability of contracting the particular type of cancer. The relationship between the degree of LOI and the probability of contracting a particular type of cancer may be determined by one of ordinary skill in the art for any combination of a normally imprinted gene or genes and a particular type of cancer by determining the degree of LOI in a statistically meaningful number of tissue samples obtained from patients with cancer, and determining the degree of LOI in a statistically meaningful number of tissue samples obtained from patients without cancer, and then calculating an odds ratio as a function of the degree of LOI.

It should also be understood that measuring the degree of LOI, can be carried out by comparing the degree of LOI against one or more predetermined threshold values, such that, if the degree of LOI is below a given threshold value, which can be manifested in a regular methylation pattern, then the subject is assigned to a low risk population for having cancer, contracting cancer, and/or having replication error repair defects. Alternatively, the analytical technique may be designed not to yield an explicit numerical value for the degree of LOI, but instead yield only a first type of signal when the degree of LOI is below a threshold value and/or a second type of signal when the degree of LOI is below a threshold value. It is also possible to carry out the present methods by means of a test in which the degree of LOI is signaled by means of a non-numeric spectrum such as a range of colors encountered with litmus paper.

Example 2 reveals a possible mechanism wherein hypomethylation of the DMR of IGF2 results in loss of imprinting of the IGF2 gene. By this mechanism, methylation of the DMR of IGF2 recruits repressors to the IGF2 gene. Accordingly, in another embodiment, the present invention provides a method for identifying a repressor of IGF2, or a factor that represses IGF2 imprinting, by identifying a factor that preferentially binds to the methylated versus the non-methylated DMR of IGF2. In this embodiment, virtually any method for identifying factors, especially protein factors, that bind methylated nucleic acids and/or affect gene expression can be included. Many such methods are known in the art.

For example, a protein preparation can be contacted with an IGF2 DMR or fragment thereof, and binding of a protein of the protein preparation to the IGF2 DMR can be detected. A protein that binds the IGF2 DMR or fragment thereof, can then be analyzed for the ability to repress expression of IGF2, for example using a co-transfection assay, that includes a polynucleotide that includes the IGF2 DMR or fragment thereof, operably linked to a reporter gene, and a polynucleotide encoding the IGF2 DMR-binding protein. Expression of the reporter gene can be analyzed and compared to control experiments that do not include the IGF2 DMR binding protein. Furthermore, the results can be compared in cells with methylated IGF2 DMR and cells with hypomethylated IGF2 DMR, for example DNA methyltransferase knockout cells (See Example 2). The method provides for the identification of IGF2 repressors that preferentially bind methylated IGF2 DMR.

Binding of a protein to the IGF2 DMR or a fragment thereof, can be detected, for example, using an electrophoretic mobility shift assay (EMSA). A protein preparation such as a nuclear extract can be prepared (See e.g., Dignam et al., *Nucl. Acids Res.* 11;1475-1489 (1983)). EMSAs can be performed as described previously (Latinkic and Lau, *J. Biol. Chem.* 269:23163-23170 (1994)); Wang et al., *Cell* 87:697-708 (1996)). In assays where unlabeled oligonucleotides (10-fold or 100-fold molar excess) or antibodies directed against known transcription factors are used, these reagents are typically added to the binding reaction prior to the addition of nuclear extract. The antibodies used in most experiments can be selected based on their ability not to interfere with the factor binding to DNA. Factors that specifically bind the DMR of IGF2 when it is methylated can be identified by comparing mobility shift patterns using methylated and hypomethylated IGF2 DMR of SEQ ID NO:1, or fragments thereof.

The term "nucleic acid molecule" is used broadly herein to mean a sequence of deoxyribonucleotides or ribonucleotides that are linked together by a phosphodiester bond. As such, the term "nucleic acid molecule" is meant to include DNA and RNA, which can be single stranded or double stranded, as well as DNA/RNA hybrids. Furthermore, the term "nucleic acid molecule" as used herein includes naturally occurring nucleic acid molecules, which can be isolated from a cell, for example, the IGF-2 gene, as well as synthetic molecules, which can be prepared, for example, by methods of chemical synthesis or by enzymatic methods such as by the polymerase chain reaction (PCR), and, in various embodiments, can contain nucleotide analogs or a backbone bond other than a phosphodiester bond.

The terms "polynucleotide" and "oligonucleotide" also are used herein to refer to nucleic acid molecules. Although no specific distinction from each other or from "nucleic acid molecule" is intended by the use of these terms, the term "polynucleotide" is used generally in reference to a nucleic acid molecule that encodes a polypeptide, or a peptide portion thereof, whereas the term "oligonucleotide" is used generally in reference to a nucleotide sequence useful as a probe, a PCR primer, an antisense molecule, or the like. Thus, a polynucleotide of the invention can encode, for example SEQ ID NO:1, whereas an oligonucleotide of the invention can be used as a probe to detect SEQ ID NO:1. Of course, it will be recognized that an "oligonucleotide" also can encode a peptide. As such, the different terms are used primarily for convenience of discussion.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template In another aspect, the present invention includes kits that are useful for carrying out the methods of the present invention. The components contained in the kit depend on a number of factors, including: the condition, state, or phenomenon relied on to detect LOI or measure the degree of LOI, the particular analytical technique used to detect LOI or measure the degree of LOI, and the gene or genes for which LOI is being detected or the degree of LOI is being measured.

Accordingly, the present invention provides a kit for determining a methylation status of a differentially methylated region (DMR) of IGF2 corresponding to SEQ ID NO:1 or a fragment or a polymorphism thereof, or of a DMR of H19 corresponding to SEQ ID NO:6 or a fragment or a polymorphism thereof. The kit includes an oligonucleotide probe, primer, or primer pair, or combination thereof for carrying out a method for detecting hypomethylation, as discussed above. For example, the probe, primer, or primer pair, can be capable of selectively hybridizing to the DMR either with or without prior bisulfite treatment of the DMR. The kit can further include one or more detectable labels.

The kit can also include a plurality of oligonucleotide probes, primers, or primer pairs, or combinations thereof, capable of selectively hybridizing to the DMR with or without prior bisulfite treatment of the DMR. The kit can include an oligonucleotide primer pair that hybridizes under stringent conditions to all or a portion of the DMR only after bisulfite treatment. For example, the kit can include the primer pairs of SEQ ID NOS:2-34 The kit can include instructions on using kit components to identify an increased risk of developing cancer. In certain embodiments the instructions relate to subjects of the general population. The kit for example, includes one or both of a primer pair corresponding to the primer pair SEQ ID NO:23 and SEQ ID NO:24 and the primer pair SEQ ID NO: 25 and SEQ ID NO:26. In another aspect, the kit for example, includes one or both of a primer pair corresponding to the primer pair SEQ ID NO:27 and SEQ ID NO:28, and the primer pair SEQ ID NO: 29 and SEQ ID NO:30.

When LOI is detected by relying on the degree of methylation of the genomic DNA associated with the gene(s) for which LOI is being detected or the degree of LOI is being measured using FISH, the kit will typically contain one or more probes which can identify a specific imprinted gene or group of genes. Typically, such probes will be nucleic acids or monoclonal antibodies and will be linked to, for example, a fluorescent label.

In the case of detecting LOI by relying on the differential rates of transcription of two polymorphic alleles, the kit can include:

(i) means for the amplification of the mRNAs corresponding to the two polymorphic alleles of the gene in question. Examples of such means include suitable DNA primers for the PCR amplification of the mRNAs corresponding to the two polymorphic alleles of the gene in question. Specific examples of such means include any pair of DNA primers which will anneal to and amplify any gene which is normally imprinted and in which a polymorphism is present.

According to the present invention, the kit may further include:

(ii) means for identifying the products of the amplification of the mRNAs corresponding to the two polymorphic alleles of the gene in question. Such means include, but are not limited to, a restriction enzyme which specifically cleaves one of the products of the amplification of the mRNAs corresponding to the two polymorphic alleles of the gene in question. Specific examples of such enzymes include, but are not limited to, Apa I in the case of the IGF2 gene.

When the degree of LOI is measured by relying on the differential rates of transcription of two polymorphic alleles, the kit may comprise:

(i) means for the linear amplification of the mRNAs corresponding to the two polymorphic alleles of the gene in question. Examples of such means include a sufficient quantity of suitable DNA primers for the PCR amplification of the mRNAs corresponding to the two polymorphic alleles of the gene in question, such that the PCR amplification may be carried out without exhausting the primers and linear amplification achieved. Specific examples of such means includes any pair primers for any gene which is normally imprinted. According to the present invention, the kit can further include:

(ii) means for identifying the products of the amplification of the mRNAs corresponding to the two polymorphic alleles of the gene in question. Such means include a restriction enzyme which specifically cleaves one of the products of the amplification of the mRNAs corresponding to the two polymorphic alleles of the gene in question.

When detecting LOI or measuring the degree of LOI by ASISH, the kit will typically contain one or more probes which can identify and distinguish between the RNA associated with the two alleles. Typically, such probes will be nucleic acids that are specific for each allele, and are used either sequentially or together using different fluorescent labels for each allele.

When detecting LOI or measuring the degree of LOI by assessing the relative translation of two alleles, the kit may contain antibodies that distinguish the protein product of the two alleles.

The following example is intended to illustrate but not limit the invention.

EXAMPLE 1

Association of Loss of Imprinting and Colorectal Neoplasia

This example illustrates that LOI in normal tissue is associated with either a family history or personal history of colorectal neoplasia.

Materials & Methods

Study population. Subjects were identified and recruited in the Johns Hopkins Outpatient Endoscopy Clinic and the Johns Hopkins Greenspring Endoscopy Unit. Eligible subject were those individuals who were having a colonoscopy for any medical indication, who were 18 years of age or older and who had physician approval. Written informed consent was obtained from all subjects. Clinical, demographic, family history and exposure information were obtained with the use of validated questionnaires. The protocol was approved by the Johns Hopkins Joint Committee on Clinical Investigation.

Collection of research materials. Colon tissues were collected from patients who underwent a colonoscopy. Ninety-seven percent of patients agreed to participate. Colonoscopic examinations were performed with a standard Olympus colonoscope by several endoscopists. Up to 8 mucosal punch biopsies were obtained from proximal and distal colon using routine biopsy forceps. The tissues were immediately frozen in liquid nitrogen and stored at −135° C. Lymphocytes were separated from blood (20 ml) from every patient with Accuspin tubes (Sigma/Aldrich, St. Louis, Mo.) using Ficoll-Paque Plus (Amersham Pharmacia Biotech, Pisacataway, N.J.) and centrifuged at 400 g at room temperature for 30 minutes. The lymphocyte layer was collected and washed once with PBS.

The isolated lymphocyte pellets were immediately stored at −135° C. until the assays were performed.

DNA and RNA preparation. DNA extraction was performed as previously described (Cui, H., et al., *Nat. Med.* 4, 1276-1280 (1998), incorporated in its entirety herein by reference). RNA was extracted from frozen mucosal punch biopsies and lymphocytes with the RNeasy Mini Kit (Qiagen, Valencia, Calif.) shortly before RT. Each RNA sample was quantified by spectrophotometry and agarose gel electrophoresis, treated with 10 u RNase inhibitor (Invitrogen, Carlsbad, Calif.) and used immediately.

Quantitative analysis of IGF2 imprinting status. Reverse transcription was performed with freshly extracted RNA samples, which had been treated with DNase I to remove any DNA contamination as previously described (Cui, H., et al., *Nat. Med.* 4, 1276-1280 (1998)). Quantitative analysis of IGF2 imprinting status was performed by Hot-stop PCR (Uejima, H., et al., *Nat. Genet.* 25, 375-376 (2000), incorporated herein in its entirety, by reference). All reactions were done in duplicate with presence and absence of reverse transcriptase on identical RNA sample to exclude any possibility of DNA contamination.

Detection of DNA Methylation. The IGF2 DMR is located on positions −566 to −311 relative to IGF2 exon 3 (corresponding to positions 661 to 916 of GenBank accession no. Y13633). Analysis of methylation was performed by bisulfite genomic sequencing by analyzing positions 87, 90, and 106 of the IFG2 DMR (SEQ ID NO:1). Genomic DNA was treated with bisulfite, as follows: Sodium hydroxide was added to genomic DNA to a final concentration of 0.3M and incubated at 37° C. for 20 min to denature the genomic DNA. A sodium metabisulfite solution is added to the denatured DNA to a concentration of about 2M sodium metabisulfite (EM Sience) and 10 mM hydroquinone (EM Science), pH 7.0, and the DNA in the sodium metabisulfite solution is incubated at 55° C. in the dark for about 12-16 hrs. Treated DNA was purified with the QIAquick PCR purification kit according manufacturer's protocol. The purified DNA was exposed to about 1/10 volume of 3M NaOH and incubated at 37° C. for 20 min. Five molar $NH_4OAC$ to a final 3M concentration and kept at room temperature for 5 min to neutralize DNA. Five µg yeast RNA and 3× volume of pure ethanol and were added to the neutralized DNA, and the solutions were kept at −80° C. for 30 min and then centrifuged to precipitate DNA. The DNA was then washed with 70% ethanol, dissolved in TE (pH 7.2). and stored at −20° C. for PCR.0

PCR was performed as follows: Treated DNA was amplified by PCR, using primers 5'-GGTGAG-GATGGGTTTTTGTT-3' (SEQ ID NO:2) and 5'-CTACTCTCCCAACCTCCCTAA-3' (SEQ ID NO:3), annealing at 55° C., followed by nested PCR using primers 5'-ATTGGGGGTGGAGGGTGTAT-3' (SEQ ID NO:4) and 5'-TCTATTACACCCTAAACCCAA-3' (SEQ ID NO:5), annealing at 52° C.

PCR products were purified on 2% agarose gels for direct sequencing as described above. The annealing temperature was 55° C. For sequencing individual clones, the PCR products were subcloned into a TA Cloning vector (Invitrogen, Carlsbad, Calif.) according to the manufacturer's instructions, and 15-20 clones were selected for sequencing.

All of the PCR products were purified using the QIAEX II gel extraction kit (Qiagen) and directly sequenced with an ABI Prism 377 DNA sequencer using the BigDye Terminator Cycle Sequencing kit following the manufacturer's protocol (PE Applied Biosystems, Foster City, Calif.) (See Cui et al., 61:4947 (2001), incorporated herein in its entirety, by reference.

Statistical Analysis. Hypothesis testing was performed with a combination of chi-square and Fisher exact t-tests as appropriate. Multiple logistic regression models were constructed for the association of the independent covariates with LOI, and for the association of LOI with colorectal neoplasia and family history of cancer. Kappa statistics was used to determine agreement beyond chance. Statistical analysis was performed using STATA 7.0 software (Stata Corp.).

Results

To ensure complete ascertainment of colorectal neoplasia, a cross-sectional analysis was performed of patients who provided clinical and family history information. Contemporaneous colonoscopic examination was performed with mucosal biopsy. For logistical purposes, patients were chosen that were selected for colonoscopic examination for clinical indications. For this reason, there was modest enrichment for a past history of colonic adenoma or cancer (13%, compared to 10% in the general U.S. population of this age).

Four hundred and twenty one patients agreed to participate between 1999 and 2001. 191 patients were informative for either an APA I or CA repeat polymorphism within exon 9 of IGF2 allowing analysis of imprinting status. In addition to both proximal and distal colonic mucosal specimens, PBL for RNA and DNA analysis, a family and personal history of neoplasia, environmental exposures, medications, and dietary information was obtained.

First the relationship between LOI and age was examined. It has been suggested previously that altered IGF2 methylation is age-related, suggesting that epigenetic abnormalities are acquired over time (Issa, J. P., et al., *Proc. Natl. Acad. Sci. U.S.A.* 93, 11757-11762 (1996)). However, no relationship between LOI in PBL and age was found (Table 1). There were also no significant differences by sex or race (Table 1). Next the relationship between LOI and family history was analyzed. The odds of LOI in PBL were 4.4 times greater in patients with a positive family history of CRC compared to their counterparts with a negative family history (p=0.003; Table 1).

The relationship between LOI and colorectal neoplasia in the patient was next evaluated. The odds of LOI in PBL were 4.4 times greater in patients with past or present colorectal neoplasia (adenomatous polyps or cancer) than their counterparts without neoplasia (p=0.002; Table 1), indicating a strong association between LOI and colorectal neoplasia. Even when patients with a positive family history were excluded from the analysis, the odds of LOI in PBL these odds were 4.7 times greater (95% CI 1.29-17.3, p=0.01).

The accepted model for colorectal carcinogenesis is that cancers progress from adenomas (E. R. Fearon and B. Vogelstein, *Cell* 61, 759-767 (1990)). Consequently when stratified, the odds of LOI in PBL were 4.1 times greater in patients with past or present adenomas but no CRC, compared to patients with no past or present neoplasia (p=0.016; Table 1), and they were 34.4-fold greater in patients with past or present CRC than in those without colorectal neoplasia (p<0.0001; Table 1). These data strongly suggest that LOI is associated with both initiation and progression of colorectal neoplasia.

TABLE 1

Association of loss of imprinting (LOI) of IGF2 in peripheral blood lymphocytes with family history of colon cancer and with present or past colonic neoplasia in the patient.

|  | Imprinting | | Unadjusted odds ratio | | | Adjusted odds ratio* | | |
|---|---|---|---|---|---|---|---|---|
|  | Normal | LOI | | | | | | |
|  | N (%) | N (%) | P valve | OR | 95% CI | P valve | OR | 95% CI |
| Age (±SD) | 58.7 ± 12.8 | 59.9 ± 9.7 | 0.64 | 1.00 | 0.97-1.04 | 0.35 | 1.02 | 0.97-1.07 |
| Sex | | | | | | | | |
| Women | 72 (85.7) | 12 (14.3) | | | | | | |
| Men | 75 (86.2) | 12 (13.8) | 0.93 | 0.96 | 0.41-2.28 | 0.70 | 1.21 | 0.45-3.23 |
| Race | | | | | | | | |
| White | 129 (86.0) | 21 (14.0) | | | | | | |
| Black | 18 (85.7) | 3 (14.3) | 0.97 | 1.02 | 0.28-3.78 | 0.55 | 0.62 | 0.13-2.96 |
| Family history | | | | | | | | |
| No | 111 (91.0) | 11 (9.0) | | | | | | |
| Yes | 36 (73.4) | 13 (26.5) | 0.003 | 3.64 | 1.5-8.84 | 0.004 | 4.41 | 1.62-12.0 |
| Colonic Neoplasia | | | | | | | | |
| No | 99 (93.4) | 7 (6.6) | | | | | | |
| Yes | 48 (73.8) | 17 (26.2) | 0.001 | 5.01 | 1.94-12.89 | 0.002 | 4.37 | 1.74-11.0 |
| Adenomas | 44 (78.6) | 12 (21.4) | 0.008 | 3.85 | 1.42-10.5 | 0.016 | 4.10 | 1.30-12.8 |
| CRC | 4 (44.4) | 5 (55.6) | <0.0001 | 17.67 | 3.85-81.0 | <0.0001 | 34.4 | 6.10-194 |

*Hypothesis testing performed with multiple logistic regression adjusted for age, gender, race, family history, and physical activity; OR, odds ratio; 95% CI, 95% confidence interval The relationship between LOI in PBL and LOI in the colon was determined in patients from whom informative samples sufficient for imprinting analysis could be obtained in both tissues. All of the patients with LOI in PBL also showed LOI in normal colon (Table 2 and data not shown). In the remainder LOI was limited to the colon (Table 2), and in these patients it was present variably in proximal or distal colonic mucosa (data not shown). Thus, LOI either was a generalized defect affecting both blood and colon, or a focal abnormality within one or more samples within the colon. In the latter group, no statistically significant association with family or personal history of colorectal neoplasia was found.

TABLE 2

Concordance of imprinting status between colonic mucosa and blood*

|  | Colon | |
|---|---|---|
| Blood | Normal | LOI |
| Normal | 123 | 21 |
| LOI | 0 | 24 |

*Kappa statistic 88.0%, p value < 0.0001

It was next determined whether a method of the present invention can be performed using DNA rather than RNA. SEQ ID NO:1 provides a differentially methylated region (DMR) within IGF2 that shows hypomethylation in CRC with LOI (Cui H. et al., Cancer Res. 62, 6442-6446 (2002), incorporated herein in its entirety by reference). In order to determine whether a hypomethylation defect occurs in PBL and colon of patients without known neoplasia, we examined 24 samples, 12 from normal tissues (6 PBL, 6 matched normal colonic mucosa) with normal imprinting, and 12 from normal tissues (6 PBL, 6 matched normal colonic mucosa) with LOI. In all 12 tissues with normal imprinting, IGF2 showed a normal pattern of half-methylation (FIG. 2A). In contrast, in 11 of 12 samples from normal tissue with LOI, IGF2 showed hypomethylation of the IGF2 DMR; in the other sample, IGF2 showed partial methylation of both alleles but was nevertheless abnormal (FIG. 5B). The significance of hypomethylation between normal tissues with and without LOI was p<0.0001 (Fisher's exact test). In contrast, H19 showed hypomethylation in all cases, regardless of imprinting status (data not shown). Thus, aberrant IGF2 methylation is linked to LOI in normal colon and lymphocytes, just as it is in CRC.

In summary, a strong and significant association of LOI with family history, and with present or past personal history of colorectal neoplasia was identified using methods of the present invention. When present in PBL, LOI appears to be a systemic abnormality, since it was always also present in both proximal and distal colon. It cannot be concluded currently that the abnormality is present in the germline, as it is epigenetic and might be acquired postnatally. This abnormality is common, present in 14% of the patients studied, which by design may be mildly enriched for CRC. Nevertheless, a 10% frequency of LOI in PBL in the general population has previously been observed (Cui, H., et al., Nat. Med. 4, 1276-1280 (1998); Sakatani, T., et al., Biochem. Biophys. Res. Commun. 283, 1124-1130 (2001)).

This epigenetic abnormality was present at both the RNA and DNA level. Eleven of 12 tissues with LOI showed hypomethylation of IGF2, and all 12 tissues with normal imprinting showed normal methylation of IGF2. The methylation assay may be improved, as the entire IGF2 DMR has not yet been examined by bisulfite sequencing. There may be a critical core sequence involved, with nearby sequences showing variable alteration, as found near the H19 and other DMRs in development (Davis, T. L., et al., Hum. Mol. Genet 9, 2885-2894 (2000)).

The odds ratio for colorectal cancer of LOI (34.4) is higher than seen for mutation of the mismatch repair genes in HNPCC(H. T. Lynch and J. F. Lynch, Semin. Surg. Oncol. 18, 305-313 (2000)), which confers an 80% lifetime risk of CRC (H. T. Lynch and A. de la Chapelle, J. Med. Genet. 36, 801-818 (1999)). In contrast, the I1307K mutation of APC confers only a two-fold increased risk of colorectal cancer (Laken S. J., et al., *Nat. Genet.* 17, 79-83 (1997)). Furthermore, the prevalence of LOI, 10%, is at least 10-fold higher than all known CRC-predisposing genetic mutations in the population combined (Samowitz, W. S., et al., *Gastroenterology* 121, 830-838 (2001); and Percesepe, A., et al., *J. Clin. Oncol.* 19, 3944-3950 (2001)). Consequently, conventional genetic mutation screening for cancer risk has been targeted at defined populations with a strong family history, and not for screening and surveillance in the general population. In contrast an LOI blood test might be of value for population screening.

EXAMPLE 2

Loss of Imprinting in Colorectal Cancer Linked to Hypomethylation of H19 and IGF2

This example illustrates that loss of imprinting of IGF2 in colorectal cancer is correlated with hypomethylation of the DMR of IGF2, and in at least some colorectal cancer patients with hypomethylation of the DMR of H19 as well. Furthermore, the example reveals a model of gene regulation based on hypomethylation of the DMR of IGF2.

Materials and Methods

Bisulfite Sequencing Analysis. H19 CTCF binding site 1 (CBS1) was analyzed as described earlier (H. Cui et al, Cancer Res., 61: 4947-4950, 2001); CBS6 corresponds to GenBank nucleotides 7855-8192 (accession no. AF125183) and was analyzed after bisulfite treatment using primers 5'-GAGTTTGGGGGTTTTTGTATAGTAT-3' (SEQ ID NO:23) and 5'-CTTAAATCCCAAACCATAACACTA-3' (SEQ ID NO:24), followed by 5'-GTATATGGG-TATTTTTTGGAGGT-3' (SEQ ID NO:25) and 5'-CCATAA-CACTAAAACCCTCAA-3' (SEQ ID NO:26), both annealing at 55° C.

The IGF2 DMR sequence analyzed corresponds to GenBank nucleotides 631-859 (accession no. Y13633), and was analyzed after bisulfite treatment using primers 5'-GGGAAT-GTTTATTTATGTATGAAG-3' (SEQ ID NO:27) and 5'-TAAAAACCTCCTCCACCTCC-3' (SEQ ID NO:28), annealing at 55° C., followed by 5'-TAATTTATT-TAGGGTGGTGTT-3' (SEQ ID NO:29) and 5'-TCCAAA-CACCCCCACCTTAA-3' (SEQ ID NO:30), annealing at 50° C. Other conditions are as described earlier (H. Cui et al, Cancer Res., 61: 4947-4950, 2001).

Methyltransferase Activity Analysis. In vitro functional analysis was performed using the 293/EBNA1 cell line as described (Mol. Cell. Biol., 14: 5487-5494, 1994) and the pcDNA3Myc vector containing full-length DNMT3B coding sequences, and p220.2 (Mol. Cell. Biol., 7: 379-387, 1987) as the assay plasmid. Cotransfected target DNA was digested with the methylation-sensitive restriction endonuclease HpaII, and Southern blot was performed using p220.2 as a probe. All of the transfections were done in duplicate or triplicate for each experiment.

Analysis of DNTM3B Sequence and IGF2 Imprinting. Direct PCR sequencing of genomic DNA was performed to analyze the sequence of DNMT3B. All of the coding exons published including exon-intron junctions were thoroughly examined. LOI of IGF2 was assessed according to hot-stop PCR(H. Uejima et al, Nat. Genet., 25: 375-376, 2000).

Results

Figure 4:
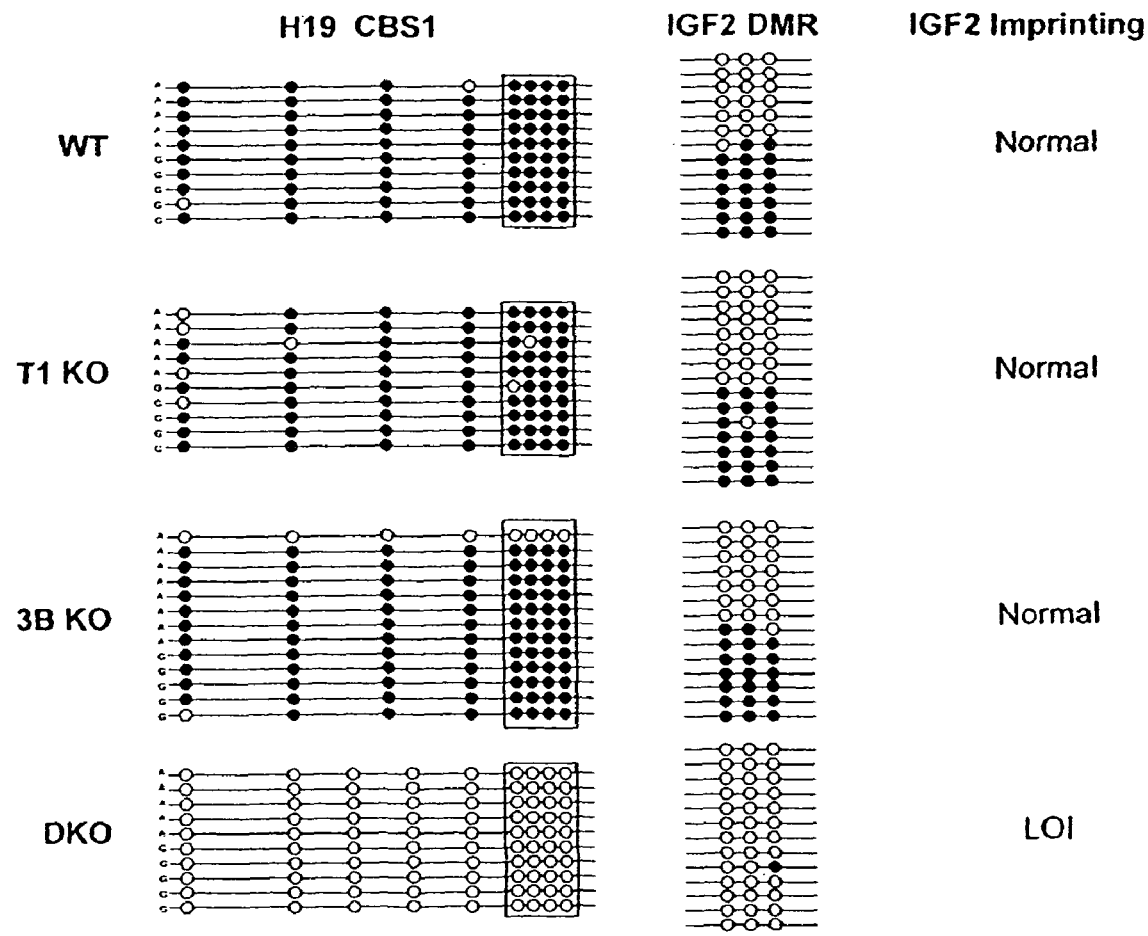
FIG. 4 shows hypomethylation of H19 and IGF2 DMRs in CRC cell lines with LOI of IGF2 and somatic cell knockout of DNA methyltransferase. HCT116 cells (WT), DNMT1 knockout (T1KO), DNMT3B knockout (3BKO), and DNMT1/DNMT3B double-knockout (DKO) cells were analyzed by bisulfite genomic sequencing at the H19 (CTCF binding site 1) and IGF2 DMRs. By the enhancer competition model, biallelic methylation of the H19 DMR should cause LOI of IGF2, but it does not in these cells. Rather, the IGF2 DMR shows normal half methylation with normal imprinting and hypomethylation with LOI of IGF2.

Hypomethylation of H19 and IGF2 DMRs in DNA Methyltransferase Knockout Cell Lines. HCT116 cells show normal imprinting but undergo LOI of IGF2 after somatic cell knockout of both DNMT1 and DNMT3B (I. Rhee et al, Nature (Lond.), 416: 552-556, 2002). To test whether loss of methylation rather than the gain of methylation is responsible for LOI in these cells, we examined directly the methylation of two DMRs that distinguish parental alleles in human cells: the H19 DMR 5-kb upstream of H19 and methylated on the paternal allele (H19 active, IGF2 silent); and the IGF2 DMR within intron 2 of IGF2 and methylated on the maternal allele (M. J. Sullivan et al, Ref. *Oncogene,* 18: 7527-7534, 1999). Note that the DMRs in humans differ from the mouse, in which there are three rather than one DMR within IGF2 (H. Nakagawa et al, Proc. Natl. Acad. Sci. USA, 98: 591-596, 2001). Bisulfite sequencing analysis of HCT116 cells, and HCT116 cells lacking DNMT1, DNMT3B, or both, revealed that in the double-knockout cells, which showed LOI, both the H19 and IGF2 DMRs were extensively hypomethylated (FIG. 4). This hypomethylation was found in three separate double-knockout lines with LOI and in none of single-knockout or wild-type lines with normal imprinting (Table 3).

TABLE 3

IGF2 imprinting status and methylation alterations in DNMT knockout cell lines

| | | Methylation Status | |
|---|---|---|---|
| Cell Lines | IGF2 LOI | H19 CBS1 | IGF2 DMR |
| WT[1] | No | Hyper | Half |
| T1KO-1 | No | Hyper | Half |
| T1KO-2 | No | Hyper | Half |
| 3BKO-1 | No | Hyper | Half |
| 3BKO-2 | No | Hyper | Half |
| DKO-1 | Yes | Hypo | Hypo |
| DKO-2 | Yes | Hypo | Hypo |
| DKO-3 | Yes | Hypo | Hypo |

[1]WT, HCT116 wild-type; T1KO, DNMT1 knockout; 3BKO, DNMT3B knockout; DKO, double-knockout; Half, normal half-methylation; Hypo, hypomethylation; Hyper, hypermethylation.

Figure 5:
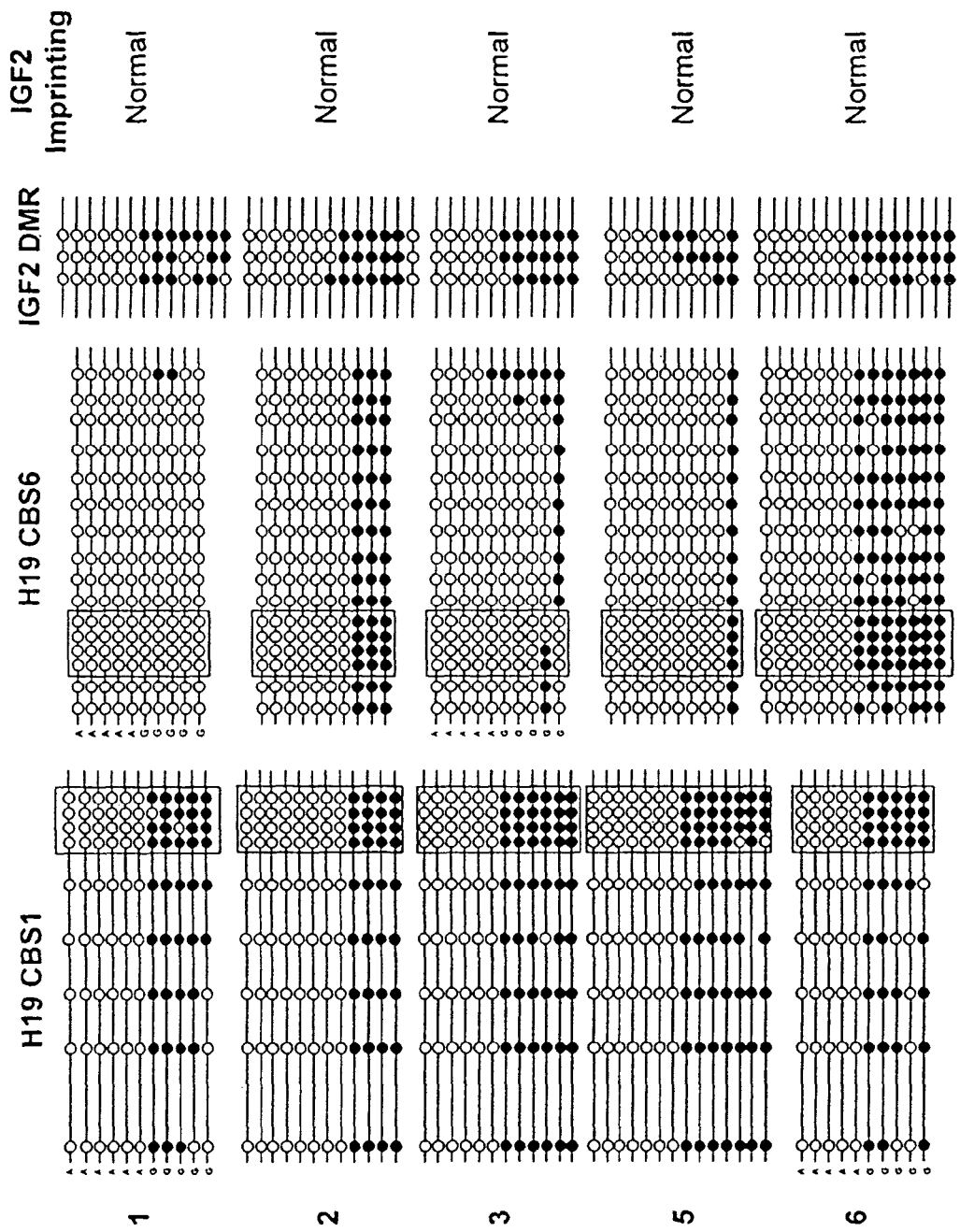
FIG. 5 shows normal methylation of IGF2 and variable methylation of H19 DMRs in sporadic CRCs with normal imprinting of IGF2. The H19 DMR shows a general trend of normal methylation and normal imprinting status of IGF2, whereas the IGF2 DMR shows complete concordance of normal methylation and normal imprinting. Genomic DNA was treated with sodium bisulfite, and then was PCR amplified and subcloned before sequencing. Ten to 15 clones were sequenced for each sample. Each line represents a separate clone. (•), methylated CpG sites; (○), unmethylated CpG sites. Case number is shown on the left. Single nucleotide polymorphisms are shown on the left, distinguishing alleles.
Figure 6:
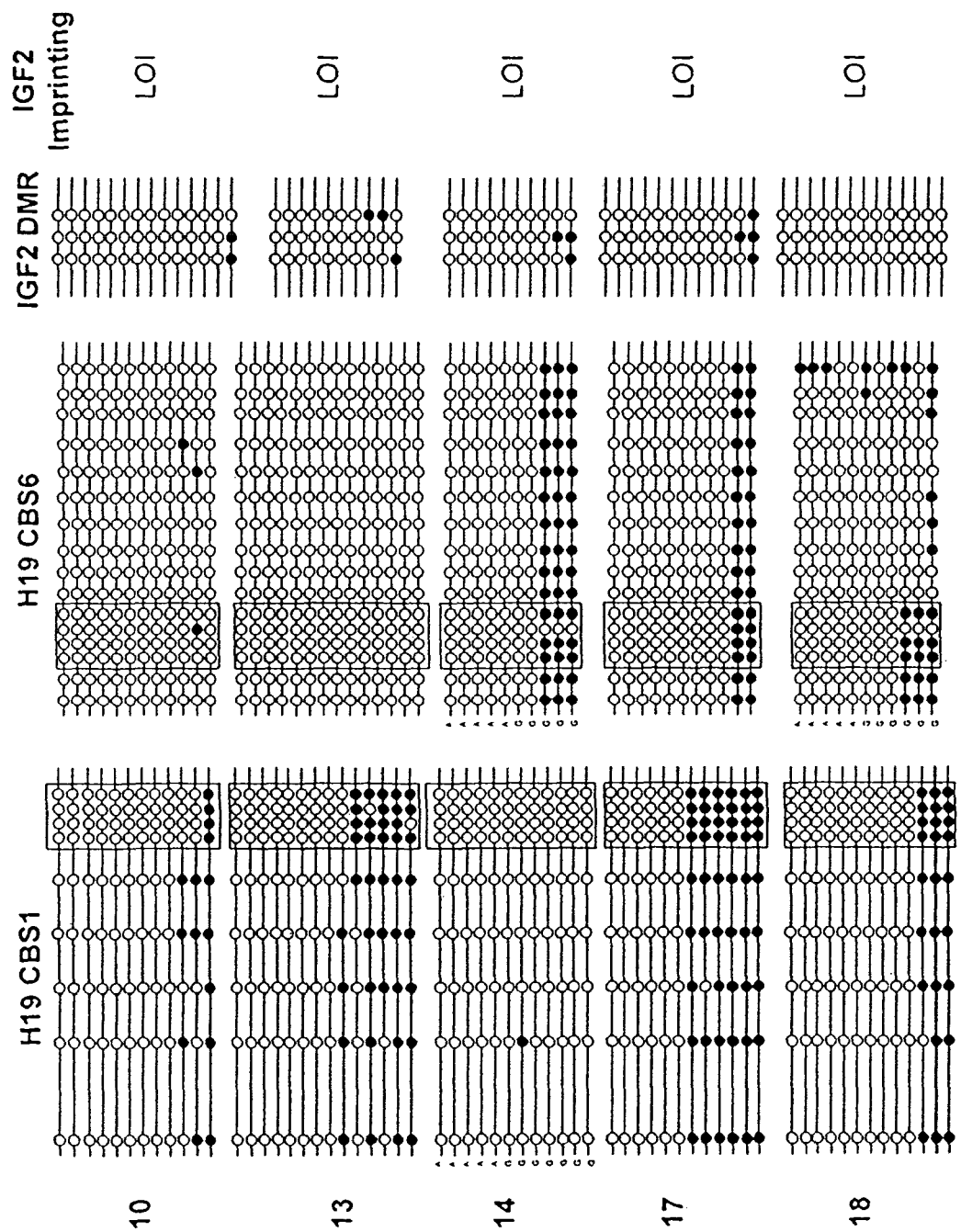
FIG. 6 shows hypomethylation of H19 and IGF2 DMRs in sporadic CRCs with LOI. The H19 DMR shows a general trend of hypomethylation and LOI of IGF2, whereas the IGF2 DMR shows complete concordance of hypomethylation and LOI. Labeling is as described in the legend to FIG. 5.

Hypomethylation of H19 and IGF2 DMRs in Primary CRCs. To determine whether hypomethylation was also linked to LOI in primary colon cancers, we then analyzed 20 CRCs informative for imprinting status of IGF2 (heterozygous for a transcribed polymorphism) by reverse transcription-PCR, 12 with LOI and 8 with normal imprinting. All 8 of the CRCs with normal imprinting showed the normal half-methylation pattern at the IGF2 DMR, and all 12 of the CRCs with LOI showed marked hypomethylation of the IGF2 DMR (P=0.000007; FIGS. 5 and 6). In tumors with normal imprinting, the fraction of CpG sites that were methylated was 43.6±10.9%, whereas in tumors with LOI the fraction of sites methylated was 10.9±9.4% (P<0.0001). In addition, for each DMR, 15-20 clones were independently sequenced from the PCR product of each bisulfite-treated sample, and each experiment was repeated at least once. We also observed hypomethylation of the H19 DMR in CRC, although the differences were not absolute as in the case of the IGF2 DMR, but were in marked contrast to Wilms' tumors with LOI (Table 4). These results also differ markedly from those of Nakagawa et al. (H. Nakagawa et al, Proc. Natl. Acad. Sci. USA, 98: 591-596, 2001), who reported hypermethylation of CBS6 in colorectal cancer. Finally, because LOI is found at increased frequency in both tumor and normal tissue of patients with CRC, we also examined the matched normal mucosa of 3 CRC patients whose tumors showed LOI. As we reported earlier (H. Cui et al, Nat. Med., 4: 1276-280, 1998), the matched normal mucosa also showed LOI of IGF2, although methylation had not been examined in that study. We found the same pattern of hypomethylation in the normal colonic mucosa in each patient as we found in tumors (Table 4), indicating that this epigenetic abnormality was not limited to the cancers.

TABLE 4

IGF2 imprinting status and methylation alterations in primary CRC.[2]

| Sample No. | IGF2 LOI | Methylation Status | | |
|---|---|---|---|---|
| | | H19 CBS1 | H19 CBS6 | IGF DMR |
| 1T | No | Half | Hypo | Half |
| 2T | No | Half | Hypo | Half |
| 3T | No | Half | Hypo | Half |
| 4T | No | Half | Half | Half |
| 5T | No | Half | Hypo | Half |
| 6T | No | Half | Half | Half |
| 7T | No | Half | Half | Half |
| 8T | No | Hyper | Half | Half |
| 9T | Yes | Hypo | Hypo | Hypo |
| 10T | Yes | Hypo | Hypo | Hypo |
| 11T | Yes | Hypo | Hypo | Hypo |
| 12T | Yes | Hypo | Hypo | Hypo |
| 12N | Yes | Half | Hypo | Hypo |
| 13T | Yes | Half | Hypo | Hypo |
| 14T | Yes | Hypo | Hypo | Hypo |
| 15T | Yes | Half | Hypo | Hypo |
| 16T | Yes | Half | Half | Hypo |
| 17T | Yes | Half | Hypo | Hypo |
| 17N | Yes | Half | Hypo | Hypo |
| 18T | Yes | Hypo | Hypo | Hypo |
| 18N | Yes | Hypo | Hypo | Hypo |
| 19T | Yes | Half | Half | Hypo |
| 19N | Yes | Half | Half | Hypo |
| Fetus | No | Half | Half | Half |

[2]Annotation as in Table 1.

Neutral Polymorphisms of DNMT3B in Human CRCs. Because LOI and hypomethylation were present in normal tissue, and DNMT3B appeared to play a role in LOI in HCT116 cells, we examined all 20 of the CRC for germ-line mutations in the DNMT3B gene. Six of 20 patients showed a single variation in the coding sequence leading to amino acid substitutions: G892T (G210W), G1390A (A376T), A1451G (Y396C), G2044A (V594I), G2086A (V608M), and T1436C (L391P). To distinguish between neutral and functional variants, we performed site-directed mutagenesis and transfection into 293/EBNA1 cells, together with an episomal vector, which was the target for de novo methylation. None of the variants disrupted DNMT3B methyltransferase activity (data not shown). Thus, these sequence variations represent neutral polymorphisms.

Discussion

The study reported in this Example has two major results. First, hypomethylation, rather than hypermethylation, is linked to LOI of IGF2 in human CRC based on two lines of evidence. In CRC lines in which hypomethylation is induced artificially by DNMT1/DNMT3B double knockout, LOI is found only in the hypomethylated lines. Indeed, unmodified HCT116 cells with hypermethylation of the H19 DMR exhibit normal imprinting, even though Wilms' tumors with hypermethylation of the same sites show LOI (27). Furthermore, in primary human CRC, as well, LOI is linked to hypomethylation rather than hypermethylation. The latter result is in contrast to the findings of Nakagawa et al. (35), who reported hypermethylation of the H19 in CRC with LOI of IGF2. It should be remembered that the first epigenetic alterations found in human cancer was hypomethylation of DNA (1) and that CRC show global hypomethylation even in the presence of specific sites of increased DNA methylation (2). Furthermore, the assumption that CpG islands are universally hypomethylated is incorrect, as imprinted genes show normal methylation, and we have also identified recently many normally methylated CpG islands in normal cells (36). Therefore, a more correct and inclusive view is that cancers show epigenetic instability, including global hypomethylation, and sites of both aberrantly increased and decreased methylation, that lead to altered gene regulation.

The second major result of this study provided in this Example is that normal imprinting in the colon and LOI in CRC is specifically linked to the methylation status of a DMR within IGF2 and to a lesser extent to the methylation status of H19. Thus, all 8 of the cancers with normal imprinting showed normal half-methylation of the IGF2 DMR and all 11 of the cancers showed hypomethylation of this DMR, as well as 3 matched normal mucosal specimens that also showed LOI. Takai et al. (37) recently described partial or complete hypomethylation of the H19 ICR in two of four bladder cancers, but no relationship to H19 imprinting; IGF2 was not examined in that study. No alteration of H19 imprinting was observed in the CRC examined here. It has been reported earlier that cancers with LOI also show LOI in the matched normal mucosa (Cui, H., Horon, I. L., Ohlsson, R., Hamilton, S. R., Feinberg, A. P. Loss of imprinting in normal tissue of colorectal cancer patients with microsatellite instability. Nat. Med., 4: 1276-280, 1998), so we would expect that this methylation abnormality is generally present in the colon of these cancer patients, as disclosed in Example 1.

An important implication of this result is that it suggests a mechanism for regulation of IGF2 imprinting independent of enhancer competition. By the enhancer competition model, IGF2 and H19 promoters compete on the same chromosome for a shared enhancer, and access of the maternal IGF2 allele to this enhancer is blocked by the H19 DMR when unmethylated, likely because of the insulator activity of CTCF binding to the unmethylated H19 DMR (22, 23, 24, 25, 26). However, in CRC with LOI, the H19 DMR is hypomethylated on both alleles, and hypomethylation of the IGF2 DMR is specifically linked to LOI of IGF2 in both primary CRC and in HCT116 cells in which methyltransferases have been disrupted experimentally.

Some clues to function are available from mouse studies, although it is difficult to relate mouse experiments precisely to the human, as the DMR sequences themselves differ between species. Nevertheless, the region corresponding to the human DMR studied here is in the same physical relationship to human IGF2 exons 2 and 3, as is mouse "DMR0" to mouse IGF2 pseudoexons 1 and 2 (34). To date, no mouse knockout of DMR0 by itself has been reported, although deletion of DMR1, or of DMR0 and DMR1 together, lead to activation of the normally silent maternal allele of IGF2 (38, 39). The mouse knockout experiments suggest the existence of a transcriptional repressor within IGF2 (38, 39). This hypothesis appears consistent with the results herein, and additionally the present results suggest that methylation of this human IGF2 DMR recruits transcriptional repressors to the maternal allele. By this model, hypomethylation would lead to LOI by loss of association of these repressors to the IGF2 DMR. The results herein also suggest two potentially valuable lines of experimentation: knockout of DMR0 in mouse and biochemical studies aimed at identifying factors of which the binding to the human IGF2 DMR is lost in tumors with LOI.

What is claimed is:

1. A method for identifying loss of imprinting (LOI) of the IGF2 gene in a human subject with colorectal cancer, comprising analyzing a biological sample from the subject for hypomethylation of a differentially methylated region (DMR) of the IGF2 gene, wherein the biological sample is a blood sample or a colon mucosa sample; and
    detecting hypomethylation of the DMR in the subject, wherein hypomethylation is as compared to the half-methylation of the normally imprinted gene, and wherein further the DMR of the IGF2 gene comprises SEQ ID NO:1, wherein detection of hypomethylation of the DMR in the subject correlates with loss of imprinting (LOI).

2. The method of claim 1, wherein the analysis is performed by contacting the biological sample with a primer pair comprising at least one pair of:
    SEQ ID NO:2 and SEQ ID NO:3;
    SEQ ID NO:4 and SEQ ID NO:5;
    SEQ ID NO: 27 and SEQ ID NO: 28; and
    SEQ ID NO: 29 and SEQ ID NO: 30.

3. A method for identifying an increased risk of developing colorectal cancer in a human subject, comprising analyzing a biological sample from the subject for hypomethylation of a differentially methylated region (DMR) of an IGF2 gene, wherein hypomethylation is as compared to the half-methylation of the normally imprinted gene, and wherein further the DMR of the IGF2 gene comprises SEQ ID NO:1, wherein detection of hypomethylation of the DMR in the subject correlates with loss of imprinting (LOI), wherein LOI is indicative of increased risk of the subject developing colorectal cancer, and wherein the biological sample is a blood sample or a colon mucosa sample.

4. The method of claim 3, wherein the method comprises bisulfite genomic sequencing.

5. The method of claim 3, wherein the subject is not a subject known to have a colorectal neoplasm.

6. The method of claim 3, wherein the biological sample is a blood sample.

7. A method for identifying an increased risk of developing colorectal cancer in a human subject, comprising analyzing a genomic DNA sample from the subject for hypomethylation of a DMR of an IGF2 gene, wherein hypomethylation is as compared to the half-methylation of the normally imprinted gene, and wherein further the DMR of the IGF2 gene comprises SEQ ID NO:1, wherein hypomethylation of the IGF2 gene correlates with the loss of imprinting of the IGF2 gene, wherein a loss of imprinting of the IGF2 gene is indicative of an increased risk of developing colorectal cancer, and wherein the genomic DNA sample is from a blood sample or a colon mucosa sample, thereby identifying an increased risk of developing colorectal cancer in the subject.

8. The method of claim 1, wherein the biological sample is a blood sample.

9. The method of claim 1, wherein the biological sample is a colon mucosa sample.

10. The method of claim 3, wherein the biological sample is a colon mucosa sample.

11. The method of claim 7, wherein the genomic DNA sample is from a colon mucosa sample.

12. The method of claim 7, wherein the genomic DNA sample is from a blood sample.

\* \* \* \* \*

SEQUENCE LISTING

<160> NUMBER OF SEQ ID NOS: 37

<210> SEQ ID NO 1
<211> LENGTH: 256
<212> TYPE: DNA
<213> ORGANISM: Homo sapiens

<400> SEQUENCE: 1
tctgttgcac cctggaccca gactcctcaa tccacccagg gtggtgtctg tggggagggg       60
gttcacttcc ccaggaagca cagccacgcc gtccctcact ggcctcgtca agcagagctg      120
tgtgtccagt ggcttttgct ggggccccct ccttatctcc ttccaaggtg ggggtgtttg      180
gaggtggagg aggctttcat attccgtgcc atgacccctc aaggcgggcc attcgtgtgc      240
accctccacc cccagt                                                     256

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
ggtgaggatg ggttttgtt                                                   20

<210> SEQ ID NO 3
<211> LENGTH: 21
<212> TYPE: DNA
<213> ORGANISM: Artificial sequence
<220> FEATURE:
<223> OTHER INFORMATION: PCR primer

<400> SEQUENCE: 3
ctactctccc aacctcccta a                                                21

<210> SEQ ID NO 4
<211> LENGTH: 20
<212> TYPE: DNA
<213> ORGANISM: Artificial sequence
<220> FEATURE:
<223> OTHER INFORMATION: PCR primer

<400> SEQUENCE: 4 attggggtg gagggtgtat                                                   20

<210> SEQ ID NO 5
<211> LENGTH: 21
<212> TYPE: DNA
<213> ORGANISM: Artificial sequence
<220> FEATURE:
<223> OTHER INFORMATION: PCR primer

<400> SEQUENCE: 5
tctattacac cctaaaccca a                                                21

<210> SEQ ID NO 6
<211> LENGTH: 6014
<212> TYPE: DNA
<213> ORGANISM: Homo sapiens

<400> SEQUENCE: 6
gcaacagtga tgtaatccta ggagcaattt gaggaggtta aaaatctttc agcctccaga       60

```
tgtgtgactc catgactcct aaaccataat ttctaatctg tggctaattt gttagtcctg    120
aaagtctagt ccccaggcag gaagagggtc tgtcctggga aagggctgtt attgtctttg    180
tttcaaagat aaactataaa ctaagttctt cccaaagtta gtccagcctg cacccagaaa    240
tgaataagaa ggcaagacag agttggttac gtcagatctc tttcattgtc ataattttct    300
gttatatatt ttttttttt tgagacagag tttcgctctt atcatccagg ctggagtcca    360
atggctcgat cttggctcac tgcaacctcc acctccggag ttccagtgat tctcctgcct    420
cagcctccca gtagctggga ttacaggcg cccaccacca tgcccagcta attttgtat     480 ttttagtaga gatgggattt cgtcaggttg gccaggttgg tcttgaactc ctgacctcag    540
gtgatccacc cacctcggcc tcccaaactg ctgggattac aggcatgagc caccatcgcc    600
ggccgatttt ctgtaataat ttttgcagag gcggtttcac caggagaacc aagcattaat    660
gcgctgtggc tgatgtgtag tagagcggca tttcccaatg ggagaaccct ggggctgtct    720
aggagcccat gcatggctgg gagcctaatc ccagggacac caccgatgac agctcccata    780
gcacgtagga cagtggatac ttggaggcaa agagaaatct ctgttctgca gtggtcatga    840
cttggacccc aaagaacttg agcccaaggt ccagagggag accctcccaa caaggcctcc    900
agcaggaaca gggatcgtgg gagcctgcca agcacagcgc acaggtattt ctggaggctt    960
cccattcagt cttggatgcc agcctcacca agggcggccc atcttgctga cctcaccaag   1020
ggaggcccgt ctcactgccc tgatggcgca gaatcggctg tacgtgtgga atcagaagtg   1080
gccgcgcggc ggcagtgcag gctcacacat cacagcccga gcacgcctgg ctggggttca   1140
cccacagaaa cgtcccaggt ctcccaggcc aggtgccgca ttggttcccg agggttgtca   1200
gagatagaca ctcatgcgac taacatcggg ctatgtgttt gattcacccc agggtgcatt   1260
gttgaaggtt ggggagattg gaggagatgc ttggggggaca atgaggtgtc ccagttcctt   1320
ggatgatagg gatctcggcc taagcgtgag acccctccta cagggtctct ggcaggcaca   1380
gagcctgggg gctcttgcat agcacatgtg tatttctgga ggcttcccct tcggtctcac   1440
cgccccgatg gtgcagaatc ggttgtagtt gtggaatcgg aagtggccgc gcggcggcag   1500
tgcaggctcc cacatcacag ctcaagcccg cccccagctga ggttcacccg cggaaacgtc   1560
ccgggtcacg caagctaggt gccgcaaggt tcacgggggt agtgagggat agaacactca   1620
tgggagccac attgggctac gtgtctgatt caccccaggg tgcactattg agggttgggg   1680
agatgagata ctttggtgac aatgaggtgt ccccattctt tggatgatgg ggatctcggc   1740
ctcagcgtga ggcccctccc acagggtctc tggcaggcac agaaactggg ggctcttgcg   1800
tagcacatgg gtatttgtgg acgcttcccc ttctgtctca ccacccggat ggcacagaat   1860
cggttgtaag tgtggactca aaagtggccg cgcggcggca gtgcaggctc acacatcaca   1920
gcccaagccc tccctggatg gggttcgccc gcggaaacgt cctgggtcac ccaagccagg   1980
tgccgcaggt ttctcggagg tcttctggga ataggacgct catgggagcc acaccacgtc   2040
ttcgtatcgg gccatatcca cggccgcgtg gccccaggtc acactctgag ggcttcagtg   2100
tcatggcctg ggactcaagt cacgcctacc cgcgtgatga gcacagcaaa ttccaacaaa   2160
agcttatact ttccacatcc atcccagagc acagatccga ctaaggacag cccccaaatc   2220
ccgagccttt ttctgaactg acaattgcct ccccagtgaa cactctgagc ttgtcaatct   2280
taagtggcca gacattaaca ttcccattca gtgcaggttt gagatgctaa tttaggagct   2340
tgagatgcta aagagctggg agtgccactg ctgctttatt ctggggtcta ggatccttgt   2400
gttggctgag ataatctgct aatgtgggtg cagcagacat cccgcggttt gtggaatcga   2460
```

```
taaaggatgg ggatcaatgg tgtttgtgca ctgtgcggtc tgtgcccaat tgcctgcctt    2520
gtgctgtgga atctgtacac ctggccaaca tgtgcttgtg tgagcctgac agtgcatttt    2580
ccagagcctc acctcggctc tgccctggag gctctgtgct gctggaatca gactcaagga    2640
cctcatcaga ggaccatggc cccgtatcac ctgggtcagg cactgaagct gggacaggag    2700
agcagagact tccaaaatga gggatccctg tgttctgagg tgatcatgac tgggacccaa    2760
ggactcaagc gcatgctcca gagggaatcg tttcccacaa ggccttttggc aggaacaggg    2820 atcctgggag cctgccaagc agagcgcaca gtgttcctgg agtctcgctg cccagatgcc    2880
acggaatcag ttgaaggtat ggaaacacag gtggccacgt ggtagcaggg caggctcagg    2940
cgtcatagcc cgagcccggc tacctgtggt ttgcctgcag aaacatcccg ggtcaacagg    3000
ccaggcaccg cattggttcg cgagggtcat cggggggtagg acccttgtac gagccacatc    3060
gggctacgtg cctgattcac cccagggtgc actgttgaag gttggggaga tgagaggaga    3120
tacttggggg acagtgaagt gtccccattc tttggatgat gggatctcg gcctcagcgt    3180 gagacccctc ccacagggtc tctggcaggc tcaagagccc aggggctctt gcatagcaca    3240
tgaatatttc tggaggcttc cccttcagtc tcaccacccg gatggtgcag aattggttgt    3300
agctgtggaa tcggaagtgg ccgcgtggcg gcagtgcagg ctcacacatc acagcccgag    3360
cccaccccag ctggggttcg cccgcggaaa cgtcccgggt cccgcaagcc aggcgccgca    3420
gggttcacgg gggtcatcag ggataggaca ttcatgggag ccacatcggg ctatgtgtct    3480
gattcacccc agggtgcact attgagggtt gggaagatga gaggagatgc ttgggggaca    3540
atgaagtgtc cccattcttt ggatgatggg gatcttggcc tcagggtgag atccttcttg    3600
cagggtctat ggcaggcaca gagcccgggg gctcttgcat agcacatgtg tatttctgga    3660
ggcttcccct tcagtctcac cgcccggatg gcacggaatt ggttgtagtt gtggaatcgg    3720
aggtggctgc gcggcggcag tgcaggctca cacatcacag cccgagcccg cccagctgg    3780 ggttcgcccg tggaaacatc ccaggtcatc caagcccggc gccacagggt tcacaggggt    3840
cgtgaggtat aggacactca tgggagccat atcgggctac gtgtctgatt cacccccaggg    3900 tgcactgttg aaggttgggg agatgggagg agatactagg ggaacaatga ggtgtcccag    3960
ttccatggat gatggggatc tcggccctag tgtgaaaccc ttctcgcagg gtctctggca    4020
ggcacagagc ccgggggctc ttgcatagca catgggtatt tctggaggct tctccttcgg    4080
tctcaccgcc tggatggcac ggaattggtt gtagttgtgg aatcggaagt ggccgcgcgg    4140
cggcagtgca ggctcacaca tcacagcccg agcccgcccc aactgggggtt cgcccgtgga    4200 aacgtcccgg gtcacccaag ccacgcgtcg cagggttcac gggggtcatc tgggaatagg    4260
acactcatag gagccgcacc agatcttcag gtcgggcatt atccacagcc ccgtggcccc    4320
gggtcacact ccgagggctt cagtgtcatg gcctgggact caagtcacgc ctacttatgt    4380
gatgatcaca gtgtgttcca ccaaaatctt acatttttcca catctatccc agagcacagc    4440
tccgactccg tctaaggaca gccccccaaat ccccagcctt ttactgaact gacaattgcc    4500
tccccagtga acactctgat ctcctcagcc ctaagtggcc agacattaac attctcattc    4560
aatgcaggtt tgaggtgcta attcaggagc ttaagatgct aaagagctgg gagcgccact    4620
gctgctttat tctctggtcc aggatccttg tgttgctgga gataatccat tatcgtgggt    4680
gcagcagaca ccctgcggct tgtggactcg gtacggggtg gggatcctga tggggttagg    4740
atgttcgatg gctcggtgt gctccacgct cagggatcat cacgtccggc cggcggtagt    4800
tggcacgtgg agaggtgaat ttgcccacag gtgttccccg tgcctgcgca ttgctggcag    4860
```

-continued

```
cacgaccgga tcctgtgcta gcccctccca caatgcctgg agcaggagcg aggggcctgg    4920
ggagccgcct tgcctggagc atttgtattt ccggagtatt tcctgagtct cccccttggg    4980
cttgggtgct gtccccagtg agcccatctc ccagcgatgg cacagaatcg gttgtggctg    5040
tggagacgga aatggccgag aggcggcagt ggtgactcac atcacagtct gaaggtgacc    5100
caaggctgga ctccactttt agcaaaatgt gggggtctgc cttggtctcc taacttgggg    5160
gtccactcat ggaaaagcct gagaattttc atgccatgga aattccccca tgtcgtgggg    5220
ttcacgcacg acaaagcccg gcggtcagtg ctcagcaggc aagcactcag ccctttccgg    5280
tggggccatg ggaacagagg gtttgccgaa ggcgcggcca gcccttccac atcccagagg    5340
gcctgctgcg tgattggacc cgtgaactct gggtcccttg gccctggtgc tccccttcac    5400
ggctttgaca ctcgagactt gaggtgaacc cagggactg cagggcccca acaaccctca    5460
ccaaaggcca aggtggtgac cgacggaccc acagcggggt ggctggggga gtcgaaactc    5520
gccagtctcc actccactcc caaccgtggt gccccacgcg ggcctgggag agtctgtgag    5580
gccgcccacc gcttgtcagt agagtgcgcc cgcgagccgt aagcacagcc cggcaacatg    5640
cggtcttcag acaggaaagt ggccgcgaat gggaccgggg tgcccagcgg ctgtggggac    5700
tctgtcctgc ggaaaccgcg gtgacgagca caagctcggt caactggatg ggaatcggcc    5760
tggggggctg gcaccgcgcc caccagggg tttgcggcac ttccctctgc ccctcagcac    5820 cccacccta ctctccagga acgtgagttc tgagccgtga tggtggcagg aagggggcct    5880
ctgtgccatc cgagtcccca gggacccgca gctggccccc agccatgtgc aaagtatgtg    5940
cagggcgctg gcaggcaggg agcagcaggc atggtgtccc ctgaggggag acagtggtct    6000
gggagggaga agtc                                                      6014
```

<210> SEQ ID NO 7
<211> LENGTH: 21
<212> TYPE: DNA
<213> ORGANISM: Artificial sequence
<220> FEATURE:
<223> OTHER INFORMATION: PCR primer

<400> SEQUENCE: 7
atcttgctga cctcaccaag g                                              21

<210> SEQ ID NO 8
<211> LENGTH: 21
<212> TYPE: DNA
<213> ORGANISM: Artificial sequence
<220> FEATURE:
<223> OTHER INFORMATION: PCR primer

<400> SEQUENCE: 8
cgatacgaag acgtggtgtg g                                              21

<210> SEQ ID NO 9
<211> LENGTH: 22
<212> TYPE: DNA
<213> ORGANISM: Artificial sequence
<220> FEATURE:
<223> OTHER INFORMATION: PCR primer

<400> SEQUENCE: 9
ccgactaagg acagcccca aa                                              22

<210> SEQ ID NO 10
<211> LENGTH: 22
<212> TYPE: DNA

```
<213> ORGANISM: Artificial sequence
<220> FEATURE:
<223> OTHER INFORMATION: PCR primer

<400> SEQUENCE: 10
tggaagtctc tgctctcctg tc                                              22

<210> SEQ ID NO 11
<211> LENGTH: 22
<212> TYPE: DNA
<213> ORGANISM: Artificial sequence
<220> FEATURE:
<223> OTHER INFORMATION: PCR primer

<400> SEQUENCE: 11
acagtgttcc tggagtctcg ct                                              22

<210> SEQ ID NO 12
<211> LENGTH: 22
<212> TYPE: DNA
<213> ORGANISM: Artificial sequence
<220> FEATURE:
<223> OTHER INFORMATION: PCR primer

<400> SEQUENCE: 12
cacttccgat tccacagcta ca                                              22

<210> SEQ ID NO 13
<211> LENGTH: 22
<212> TYPE: DNA
<213> ORGANISM: Artificial sequence
<220> FEATURE:
<223> OTHER INFORMATION: PCR primer

<400> SEQUENCE: 13
acagggtctc tggcaggctc aa                                              22

<210> SEQ ID NO 14
<211> LENGTH: 22
<212> TYPE: DNA
<213> ORGANISM: Artificial sequence
<220> FEATURE:
<223> OTHER INFORMATION: PCR primer

<400> SEQUENCE: 14
atgagtgtcc tattcccaga tg                                              22

<210> SEQ ID NO 15
<211> LENGTH: 21
<212> TYPE: DNA
<213> ORGANISM: Artificial sequence
<220> FEATURE:
<223> OTHER INFORMATION: PCR primer

<400> SEQUENCE: 15
aactggggtt cgcccgtgga a                                               21

<210> SEQ ID NO 16
<211> LENGTH: 21
<212> TYPE: DNA
<213> ORGANISM: Artificial sequence
<220> FEATURE:
<223> OTHER INFORMATION: PCR primer

<400> SEQUENCE: 16
caaattcacc tctccacgtg c                                               21
```

```
<210> SEQ ID NO 17
<211> LENGTH: 22
<212> TYPE: DNA
<213> ORGANISM: Artificial sequence
<220> FEATURE:
<223> OTHER INFORMATION: PCR primer

<400> SEQUENCE: 17
gatcctgatg gggttaggat gt                                          22

<210> SEQ ID NO 18
<211> LENGTH: 22
<212> TYPE: DNA
<213> ORGANISM: Artificial sequence
<220> FEATURE:
<223> OTHER INFORMATION: PCR primer

<400> SEQUENCE: 18
ggaatttcca tggcatgaaa at                                          22

<210> SEQ ID NO 19
<211> LENGTH: 22
<212> TYPE: DNA
<213> ORGANISM: Artificial sequence
<220> FEATURE:
<223> OTHER INFORMATION: PCR primer

<400> SEQUENCE: 19
ggtctgcctt ggtctcctaa ct                                          22

<210> SEQ ID NO 20
<211> LENGTH: 22
<212> TYPE: DNA
<213> ORGANISM: Artificial sequence
<220> FEATURE:
<223> OTHER INFORMATION: PCR primer

<400> SEQUENCE: 20
ggccactttc ctgtctgaag ac                                          22

<210> SEQ ID NO 21
<211> LENGTH: 22
<212> TYPE: DNA
<213> ORGANISM: Artificial sequence
<220> FEATURE:
<223> OTHER INFORMATION: PCR primer

<400> SEQUENCE: 21
cagtctccac tccactccca ac                                          22

<210> SEQ ID NO 22
<211> LENGTH: 22
<212> TYPE: DNA
<213> ORGANISM: Artificial sequence
<220> FEATURE:
<223> OTHER INFORMATION: PCR primer

<400> SEQUENCE: 22
gacctctccc tcccagacca ct                                          22

<210> SEQ ID NO 23
<211> LENGTH: 25
<212> TYPE: DNA
<213> ORGANISM: Artificial sequence
<220> FEATURE:
<223> OTHER INFORMATION: Primer sequence
```

```
<400> SEQUENCE: 23
gagtttgggg gttttttgtat agtat                                          25

<210> SEQ ID NO 24
<211> LENGTH: 24
<212> TYPE: DNA
<213> ORGANISM: Artificial sequence
<220> FEATURE:
<223> OTHER INFORMATION: Primer sequence

<400> SEQUENCE: 24
cttaaatccc aaaccataac acta                                            24

<210> SEQ ID NO 25
<211> LENGTH: 23
<212> TYPE: DNA
<213> ORGANISM: Artificial sequence
<220> FEATURE:
<223> OTHER INFORMATION: Primer sequence

<400> SEQUENCE: 25
gtatatgggt attttttgga ggt                                             23

<210> SEQ ID NO 26
<211> LENGTH: 21
<212> TYPE: DNA
<213> ORGANISM: Artificial sequence
<220> FEATURE:
<223> OTHER INFORMATION: Primer sequence

<400> SEQUENCE: 26
ccataacact aaaaccctca a                                               21

<210> SEQ ID NO 27
<211> LENGTH: 24
<212> TYPE: DNA
<213> ORGANISM: Artificial sequence
<220> FEATURE:
<223> OTHER INFORMATION: Primer sequence

<400> SEQUENCE: 27
gggaatgttt atttatgtat gaag                                            24

<210> SEQ ID NO 28
<211> LENGTH: 20
<212> TYPE: DNA
<213> ORGANISM: Artificial sequence
<220> FEATURE:
<223> OTHER INFORMATION: Primer sequence

<400> SEQUENCE: 28
taaaaacctc ctccacctcc                                                 20

<210> SEQ ID NO 29
<211> LENGTH: 21
<212> TYPE: DNA
<213> ORGANISM: Artificial sequence
<220> FEATURE:
<223> OTHER INFORMATION: Primer sequence

<400> SEQUENCE: 29
taatttattt agggtggtgt t                                               21

<210> SEQ ID NO 30
<211> LENGTH: 20
<212> TYPE: DNA
```

```
<213> ORGANISM: Artificial sequence
<220> FEATURE:
<223> OTHER INFORMATION: Primer sequence

<400> SEQUENCE: 30
tccaaacacc cccaccttaa                                                     20

<210> SEQ ID NO 31
<211> LENGTH: 26
<212> TYPE: DNA
<213> ORGANISM: Artificial sequence
<220> FEATURE:
<223> OTHER INFORMATION: Primer sequence

<400> SEQUENCE: 31
gtataggtat ttttggaggt ttttta                                              26

<210> SEQ ID NO 32
<211> LENGTH: 26
<212> TYPE: DNA
<213> ORGANISM: Artificial sequence
<220> FEATURE:
<223> OTHER INFORMATION: Primer sequence

<400> SEQUENCE: 32
cctaaaataa atcaaacaca taaccc                                              26

<210> SEQ ID NO 33
<211> LENGTH: 23
<212> TYPE: DNA
<213> ORGANISM: Artificial sequence
<220> FEATURE:
<223> OTHER INFORMATION: Primer sequence

<400> SEQUENCE: 33 gaggttttt attttagttt tgg                                                  23

<210> SEQ ID NO 34
<211> LENGTH: 22
<212> TYPE: DNA
<213> ORGANISM: Artificial sequence
<220> FEATURE:
<223> OTHER INFORMATION: Primer sequence

<400> SEQUENCE: 34
actataatat ataaacctac ac                                                  22

<210> SEQ ID NO 35
<211> LENGTH: 4992
<212> TYPE: DNA
<213> ORGANISM: Homo sapiens

<400> SEQUENCE: 35
ggatcctggt ttctgaagga ggggaagaac ttctgctgct ggagggtgca ggaagcctcc         60
tgagagcagc ctcaacttca ggggatgggg tgtgcaggaa aggccattgt ggagagggtt        120
ctcctttagg gctgcacaaa gccactgagg cttttgcaag gaaataggt tttccttgtc         180 taattcacca agcaaaatgg gaggggtagg ggaggagggc taggccgctc ttcccagcgg        240
gaacacacag ctgtcttcac aagtgtgaaa ggaagagtct ttctgtgtga aaagtttcct        300
cccgttgcat cccccatccc attcccagag acaaacagga gactttgcag aggagccagg        360
ggcccgagat tctggcgcag agattttatt tatacatata tacaccattt tacaggtaaa        420
gcttccttcc ctcctgcctc cctatgcctg ctgaccacca gcaagaaatt ggacaggaga        480
```

-continued

```
ctgaggagaa acgccgggag aggcaacaac cgccctccat gtccccccta ggtttagctt    540
ctctcctcct gatggcgcac ctggtccccc ttgctgctct cccagcctcc ctggcacaga    600
gaggcaccct ggggccaagg cagtttccct gggaatgctc attcatgcat gaagtttttc    660
tctgttgcac cctggaccca gactcctcaa tccacccagg gtggtgtctg tggggagggg    720
gttcacttcc ccaggaagca cagccacgcc gtccctcact ggcctcgtca agcagagctg    780
tgtgtccagt ggcttttgct ggggccccct ccttatctcc ttccaaggtg ggggtgtttg    840
gaggtggagg aggctttcat attccgtgcc atgacccctc aaggcgggcc attcgtgtgc    900
accctccacc cccagtgcca ggcagaagcc catcctcacc caggaacagg gcagcctgtc    960
caacagaagg gtctcggcct ctccatcagc accgggaagc cctttctagg caaacttctc   1020
accacttctt ccctcccctta tactttgaaa gaggagctc taggcagggg aggggctaga   1080
gggggaagcc gctgcccaga tcctgacaag gtgacctgaa ggaacccggg gaggggatg    1140 ggacagggct caggcttggg gtgtatgggg aggggggctt tgcttttaaa agaggtcatc   1200
tcagcaatat cttttgtttt ttccccaggg gccgaagagt caccaccgag cttgtgtggg   1260
aggaggtgga ttccagcccc cagccccagg gctctgaatc gctgccagct cagccccctg   1320
cccagcctgc cccacagcct gagccccagc aggccagaga gcccagtcct gaggtgagct   1380
gctgtggcct gtggcccagg cgaccccagc gctcccagaa ctgaggctgg cagccagccc   1440
cagcctcagc cccaactgcg aggcagagag gtgagtgtct caggcaccct gaggcctggc   1500
agagagggcc acaggctctg cgcgggagtc ttcgaactgg gatctccccc ttctgcaagc   1560
agctttggct cagagaggct ggcgtggatt cagtcacaca gctgggatct ggagttccgt   1620
ggttggctcc aggtgcttcc gtctagggc cagagcaggt gtgggcagag caggttcccc    1680
gcagtctcca cggcaccgag gtcctggcag gggagctcct gggagacgaa agagggcaaa   1740
gaagggagaa ggggcaggga gagagcgggc agccaaaggg gagaagatgg ggggcagaaa   1800
gtgggtagag agggaaaaag ggaaaatatc attggggaag aacctaaaaa cccaaggaaa   1860
gctgggctct gctgggggct gtgagacccc cgggttctcc ccgccccagg ctgctggcca   1920
tggggtcttg caccaatggc ctgaccttc tgtcggtctg tatttatcaa agtgggtgac    1980
agtctcaggc ctcctggctg ttcagaattg aggtaataac cagaggcctt ctgagcaaag   2040
ggcctaaggg gctccggcgt caggatccag caggtgactc ttcaggctga tttgcccatc   2100
ccagatagaa gccgggagtg ttcttcaaa ggtgtcttta ccttagacac tcaataaaat    2160
ggtaacacag tggcgccgcc tcagtccttt ggagtgtgca ccgtctgaac ccctctccca   2220
gggccctctc ccaagcaccc caacctggac ccatatcccc cacgtacttt tggctttggg   2280
cagattgagc agccttgggg tggtctgtgc tgtctggtgt ggagggttgc agttcgggtc   2340
cttagtccta cttcccaggc cggccgggct gacgccagcg agtgtgtcct tccccagcga   2400
ggggagtgag cgcaaggtca gcgcctcgtc tgcggcgccc tgcagggggt gacggagggg   2460
cgctctgagg acccttggag aaaggagctg ggtttgtaaa atgctgggct tggtcccacg   2520
gacggcggag cggtgagctc agagccgagc ctggggagga aatgggaatg agaaaggccc   2580
acttcagggc tggtgagcga ggggatgggg agcagccaca ggccgaggct ggggcatggg   2640
ccaggctcca tggggtgagt ctgagtcctt gaggggatgt tcatcctctg tggaatgtgg   2700
gtttgccagt ggagaggaga ccagcgttgc cctggtgagg tgctggttca gggctgggg   2760 gcggacgctg cttggggcta aagttcctgc cggccaagct ctgggtggga ggagaccctg   2820 gcccccctccc aacacccttg gactgctggc gggacccttc ctacctccgg gggctggaag  2880
```

```
tagtgggggga ggagccagtc ttgaggaaga accccgatgc tggtcttgac tagaggggag    2940
ccggtgtgct tttcgagcct cagggtgacc cgcgtctgcc ccagcctcca gcctgccctg    3000
gtcacttctg actaaataag gagagcactc agcaggcagc cccacgaggg aggggaaca     3060
tgtgtgcacc cccactcccc cacctgctcc tccctcccta cagggccact acaccctgct    3120
gtgggcaccc caaggtgacc ctcagccttc ttcctacctt aaaaagtcca ggcatgcgtt    3180
ttcaagcatg agcggtggcc ccctggggga aggcacctcg gcagggcaga acaaagggaa    3240
gggacccccca aacaggtcac tggtgtaatt gtccccagca cccccaaaga ggaggagaac   3300
ccacaactcg gaactggggc tcaccccccga tgcccaacct gtcccagcc tgggaagcag    3360
gcgtggagga aaggtggggg ggagcctaga gctggccctg ggggccctgg ttttgtccat    3420
gacgggagcc tcggcaacct agtccgctct cccggggacc aggtttgcag acaggcacct    3480
ttcaaatgct cctcacccccc aaatttacaa gtcaccctgc agaggaaaac atcaacacag   3540
ccaggggttc tctgctggag ctcccccctt ctataggcac agccggagag ccagagagc    3600
tggggacacg gggaggctgc agaaggctgg tgggaagggg ggcagtgatg ggtggggaga    3660
gatgggccag atgttcttgg aatgggacat gggggtgatt gatgcagaca gaaatttgaa    3720
ggggacattc ccacgtgtct tgttctgtgg gtggaaaatg ggctgttttt catggtgggg    3780
gcgggttctc cctgtcttgc caagctaatg tgaaagagat gcctcatcct gcccagctcc    3840
ccacacctgt ccaaggccat taacttctgc ctccccagtg tcaggctttg agatgccccc    3900
cttctagccg gggtcctcct atggggtgac aatgggaca  agcaatgccc actgtagttg    3960
ccccaggatc ccccaccatt ctgctggtcc ccagcggtgc cccctctctg gcagtacccc    4020
cacccacccc acaggtcccc ttagggccac tgcccatcgc ccgacattgc caacgccaa    4080
ggggtgacct tgttcctgcc gacagggccg ttgggcgcct gcatgcgggt ttaatatttg    4140
cctataagga actgggcttt ccccagccgg agtggacaga cttttccctga aaattcgctt   4200
ggagagaacg aaaagagacc ctggcacccc agcggcgtgc agccctgcac cccccctcctc  4260
ccgggccccg tgtttctcat tttcctcccc acttcctctg ctcttcagtg ttacccaaac   4320
aaaactggtt tcacccttgt ttggtgctgg cgaaggcccg aacggcgcgc gcaaagctcc   4380
ggggcaggcc ggaggtggcc accggggggtg ctccgggccc ccaagccaag ccggggaata   4440
gcctgccccc ggtggcggct cggcgcgcgg ttcgcctagg ctcgcagcgc ggaggcgagt   4500
ggggcgcagt ggcgagggg agcctgcgga cctcccacgc ggggaccgag caggtatctg    4560
ggagtcccgg gagcgcccgg gaagcagcgt cctggtcgct ccctcgcggc ccttgggttt   4620
cttccttaca cccggacgcc cgctaagctc gggctgccgc cacaaacgcg ctctccgtgt   4680
ggagaaggca aagaaaaaaa aaataaaagc aaaaggaaga aaaacccaa agaacgaaaa    4740
gcagaatttc agccggccgt gcgcgccagg gcgctccgcg ctacctgccc gcgccgcccg   4800
cgctcgggtt cccggggagg gcgccagtgc tccgcgcgcg cccagccaa ggtgaatccc    4860
cggcagcgcc ttccttccgc tgcccgggaa gcttgagctc aacaattagc ccttgatcct   4920
cggggggattc caatccacgg aacaacttcc ctgctttccc cgaactcgga cattttactt  4980
tttctgggat cc                                                      4992
```

<210> SEQ ID NO 36
<211> LENGTH: 25738
<212> TYPE: DNA
<213> ORGANISM: Homo sapiens

<400> SEQUENCE: 36

```
gatccctgag atgaagtggc tctgtcagga ttcaatcaga gaagcaccac ctcctcacgg    60
tcaaagggca gggggctttgt tggaagggat cggaccttct gccaagatgg agctccaggc   120
tgtctgtgag acgctactgc ccggctctgg ggctgggcct gaagccagca ggacaggtgg   180
tcaggaaaga agatgggcaa gaagtgggaa ggggcaaggg ccacctggac ttcacgaggc   240
cacacgtgaa cccacgtgga cagtccagtg ccctacatct gtctcttacc actttatgct   300
gcactgaata atgttccctg gaaattcatg tccacccagg acctgtgagt gtccccggaa   360
attcatgtcc acccaggacc tgtgagtgtc cccggaaatt catgtccacc caggacctgt   420 gagtgggtc ttctgtggac aagggctttt gtgggtgcaa ccaaataaag acaaagtcac    480
actgaattga ggcgggggga agcatccatt caatgagtgt cgtccttgta acaagaggga   540
aatttgcaca cagagacaga cacacagtgg aggaggccgt gtgaagacag aggcagagac   600
tggagcaacg cagccacaca ccacaggaca cctggagccc cagaagccca aaggggcaa    660 ggaggggcca cgctagggcc ttgcgaaaga gggcggccct gccctcccct gggtggtgaa   720
cctctgggct ccagagctgt gagagagtcc attcctatgg ctaaagccac ccagtctgtg   780
atcactgtca cagcagcccc aggaatcaaa cccctccaat cccaaaacac aggggacatc   840
cggaggagca agcacccctc accaggggc cacagacacc catggcccag acccagagg    900 agctgcaggc ttagggccca gggccagcag gctgagccag ggacggtgac accaggcatg   960
cgcagcagca gcacccaggc agcacccag cagatgccaa tgtggtggcc gcttccaccc   1020
actggtcacg ttgcagccgg gtgagtctgc cagggctgcc gcaacaaacc gccatggacc   1080
gggaggctta aatgagggaa atatatcctc tcccagtcct ggaggctgga gtccaagatc   1140
agggctgctg cagagctggg tcctccaagg cctctctcct tggcttatag atcctgcctt   1200
ctccacatgt cctcacgggg tcatccctcc gtgtgtgtct gtgtcctcct ctcctcttcc   1260
tataaggaca cagtcctatg agactgtgct caccccctgct cacatcagga aacggtcct    1320 gtgtctcctc tcgggacctc atcttcatgc ctcccccttg gttaccccac ggtcaggact   1380
cagccaccag cgtgagccca cacaccggct ctggagtggt gggcacaggt gagagggagg   1440
tacagctgcc acagccagga aaccccagga cgatcctgaa tgggcccaga gctggctttt   1500
ctctgtcacg gagagagaca tgagagggtc atgagtgtga agatcgccag ctcccagggt   1560
cagggcccag cctccttcca tctcactgct ctggactcct cagttcctca tggagtctgt   1620
ttagtgcctc tccagaaaag acaagttgaa gccctgacca ccagcatctc agagcacgaa   1680
ctcatttgga aatagggtca ttatagacgc aatcgatcag gtcagactgc agtagggcag   1740
gccctgaatc aaacatcatg gtgtcctcac aggtagagga gaggcacgag agagcaacgc   1800
tgcgtgaagc cgcaggatga gagcatcctg gaagatgggc acggctgggg tgacaggtct   1860
gggagcctgg gaacactggg aaagtcggcc agcactggag cctcccttag agctcgaaga   1920
aggagccagc cctgaccacc ccgactctga ccttctagca tcgaaacagg gagagacgca   1980
ttccacgtgg ttgttccaat cagcccagtt tctggggctt ccttatggca gcctcaggga   2040
actggcaaag cccaagtggg ctatcccatt acttatatct gggtaggtcc cagccacagg   2100
ggagagagaa gagaaagccc ctctatctaa tgacacgctg tactcatgtc ccaccgcat    2160 gatgtgccgt accgtgtcc ctatccaggt gacgtgccgt accgtgtcc cacccgggtg    2220 acgtgccgta cccgtgtcc accgggtga cgtgccgtac ccgtgtccca cccgggtgac    2280
gtgccgtacc cgtgtcccac ccgggtgacg tgccgtaccc gtgtccaccc gggtgacgt    2340 gccgtacccg tgtcccaccc gggtgacgtg ccgtacccgt gtcccacccg ggtgacgtgc   2400
```

```
cgtacccgtg tccctatcca ggtgacgtgc cgtacccgtg tcccacccag gtgatgtgct    2460
atgcccatgt cccacccagg tgacacgcta tacctgtgtc cctatccagg tgacacgctg    2520
tgccatgtcc ctatccgggt gacactgtgc catatccta tccaggtgac acacagtgct     2580
catgtgtcta tctagatgac agcaccgtgc ccacatcttt atcccggtga cagcactgtg    2640
cccacgtcct gtcttggtga catcactgtg ttatatacc tgtccatgtg acatcactgt     2700
gcccacatct gcctccaggt gacagcgctg tgcccacatc cccacccaag tgctctgggc    2760
accttggctg gggctctggc cactttcatg ttggtgccac cctgtgtgtg gatcatagca    2820
cccaggcact caccattacc gtggccagca cagaccagac ccgaccccag tagtcctcaa    2880
aactaggtcc cctgctgggt gcggtggctc acgcctgtaa tcccagcact ttgggaggct    2940
gaggcgggcg gatcacaaga tgaggagatc gagaccaacc tggctaacac ggtgaaaccc    3000
catctctact aaaaatacaa aaaattagcc gggtgaggtg gtgggcgcct gtagtcccac    3060
ctacttggga ggctgaggca ggagaatggt gtgaacccgg gaggcggagc ctgcagtgag    3120
ccgagatcat gccactgcac tccagcctag gggacagagc gagactcaaa aacaaaaaa    3180 acaaacaaaa aaaaactagg tccctgtgc tgtgctgctg tacccagca gtcgcttcac    3240 tggcaagact actcttagca ggtgcgcctg gaagcagaaa ctgggcagct cccggtctgt    3300
cctatacaca tgcaaatgcc ccattagaaa gcaaatagcc cgaggtgttt gcctgctccc    3360
aggcaaaatc tcccaaatct tcctccggga atcagtgaac agaagagatg tccatcaccc    3420
ccaggagagt agtgtctgaa cccgtctaac cgcccaacag gttctccctg ccgccggtct    3480
ggacagagct gctttatcac aacaggtgac ttgcaataaa gtttaattca cacagagtcg    3540
gccgtgcagg agaccagagt tttattatta ctcaaatcag tctcccagga aatttgggga    3600
tcaaagtttt taaggatcat ttggtgggta gggggcgagt caatagggag tgctgattgg    3660
ttgggtcaga gatgaaatca tggagagtca aagccatctt tttctgctga gtcagttcct    3720 gggtggggc cacaagacta gatgagccag tttatcaatc tggggggtgc cagctgatcc     3780
acccagtaca gggtctgcga aatatctcaa ccactgatct taggttctgc aacagtgatg    3840
taatcctagg agcaatttga ggaggttaaa aatctttcag cctccagatg tgtgactcca    3900
tgactcctaa accataattt ctaatctgtg gctaatttgt tagtcctgaa agtctagtcc    3960
ccaggcagga agagggtctg tcctgggaaa gggctgttat tgtctttgtt tcaaagataa    4020
actataaact aagttcttcc caaagttagt ccagcctgca cccagaaatg aataagaagg    4080
caagacagag ttggttacgt cagatctctt tcattgtcat aatttctgt tatatatttt      4140 ttttttttg agacagagtt tcgctcttat catccaggct ggagtccaat ggctcgatct     4200
tggctcactg caacctccac ctccggagtt ccagtgattc tcctgcctca gcctcccaag    4260
tagctgggat tacaggcgcc caccaccatg cccagctaat ttttgtattt ttagtagaga    4320 tgggattttcg tcaggttggc caggttggtc ttgaactcct gacctcaggt gatccaccca    4380
cctcggcctc ccaaactgct gggattacag gcatgagcca ccaccgccgg ccgatttttct  4440 gtaataattt ttgcagaggc ggtttcacca ggagaaccaa gcattaatgc gctgtggctg    4500
atgtgtagta gagcggcatt tcccaatggg agaaccctgg ggctgtctag agcccatgc     4560 atggctggga gcctaatccc agggacacca ccgatgacag ctcccatagc acgtaggaca    4620
gtggatactt ggaggcaaag agaaatctct gttctgcagt ggtcatgact tggaccccaa    4680
agaacttgag cccaaggtcc agagggagac cctcccaaca gggcctccag caggaacagg    4740
gatcgtggga gcctgccaag cacagcgcac aggtatttct ggaggcttcc cattcagtct    4800
```

```
tggatgccag cctcaccgag ggcggcccat cttgctgacc tcaccaaggg aggcccgtct    4860
cactgccctg atggcgcaga atcggctgta cgtgtggaat cagaagtggc cgcgcggcgg    4920
cagtgcaggc tcacacatca cagcccgagc acgcctggct ggggttcacc cacagaaacg    4980
tcccaggtct cccaggccag gtgccgcatt ggttcccgag ggttgtcaga gatagacact    5040
catgcgacta acatcgggct atgtgtttga ttcaccccag ggtgcattgt tgaaggttgg    5100
ggagattgga ggagatgctt gggggacaat gaggtgtccc agttccttgg atgatagggga   5160 tctcggccta agcgtgagac ccctcctaca gggtctctgg caggcacaga gcctgggggc    5220
tcttgcatag cacatgtgta tttctggagg cttcccctttc ggtctcaccg ccccgatggt    5280
gcagaatcgg ttgtagttgt ggaatcggaa gtggccgcgc ggcggcagtg caggctccca    5340
catcacagct caagcccgcc ccagctgagg ttcacccgcg gaaacgtccc gggtcacgca    5400
agctaggtgc cgcaaggttc acgggggtag tgagggatag aacactcatg ggagccacat    5460
tgggctacgt gtctgattca ccccaggggt cactattgag ggttggggag atgagatact    5520
ttggtgacaa tgaggtgtcc ccattctttg gatgatgggg atctcggcct cagcgtgagg    5580
cccctcccac agggtctctg gcaggcacag aaactggggg ctcttgcgta gcacatgggt    5640
atttgtggac gcttcccctt ctgtctcacc acccggatgg cacagaatcg gttgtaagtg    5700
tggactcaaa agtggccgcg cggcggcagt gcaggctcac acatcacagc caagccctc    5760 cctggatggg gttcgcccgc ggaaacgtcc tgggtcaccc aagccaggtg ccgcagggtt    5820
ctcggaggtc ttctgggaat aggacgctca tgggagccac accacgtctt cgtatcgggc    5880
catatccacg gccgcgtggc cccaggtcac actctgaggg cttcagtgtc atggcctggg    5940
actcaagtca cgcctaccca cgtgatgagc acagcaaatt ccgccaaaag cttatacttt    6000
ccacatccat cccagagcac agatccgact aaggacagcc cccaaatccc gagcctttt     6060 ctgaactgac aattgcctcc ccagtgaaca ctctgagctt gtcaatctta agtggccaga    6120
cattaacatt cccattcagt gcaggtttga gatgctaatt taggagcttg agatgctaaa    6180
gagctgggag tgccactgct gctttattct ggggtctagg atccttgtgt tggctgagat    6240
aatctgctaa tgtgggtgca gcagacatcc cgcggtttgt ggaatcgata aaggatgggg    6300
atcaatggtg tttgtgcact gtgcggtctg tgcccaattg cctgccttgt gctgtggaat    6360
ctgtacatct ggccaacatg tgcttgtgtg agcctgacag tgcattttcc agagcctcac    6420
ctcggctctg ccctggaggc tctgtgctgc tggaatcaga ctcaaggacc tcatcagagg    6480
accatggccc cgtatcacct gggtcaggca ctgaagctgg acaggagag cagagacttc     6540 caaaatgagg gatccctgtg ttctgaggtg atcatgactg ggacccaagg actcaagcgc    6600
atgctccaga gggaatcgtt tcccacaagg cctttggcag gaacagggat cctgggagcc    6660
tgccaagcag agcgcacagt gttcctggag tctcgctgcc cagatgccac ggaatcagtt    6720
gaaggtatga aaacacaggt ggccacgtgg tagcagggca ggctcaggcg tcatagcccg    6780
agcccggcta cctgtggttt gcctgcagaa acatcccggg tcaacaggcc aggcaccgca    6840
ttggttcgcg agggtcatcg ggggtaggac ccttgtacga gccacatcgg gctacgtgcc    6900
tgattcaccc cagggtgcac tgttgaaggt tggggagatg agaggagata cttgggggac    6960
agtgaagtgt ccccattctt tggatgatgg ggatctcggc ctcagcgtga ccccctccc     7020 acagggtctc tggcaggctc aagagcccag ggctcttgc atagcacatg aatatttctg     7080
gaggcttccc cttcagtctc accacccgga tggtgcagaa ttggttgtag ctgtggaatc    7140
ggaagtggcc gcgtggcggc agtgcaggct cacacatcac agcccgagcc cgccccagct    7200
```

```
ggggttcgcc cgcggaaacg tcccgggtcc cgcaagccag gcgccgcagg gttcacgggg   7260
gtcatcaggg ataggacatt catgggagcc acatcgggct atgtgtctga ttcacccccag  7320
ggtgcactat tgagggttgg ggagatgaga ggagatactt gggggacaat gaagtgtccc   7380
cattctttgg atgatgggga tcttggcctc agggtgagat ccttcttgca gggtctctgg   7440
caggcacaga gcccgggggc tcttgcatag cacatgtgta tttctggagg cttccccttc   7500
agtctcaccg cccggatggc acagaattgg ttgtagttgt ggaatcggag gtggctgcgc   7560
ggcggcagtg caggctcaca catcacagcc tgagcccgcc ccagctgggg ttcgcccgtg   7620
gaaacatccc aggtcatcca agccgggcgc acagggttc  acaggggtcg tgaggtatag   7680
gacactcatg ggagccatat cgggctacgt gtctgattca ccccagggtg cactgttgaa   7740
ggttggggag atgggaggag atactagggg aacaatgagg tgtcccagtt ccatggatga   7800
tggggatctc ggccctagtg tgaaacccctt ctcgcagggt ctctggcagg cacagagccc   7860
gggggctctt gcatagcaca tgggtatttc tggaggcttc tccttcggtc tcaccgcctg   7920
gatggcacgg aattggttgt agttgtggaa tcggaagtgg ccgcgcggcg gcagtgcagg   7980
ctcacacatc acagcccgag cccgcccccaa ctggggttcg cccgtggaaa cgtcccgggt   8040
cacccaagcc acgcgtcgca gggttcacgg gggtcatctg gaataggac  actcatggga   8100
gccgcaccag atcttcaggt cgggcattat ccacagcccc gtggccccgg gtcacactcc   8160
gagggcttca gtgtcatggc ctgggactca agtcacgcct acttatgtga tgatcacagt   8220
gtgttccacc aaaatcttac attttccaca tctatcccag agcacagctc cgactccgtc   8280
taaggacagc ccccaaatcc ccagccttt  actgaactga caattgcctc cccagtgaac   8340
actctgatct cctcagccct aagtggccag acattaacat tctcattcaa tgcaggtttg   8400
aggtgctaat tcaggagctt aagatgctaa agagctggga gcgccactgc tgctttattc   8460
tctggtccag gatccttgtg ttgctggaga taatccatta tcgtgggtgc agcagacacc   8520
ctgcggcttg tggactcggt acggggtggg gatcctgatg gggttaggat gttcgatggc   8580
tcgggtgtgc tccacgctca gggatcatca cgtccggccg gcggtagttg gcacgtggag   8640
aggtgaattt gcccacaggt gttccccgtg cctgcgcatt gctggcagca cgaccggatc   8700
ctgtgctagc ccctcccaca atgcctggag caggagcgag gggcctgggg agccgccttg   8760
cctggagcat ttgtatttcc ggagtatttc ctgagtctcc ccttgggtct tgggtgctgt   8820
ccccagtgag cccatctccc agcgatggca cagaatcggt tgtggctgtg gagacggaaa   8880
tggccgagag gcggcagtgg tgactcacat cacagtctga aggtgaccca aggctggact   8940
ccacttttag caaaatgtgg gggtctgcct tggtctccta acttgggggt ccactcatgg   9000
aaaagcctga gaatttttcat gccatggaaa ttccccccatg tcgtgggtt  cacgcacgac   9060
aaagcccggc ggtcagtgct cagcaggcaa gcactcagcc ttttccggtg gggccatggg   9120
aacagagggt ttgccgaagg cgcggccagc ccttccacat cccagagggc ctgctgggtg   9180
attggacccg tgaactctgg gtcccttggc cctggtgctc cccttcacgg ctttgacact   9240
cgagacttga ggtgaacccc agggactgca gggcccaac  aaccctcacc aaaggccaag   9300
gtggtgaccg acggacccac agcggggtgg ctggggagt  cgaaactcgc cagtctccac   9360
tccactccca accgtggtgc cccacgcggg cctgggagag tctgtgaggc cgcccaccgc   9420
ttgtcagtag agtgcgcccg cgagccgtaa gcacagcccg gcaacatgcg gtcttcagac   9480
aggaaagtgg ccgcgaatgg gaccggggtg cccagcggct gtggggactc tgtcctgcgg   9540
aaaccgcggt gacgagcaca agctcggtca actggatggg aatcggcctg gggggctggc   9600
```

```
accgcgccca ccaggggggtt tgcggcactt ccctctgccc ctcagcaccc caccccccact    9660
ctccaggaac gtgaggtctg agccgtgatg gtggcaggaa ggggccctct gtgccatccg    9720
agtccccagg gacccgcagc tggccccccag ccatgtgcaa agtatgtgca gggcgctggc    9780
aggcagggag cagcaggcat ggtgtcccct gaggggagac agtggtctgg gagggagagg    9840
tcctggaccc tgagggaggt gatggggcaa tgctcagccc tgtctccgga tgccaaagga    9900
ggggtgcggg gaggccgtct ttggagaatt ccaggatggg tgctgggtga gagagacgtg    9960
tgctggaact gtccagggcg gaggtgggcc ctgcggggggc cctcgggagg gccctgctct    10020
gattggccgg cagggcaggg gcggggaattc tgggcggggc caccccagtt agaaaaagcc    10080
cgggctagga ccgaggagca gggtgaggga gggggtggga tgggtggggg gtaacggggg    10140
aaactgggga agtggggaac cgaggggcaa ccaggggaag atgggggtgct ggaggagagc    10200
ttgtgggagc caaggagcac cttggacatc tggagtctgg caggagtgat gacgggtgga    10260
ggggctagct cgaggcaggg ctggtggggc ctgaggccag tgaggagtgt ggagtaggcg    10320
cccaggcatc gtgcagacag ggcgacatca gctggggacg atgggcctga gctagggctg    10380
gaaagaaggg ggagccaggc attcatcccg gtcacttttg gttacaggac gtggcagctg    10440
gttggacgag gggagctggt gggcagggtt tgatcccagg gcctgggcaa cggaggtgta    10500
gctggcagca gcgggcaggt gaggacccca tctgccgggc aggtgagtcc cttccctccc    10560
caggcctcgc ttccccagcc ttctgaaaga aggaggtttta ggggatcgag ggctggcggg    10620
gagaagcaga caccctccca gcagagggggc aggatggggg caggagagtt agcaaaggtg    10680
acatcttctc gggggggagcc gagactgcgc aaggctgggg ggttatgggc ccgttccagg    10740
cagaaagagc aagagggcag ggagggagca caggggtggc cagcgtaggg tccagcacgt    10800
ggggtggtac cccaggcctg ggtcagacag ggacatggca ggggacacag gacagagggg    10860
tcccagctg ccacctcacc caccgcaatt catttagtag caggcacagg ggcagctccg    10920
gcacggcttt ctcaggccta tgccggagcc tcgagggctg gagagcggga agacaggcag    10980
tgctcgggga gttgcagcag gacgtcacca ggagggcgaa gcggccacgg gaggggggcc    11040
ccgggacatt gcgcagcaag gaggctgcag gggctcggcc tgcgggcgcc ggtcccacga    11100
ggcactgcgg cccagggtct ggtgcggaga gggcccacag tggacttggt gacgctgtat    11160
gccctcaccg ctcagcccct ggggctggct tgcagacag tacagcatcc aggggagtca    11220
agggcatggg gcgagaccag actaggcgag gcgggcgggg cggagtgaat gagctctcag    11280
gagggaggat ggtgcaggca ggggtgagga gcgcagcggg cggcgagcgg gaggcactgg    11340
cctccagagc ccgtggccaa ggcgggcctc gcgggcggcg acggagccgg atcggtgcc    11400
tcagcgttcg ggctggagac gagggtgagt ttttccccct ctgccaccct cagccccac    11460
ccgcccctcc ccacacaacc aacacgttct ccccacacga ctctctcgtt ctccccacag    11520
ccaggtctcc agctggggtg gacgtgccca ccagctgccg aaggccaaga cgccaggtcc    11580
ggtggacgtg acaagcagga catgacatgg tccggtgtga cggcgaggac agaggaggcg    11640
cgtccggcct tcctggtgag cgtgtctgcc ctccctgcgt caggacgcgg ccctgccag    11700
accgccccgg cgcgccacca tctcactgcc ccgacctctg tcttctacag aacaccttag    11760
gctggtgggg ctgcggcaag aagcgggtct gtttctttac ttcctccacg gagtcggcac    11820
actatggctg ccctctgggc tcccagaacc cacaacatga aaggtgaggg gcttcctgcc    11880
acacttgggg tgggggcac gcgagaggag ctgagtggga cctcaactcc ttccccatcc    11940
acagaaatgg tgctacccag ctcaagcctg ggcctttgaa tccggacaca aaaccctcta    12000
```

```
gcttggaaat gaatatgctg cactttacaa ccactgcact acctgactca ggaatcggct    12060
ctggaaggtg agcaccagcg ctccttccgg aagcctccag gcccccgagc accctgcccc    12120
catcccaccc acgtgtcgct atctctaggt gaagctagag gaaccagacc tcatcagccc    12180
aacatcaaag acaccatcgg aacagcgcg cccgcagcac ccaccccgca ccggcgactc    12240
catcttcatg gccacccct gcggcggacg gttgaccacc agccaccaca tcatcccaga    12300
gctgagctcc tccagcggga tgacgccgtc cccaccacct ccctcttctt cttttcatc    12360 cttctgtctc tttgtttctg agctttcctg tctttccttt tttctgagag attcaaagcc    12420
tccacgactc tgtttccccc gtcccttctg aatttaattt gcactaagtc atttgcactg    12480
gttggagttg tggagacggc cttgagtctc agtacgagtg tgcgtgagtg tgagccacct    12540
tggcaagtgc ctgtgcaggg cccggccgcc ctccatctgg gccgggtgac tgggcgccgg    12600
ctgtgtgccc gaggcctcac cctgccctcg cctagtctgg aagctccgac cgacatcacg    12660
gagcagcctt caagcattcc attacgcccc atctcgctct gtgcccctcc ccaccagggc    12720
ttcagcagga gccctggact catcatcaat aaacactgtt acagcaattt gtctcgagga    12780
ctctggaatc cggctgtgg gcatgatgtg ggggaggcca gccttgggca gagggggct    12840 gggggcatg gggaggagta catgaaaagg gggatggggg ttccagggtg ggggattctg    12900
ggatgggtgc agcgcagcac acaccagggg tggggtgagc acagggtgtg tggacctcag    12960
gggtgcaggg caggcggtca gcatgcagtg atggcagtgg aggggctgtg ggaccagggg    13020
cttcacagac tgggcggggg ctgggcttgc ggaggggcc tgcgctctga ggcagggtc    13080 ggggaccacc aaaccatccc cgagcgagtg cctcctgtcg ccccaaagtc ccatcagaat    13140
gacgccttgg tgctggcccc agaccccctga agcccgggct aggtgactgg ggtagagctg    13200
gccatggccg ctctgggagg cccacaaggt gctctgggcg accccacccc gacagggggca   13260 cgaacccgc gccagtcccg ttcctgctcc ccttttgctg tgggtgggag ccggggccac    13320
gccggaggga cggccccgca caaggagcca gggggttggg ggggagccgg tgggcttctc    13380
agtgggcagg tggccttggg gcagaggtcc taaggaggcc aggggaccag gaggagggag    13440
gaaggagttg agggtggcca cagggaggag gtgaggagga gcgggagggc ccagggtgag    13500
gggctcccgg gctccctccc cggggtcttg ctgctggagc tccaagaacc ccggtatgca    13560
ggggttcgct cccaggtgc caaggcagcc cactcatggg ttcggggtca gcttccccgc    13620
agaggccagt ggccggcagc tccctcagcc aggcctccca gctcctggcc cctcgctgtg    13680
caggcgctgg gaacacaagg ggcagcccct ggaaataagg gtgggtccc ggcctcccca    13740 ttccttcccc cctccccct gccttccacc cccattccca gtgcacagag ctgtcaggaa    13800
aattcctccc cgactgacaa agaacagaca ggaaggcggt tagggacgcc cctcccctac    13860
cggcccagcc gcccttgggg tcttggtgtc cagggcggaa gagcagggtg gttccccacg    13920
cccccttggg ctggcctccc ctctgcaccc tctcttgccc cctccccatc cagctgtggg    13980
ccctggggac tgtcagagac cgaggggttt ccagggacac acttgtgtgc taaaacctgg    14040
gcgggtggtc accccccagg atgcatgtag acatccggtg agggagtctc ttgaagtctc    14100
tgggatggtg cccctgggac tggctgccat ctcatggagg aggtcagagg tcgctgggc    14160 cagcccaggt tgaggccgca ttcatcttcc tgacccctaca ggccaatttg acttacccaa    14220
gtgggttttg gccggcagga tgaagtaacc catccattac atgtcaagag ttaggtctat    14280
aaacggcctt tattataaac atccaactct gcaggaggtt tacaaagcag ggctcaggag    14340
ataaaagccg gcttccccag gtggcggctg cagggtgcgg caggcagccc cagggtgcc    14400
```

```
cagggtggcg gggcagggga accgtaggga gggggagagg ggcacccaga aaacctctcc   14460
tggggaacat ggaagactct gcccacttca aatccctgcc tggggaagga cacatgggaa   14520
tggggccggg ggaaaaggcg ggccacctcg ggccttcgtc acctgtgtca gctcctaggg   14580
attgtctcct cctggtcact tggagagaac aggcgtgctg gacacgtcca catctctggg   14640
cccaggggtg tatgaatgac acgcttgctc tggagtttcc acctgggagc tgtatgggga   14700
cagggctgtt cctcctcaca cccgctgggg aagggacaca ggcctcttgg tggccccac    14760 catctcccag cactgcccat ggctgtgccc acgctggctg ccccctgaga gcaggacgtg   14820
tactcagggg cagcgcctac ctctgggcag cccaggtttc tctgctccct gcagcggaac   14880
gggcttccta gggcagttcc tggggtggtg tccctagggc agcccctgag tgctggaggg   14940
ggtctgcgcc acaggccctg aaacaggag gtggtggggg cagcgttcag ggggctgaac    15000
ctcagggtga ggcgggcagg cggggagcca caggcccggg ggccccgcag caggtgctca   15060
gcctcggagc ctcctgccgc accccggggc ggggctggg agcccgcccg agcccctagc    15120
tctgagcgac ctgccaggtt ggaatgtgtg tttatctttg gcccaacccg atttcctgct   15180
ttttagaaaa ggggcttaga gagggttgtt agacaggctc caggcacccc aacacccaaa   15240
ggcactttga aaacgcccct gcactgactt cagtgcggag aagcaaacgg gctggaattt   15300
cactcccaaa ccccaacatg ggggtggcgg ggccggggtg agggttgtgg ctgcctgcaa   15360
aggtgccagg aaatctgggg agggaggaac ttccaccgtt cagggagacc ctgagggtgc   15420
cctggcttct ggccacgtcc cagaccctgt taggcaccga ggtcttcaca cccagaccct   15480
ccacccaccc aagtttctgc ggcacgttta ggttgagtga agaccaagtc atccagttag   15540
agaagaggac ttgaggcgcg tgctgctgct gtggccacgc tggacctcgg tgcacgcatc   15600
tcctggcgag tccctgaga tggcctgtgc agccatacac acccggggca cgcgacctca    15660
gctacctcgt caccgaggac gtgcatccac agctgtgcgt ctgtgcctgg gagcggggtc   15720
tccacttggt gggtctctgc atgctgacca gttaacccgc cttccgggc tgtggagggc    15780 gtgggtcctg tccggcccgg agatgctccg cggggtgtgt gtgtgatcgt ggccctgtag   15840
cggggtggtg ttccctggag ggtggacccc tgagcctggc tgtgtgtggc tcgtgtctca   15900
gcatgaattc cgtgacccag gagcacgttt tcaggcaggg attaggggca gctgggtgtg   15960
ggaggcaggc acttggtata ccaccgaatg gagacagaaa atcccaactc tacgaaggaa   16020
gtgaagtccc ttcaacaggg acaaagcgat gttttgggtc tgactacaat gcaccctggg   16080
aagtctcaaa gaaaacagtc gggtactcaa ggagggcagc cccctctccc cgaccccgag   16140
ctcccaggaa gataaatgat ttcctcctct ctagagatgg gggtgggatc tgagcactca   16200
gagccaaggc cgcagtgggt ccgggcgggg gccctcctcg gccctcccaa catgggggcc   16260
aggaggtcag cccctcaacc tggacccccgg ctgggtctca gggaatggtc tcccccagtg   16320
gcccagcttg cttgttttca gatgggtgtg cacgggtgtg tgtgtgtgtg tgtgtgtgtg   16380
tgtgtgtgtg tgtgtgtgat gcctgacaag ccccagagag ccaaagacct gagtggagat   16440
cttgtgactt tcaaaaggg ggattggaag gttcgagaag gagctgtggt cagccttgct   16500
ctcccttaag gctgtggtaa ccacactagg catagcatag gcctgcgccc cgtccctcct   16560
tccctcctcc gcgcctctcc tttctctttc tccccctct accccgctcc ctggcctgct    16620
cctggtgaca ccgttggccc ccttccaggg ctgagggaag ccagcggggg ccccttcctg   16680
gaagcccacc tgcaggccgg cttgctggga aggggctgct ctcgcagagg ctcccgcccg   16740
ccctgcagcc gtttcctgga agcagtcgct gtgggtattc tgttccttgt cagcactgtg   16800
```

```
cttgcaaaga aagcagacac tgtgctcctt gtccttaggg agccccgctc catcacccaa   16860
cacctggctg gacacaggcg ggaggccggg tccgcgggga gcggcgcggg gctggggccg   16920
gaccagtaaa cacacacggg cgccaggcac tgcaggctcc tcctcctcct cctgcccagc   16980
gcctctgctc acaggcacgt gccaagcccc taggccagga ggcccagcag tgggtgcaga   17040
gcaagctcct gggaaggggg tgcagggcgg accccggggg agaagggctg gcagggctgt   17100
gggggacgct gaccgtgggc cccacgttgc agaaaactgg ctgcctggct ggaagatggg   17160
ggagatgcca agcctctgag gcagcacgag cagggtgcat ggaggccggg gcgcggggag   17220
gctgcactgc agcatgcacc ccaaagccca gaggagtgg agaccaggcc ctggaatcga   17280
gaagtagaaa ggcggcttgg aggcctcgga accggctgac ctccaacaga gtggggccgg   17340
ccctggaggc aaagaggtgc ccgggtccg gccctgcctg ggggagctat gtgtcatggg   17400
cagccacagg atatgtagcc agctctgagc atggaccc agggcagggc tgcaaggcag   17460
ggcaggggaa acagacgggg gagcaaggag cagagagggg gcctcaggct ctcccaggag   17520
gaacattctc ccgacaggag gaagagacgg cccagggtg actgtgggga gccatggtgg   17580
cagctggggt cgtggcagat gggagagagg ctggcgaggt gaaggtgcag gggtcagggc   17640
tctggggccc acatgcctgt gggagcgggc aggcccaggg ctctccgcca ctccccactc   17700
ccgcttggct cataggctgg gcccaagggt ggggtgggat gagcaggaga tggggcccag   17760
ggggcaagca gggccccaaa gacatttaga aaaaccggtt tatgcaggca gcattcagag   17820
caggcggcgt gcgtggcggg ggccctggga gcacagagag gcacgtag ggcccccgag   17880 gggctcccca ttggccggca gtgacatcac ccctgtgtca acagtgatgt ctgcagctcc   17940
ggccagccag ggtttatgga gcgagaccca gcccggcctg ggcctcact ccccaggccc   18000 acacactagc ccactgttca gggtccgggg tggcggcatg gcctgggggt cctggcaccg   18060
ctgctcctct gcccacccta acttcccggc atggcggctg ccccctctga gcgtccccaa   18120
ccagtaagtg tggggccagc aggcctgccg tcctcctcct cttccctcta gagagaaacg   18180
tggaggtcct ggggctgggg gcgctcatag ccctgtgaca caggtgcatg gggtcagggg   18240
tcccagaatg gcccctggga aggacctcag ctgggccggc ggctctaggc ttcaggggtc   18300
tgtctgcaca gggggctagcc cctcccagac ctctgtgaag ccagtacggg cctcccctcc   18360
ctgccccgtg ctctgtccgg tgcttcctgg actgcactgc gggccactgg tgagagggtg   18420
gacagggaag ggccgccgtg gtgcctgttc ctgcccacct ggctgtgtgg tcccctccaa   18480
gtagggacaa cccttctgag ggcttggggg caccctgggg ttgccaggc ctcccagagc   18540 cctgtgagcc cctgggggt ctggcctgat gccccctcc acgtccaggg ccggctgtgg   18600
cccagaaccc cagcttccca gcaggccggt gtgcggtggt gacccaggag aggcctcgcc   18660
tccactgagg ggccaccgac ctctgccagg ccacagagac ccccaaggag tctgaaggct   18720
ggagacccgg ggctgggacc agtgggact ttcccacgga gccgtcccca ggcccagctg   18780
gggacacgtc cccccttctct ccagacacac cctgcctgcc accacgacac accggcctgt   18840
tgggggtctc ttttaagtgc ctgccactct gaggtgactg tcccttttcca aagaggtttc   18900 tggggcccag gtgggatgcg tcggcctgag caggaggatc tgggccgcca ggggctgggg   18960
actgtctcct ggggaaggaa gcgcctggga gcgtgtgtgc tgacccagga ccatccaggg   19020
aggcccgtct gtgcggcaag cgggaaggga gcggctggag aggcttggcc gccccgccc    19080 tgcctcccat tccttagctc cctgcctgtc aacctctgtc acccagtgag tgatgtccag   19140
gggccctgga aaggtcacag catgtttgag cggggtgaga gagaggggaa aggcggggc    19200
```

```
ggggaaaagt acgtggagga agctctaggc ccaaggaagg agaaagggtt ctgggaggga    19260
gggagccact ggggccgccg ggagggtccc tgcctgctgc tgccacccag aaccctcgcc    19320
tcttagctag cccccgcagc cccagccttt ctggcctgtg cccctctccc ccatccccag    19380
ctgtcctgtg caaccaggcc ttggacccaa accctcctgc cccctcctct ccctcctcac    19440
cctcccaatg cagtggtctc cagcctggct ctgccctgcc gcaggtcccc tcccctcatt    19500
ccaggcctag agcctccagt cccggtggcc cccagcccga gggtgaacgg cctcaccctg    19560
ggtcgtggga cagagggcac gttcatcaag agtggctccc aagggacacg tggctgtttg    19620
cagttcacag gaagcattcg agataaggag cttgttttcc cagtgggcac ggagccagca    19680
gggggggctgt ggggcagccc agggtcaagg ccaggctgtg gggctgcagc tgccttgggc    19740
cccactccca ggcctttgcg ggaggtggga ggcgggaggc ggcagctgca cagtggcccc    19800
aggcgaggct ctcagcccca gtcgctctcc gggtgggcag cccaagaggg tctggctgag    19860
cctcccacat ctgggactcc atcacccaac aacttaatta aggctgaatt tcacgtgtcc    19920
tgtgacttgg gtagacaaag cccctgtcca aaggggcagc cagcctaagg cagtggggac    19980
ggcgtgggtg gcgggcgacg ggggagatgg acaacaggac cgagggtgtg cgggcgatgg    20040
gggagatgga caacaggacc gagggtgtgc gggcgatggg ggagatggac aacaggaccg    20100
agggtgtgcg ggacacgcat gtcactcatg cacgccaatg gggggcgtgg gaggctgggg    20160
agcagacaga ctgggctggg ctgggcggga aggacgggca gatgggatcc caaggacatg    20220
gaatttcgga ccttctgtcc ccgccctctc tgctgagcct aggaacctct gagcagcagg    20280
aaggccttgg gtctagagcc tagaaatgga cccccacgtc cacctgccca gcctagaccc    20340
ccagcattga agggtggtca gacttcctgt gagaggaagc cactaagcgg gatggacacc    20400
atcgcccact ccacccggcc ctgccagcc ctgccagtc cagcccagtc cagcccagcc    20460
ctgcccttcc cagccctgcc cagcccagct catccctgcc ctaccagcc cagccctgtc    20520
ctgccctgcc cagcccagcc cagcccagcc ctgccctgcc ctgccctgcc cttcccagcc    20580
ctgaccttcc cagccctgcc cagcccagct catccctgcc ctaccagct cagccctgcc    20640
ctgccctgcc cagcccctgcc cagcccagcc ctgccctgcc ctgcccagct cagccctgcc    20700
caccccagcc cagcccagcc cagcatgcct tctctggctg gagagcacag gcttgaccttt    20760
agaaagaggc tggcaacgag ggctgaggcc accaggccac tgggtgctca cgggtcagac    20820
aagcccagag cctgctcccc tgccacgggt cggggctgtc accgccagca tgctgtggat    20880
gtgcatggcc tcagggctgc tggctccagg ctgcccccgc cctggctccc gaggccaccc    20940
ctcttatgcc atgaaccctg tgccacaccc acctctgagc tgtccccgct cctgccgcct    21000
gcaccccctg agcagccccc tgtgtgtttc atgggagtct tagcaaggaa ggggagctct    21060
tcaatcttgc cagtcagggt gctgtctgct gagtaagtgt ccccgtgctg tgccccaatg    21120
tccccatcct ttggcaaaca gccatcagcc tgtggatcct gcactccat gcggtgggag    21180
agggagacct gggctcacct gagcctcccc acaagccagg gagagggct gcccaatggc    21240
gggaggcccc catggatccc aaacggcagt tgcccgcact cctacccagg aactttgtct    21300
gtgatgaaca gtaaggaata aggaagcggg tgagaaagaa ggaaggaaag gcggtggggg    21360
gcatggcggg gggcggggag ggtgtttgga aagttccaga aaagagtcac ttcaccagaa    21420
aggccacaag ctccccgtgc ccccagcccc tgctcggctc cgaggtgaag gacttggagc    21480
gtcgacgctg gcgtggggac cagctgttct ccttgagttt gtttccttca gttccttccg    21540
ggcctcaccc tcctcttcct gccacacaca cacttttttc cttttttaaat tgttttattt    21600
```

```
ggggccaggt gtggtggctc acacctgtaa tctcagtatt ttagaaggcc aaggtgggca   21660
gattgcttga gtccaggagt tggagaccag cctgggcaac atagtgagac cccatctcta   21720
ccaaatatca gccaggtgcg gcggcgcgca cctgtattcc cagctatgtg ggagactgag   21780
gtgagaggat cacgtgagcc caggaggttg aggctgcagc aagccatgat cataccactg   21840
cactccagcc tgggcaagag agtgacaccc tgtctcaaaa aaaaaaaaaa gtagaaaaat   21900
ttattttaaa aaattgtttt aacatttgag tgctgcaact gtccaaggag gagcagacgg   21960
cccgtgtcag acagcctgaa gcctgactgt ctgcgatcaa cggccccgtg ccagctgtg    22020
tgcagcagtt tggcctggcc tgatgcctct gtccttggca ccagctcaca gcccgtgccc   22080
ataacagacc tggggcaccg aaggaagggc agatccagcc cccacctgcc ctgggtctga   22140
agatctccca ggaggctcca tggggtgcct tgagtgggag gggctggccg atagccttga   22200
ggaattggca cggacatgca gagaggggca tgtcccaaac tcgggcgct gtggcctcca    22260
gctgccagga ggtagatgtg ttctgacttc tgggttccca ccaccagaac tgcagggggat  22320
atgaagcaag ctggacttgg ggagacatct ctgctcgagt gcacgttggc ctgatgacga   22380
ctgctcttgg gttcacgggt tccaggctct gcccgggagc ctcatgcaaa ctggtcccgt   22440
tctacagatg aggaaactga ggcacagagt gattacggct gtccctgagc tcctgcagcc   22500
agtaaggtga tacaccagga tgtgttccca ggttgtccgc tgggctcagt aacacagtct   22560
caactgccct gtgacactgc gtgtctgtgc ttgtggggaa ggtgaccaga ggccccttt    22620
cctccacgcg gtgagcctac cagcaaggag acagtcctca ggtgtgagga tgagcctcgt   22680
agtaggcaca gagaaacagg aggaaccttc tggaaggtga agcctcccac ggctgggact   22740
cttggagaag ggcggatctc tgtccactcc tgcccactcc ccagcacaga cagagcaagc   22800
aggacagagg gcccaacgtc ccaggatact gcagagctca aggagggca gagagcatcg    22860
ccccacatgg gcgccgggag aaaggtgggc ggggtgctca ggggcccctg gccgtcctga   22920
agtttgcctc agagaggtgt gggcttctcc tccctcccat acacagtgtc tctgaggatg   22980
aactgccatg tgcccggcgg ggatgccgtc cctggcccct gctgagtgcc tctgggacga   23040
ggtcagctga gcctgccatc ctaactcaga caccatctca ctctccaagt cccttctcgg   23100
tgagacgggg ggccttgcac ccacctccca gccccacac acctgagggg gtccccgttc    23160
ccctaccccg tggctccacc acgccccacg catcctacct gagggacaga ggggactgtg   23220
agatgccccc cacaggctgg ttttcctctt tcacccataa caggcccagc aaattctcac   23280
ctccagaggc caggtctgcc ccgcaggtct taggaaatac agccctactt ccatccagca   23340
caccaaccca aggaagtgcc tcggagcccct ggggcccgag gggggcctgg ccttggtctc   23400
acggcggcag ctccacctgg agaggagtga actcaagcca ggacgccccg tctccacagc   23460
ggaaaccgtg ttgccggctg ctccctcctg gggactctgg gcctgaggtt cctgtgggag   23520
ttgggggat agctgagtcc tatggagtg ccctctcct ccccgcccag tggagcttgg      23580
ggtggggaca ggcgaagaca gggtgagaag cacggggcat tccccctcca cacagcgctg   23640
agaaagtaag ggagcatcca gaaaacggtg cccacttccg cgtcaggcgg atatcacggg   23700
caccagctcc aggtgaccct agcccagcca gagaacaagg accaggttgt gccgcaaagc   23760
ccgtgtccgc tccctcccgc ctgggaccac tgtggcgagg ggaagggagc gtggtggccc   23820
tctcctgact cctgaggcct gaagtccaag ctcccggccc tcaggcaggc cagggtctag   23880
acaccgctgc cccaaacaca ccccccagtc ccgcccgca ggcttcctgc aggatccccc    23940
agtgcacctg ggggctgagg agagtgagca gggcgcaaag aagcttcgtc gggagggcgg   24000
```

```
tccccacccg ccttggaccc ccggggatag tgtcctgggg cctgggctca gatggaccct   24060
gggaggaacg gtgcgggggc tgttttttgc tccaagagaa cattgcctca gcagagggct   24120
gccgagctgg gaggacccac agtgcaaggc cgcacaaacc cctaggaagc ctcagagcct   24180
tcaggttccg ggctgaggct gtgggcgtgg accttgtgc aaaccccact ggaagaaaaa    24240
ccttacagct caggaggagg ggccccaccc gctcccagag cccgtaaacg aggggtggtg   24300
cccacatgag gcctggggaa gggctgggc tgggacaccc cctcaccacc ccagatacc    24360 ccagcagcc cctccctcca cagagagacc cactgggcct gaccctgccc tgggcacagg    24420
gtcgagccag ggacgcccg tgggagaaag acggcttcat gggccgctgg ccgggccagg   24480
tgcgtccttc cccagttcta ggtggcaaat ggggtggggc cagagccttc tggctaggga   24540
agacactggc ctggttggtg tggcagggc agcgaaggag ggtcaaaggc cactctggcc    24600
tggaagagtc cccagccacc tggacggggg tagccaggcc tggtccctgc ccccactctc   24660
caaggggtcg gggcagccgg gcagagccag taagtgtttg ttttcagatg acatttgtaa   24720
agaaaaacag cctcccacac tgcttgaccc tgtgtctgga atgtggggag gcaaacagct   24780
gtgcccttcc cagaccctgc acagcccctg gtggggcag ggccctggtg ggagcagggc    24840
ccagaggtac agcctgggga ggcaccggcc attgtggttg gagcgcggca gccaggctct   24900
gggctctgtt ccgggcctca ctgtgtcccc agtggggtgc cgccaccacc ccccagcct    24960 gggccccgcc ggtcagacac ccgcagggac agcttgtctt ggctagctgg ctacagcacc   25020
tcgctggagt ccagcagaca cgcgctcccg tgcgcacgct gcgccccagg ccagccctaa   25080
cgccgctgct cgggtcaggc ccccgcctg ccgtgggctg ctggctgcct tggcccgccc    25140
cagctctctc cgcgcccctg cctccaggga gccctcctcg aggactccag ccacccaagc   25200
tcagcagggc cagcccgagc ccctgcccca cccagcctgt gtggagggtc ctcagccccc   25260
tgatccccca gaccctcccg gcagaagctg ggtccctggg gcttggggaa agccggctcc   25320
atggcccctg gcctggatga tttcccagag gccggtcccc tgccaagtgc ctggtgaccc   25380
ttgttcctac ctggctgccc atggtccttt gtgcgacccc cgcccacagc ccaggagctg   25440
ggcaggagac tctgattggg tggcagcaga gccatcctag gggtgcccct gaccctggcc   25500
ctgaccctgc cctggagcct cgtttccaaa tcttgcctca tgctttcgcc agacccctgt   25560
ggccccttcc cgaccctgga gtgccctgg ggcttcctgg aaaggcctc tcctttgctc     25620 acagttgggt gccgaacttc accagcattg accacccgaa ggcgcaggga cacccccgca   25680
gtccctctcc tgggggtccc atcaccaact cccatgggc gggatatcag aagaattc      25738
```

<210> SEQ ID NO 37
<211> LENGTH: 40558
<212> TYPE: DNA
<213> ORGANISM: Homo sapiens AF087017

<400> SEQUENCE: 37

```
gatcaggtca gactgcagta gggcaggccc tgaatcaaac atcatggtgt cctcacaggt      60
agaggagagg cacgagagag caacgctgcg tgaaggcgca ggatgagagc atcctggaag    120
atgggcacgg ctggggtgac aggtctggga gcctgggaac actgggaaag tcggccagca    180
ctggagcctc ccttagagct cgaagaagga gccagccctg accacccga ctctgacctt     240 ctagcatcga aacagggaga gacgcattcc acgtggttgt tccaatcagc ccagtttctg    300
gggcttcctt atggcagcct cagggaactg gcaaagccca gtgggctat cccattactt     360 atatctgggt aggtcccagc cacaggggag agaaaagaga aagcccctct atctaatgac    420
```

| | |
|---|---|
| acgctgtact catgtcccac ccgcatgatg tgccgtaccc gtgtccctat ccaggtgacg | 480 |
| tgccgtaccc gtgtcccacc cgggtgacgt gccgtacccg tgtcccaccc gggtgacgtg | 540 |
| ccgtacccgt gtcccacccg ggtgacgtgc cgtacccgtg tcccacccgg gtgacgtgcc | 600 |
| gtacccgtgt cccacccggg tgacgtgccg tacccgtgtc cctatccagg tgacgtgccg | 660 |
| tacccgtgtc ccacccaggt gatgtgctat gcccatgtcc cacccaggtg acacgctata | 720 |
| cctgtgtccc tatccaggtg acacgctgtg ccatgtccct atccgggtga cactgtgcca | 780 |
| tatccctatc caggtgacac acagtgctca tgtgtctatc tagatgacag caccgtgccc | 840 |
| acatctttat cccggtgaca gcactgtgcc acgtcctgt cttggtgaca tcactgtggt | 900 |
| tatatacctg tccatgtgac atcactgtgc ccacatctgc ctccaggtga cagcgctgtg | 960 |
| cccacatccc cacccaagtg ctctgggcac cttggctggg gctctggcca ctttcatgtt | 1020 |
| ggtgccaccc tgtgtgtgga tcatagcacc caggcactca ccattaccgt ggccagcaca | 1080 |
| gaccagaccc gaccccagta gtcctcaaaa ctaggtcccc tgctgggtgc ggtggctcac | 1140 |
| gcctgtaatc ccagcacttt gggaggctga ggcgggcgga tcacaagatg aggagatcga | 1200 |
| gaccaacctg gctaacacgg tgaaacccca tctctactaa aaatacaaaa aattagccgg | 1260 |
| gtgaggtggt gggcgcctgt agtcccacct acttgggagg ctgaggcagg agaatggtgt | 1320 |
| gaacccggga gcggagcct gcagtgagcc gagatcatgc cactgcactc cagcctaggg | 1380 |
| gacagagcga gactcaaaaa acaaaaaaac aaacaaaaaa aaactaggtc ccctgtgctg | 1440 |
| tgctgctgta ccccagcagt cgcttcactg gcaagactac tcttagcagg tgcgcctgga | 1500 |
| agcagaaact cggcagctcc cggtctgtcc tatacacatg caaatgcccc attagaaagc | 1560 |
| aaatagcccg aggtgtttgc ctgctcccag gcaaaatctc ccaaatcttc ctccgggaat | 1620 |
| cagtgaacag aagagatgtc catcaccccc aggagagtag tgtctgaacc cgtctaaccg | 1680 |
| cccaacaggt tctccctgcc gccggtctgg acagagctgc tttatcacaa caggtgactt | 1740 |
| gcaataaagt ttaattcaca cagagtcggc cgtgcaggag accagagttt tattattact | 1800 |
| caaatcagtc tcccaggaaa tttggggatc aaagttttta aggatcattt ggtgggtagg | 1860 |
| gggcgagtca ataggagtg ctgattggtt gggtcagaga tgaaatcatg gagagtcaaa | 1920 |
| gccatctttt tctgctgagt cagttcctgg gtggggccaa caagactaga tgagccagtt | 1980 |
| tatcaatctg gggggtgcca gctgatccac ccagtacagg gtctgcgaaa tatctcaacc | 2040 |
| actgatctta ggttctgcaa cagtgatgta atcctaggag caatttgagg aggttaaaaa | 2100 |
| tctttcagcc tccagatgtg tgactccatg actcctaaac cataatttct aatctgtggc | 2160 |
| taatttgtta gtcctgaaag tctagtcccc aggcaggaag agggtctgtc ctgggaaagg | 2220 |
| gctgttattg tctttgtttc aaagataaac tataaactaa gttcttccca agttagtcc | 2280 |
| agcctgcacc cagaaatgaa taagaaggca agacagagtt ggttacgtca gatctctttc | 2340 |
| attgtcataa ttttctgtta tatatttttt ttttttgag acagagtttc gctcttatca | 2400 |
| tccaggctgg agtccaatgg ctcgatcttg gctcactgca acctccacct ccggagttcc | 2460 |
| agtgattctc ctgcctcagc ctcccaagta gctgggatta caggcgccca ccaccatgcc | 2520 |
| cagctaattt ttgtattttt agtagagatg ggatttcgtc aggttggcca ggttggtctt | 2580 |
| gaactcctga cctcaggtga tccacccacc tcggcctccc aaactgctgg gattacaggc | 2640 |
| atgagccacc atcgccggcc gattttctgt aataattttt gcagaggcgg tttcaccagg | 2700 |
| agaaccaagc attaatgcgc tgtggctgat gtgtagtaga gcggcatttc ccaatgggag | 2760 |
| aaccctgggg ctgtctagga gcccatgcat ggctgggagc ctaatcccag ggacaccacc | 2820 |

-continued

```
gatgacagct cccatagcac gtaggacagt ggatacttgg aggcaaagag aaatctctgt    2880
tctgcagtgg tcatgacttg gaccccaaag aacttgagcc caaggtccag agggagaccc    2940
tcccaacaag gcctccagca ggaacaggga tcgtgggagc ctgccaagca cagcgcacag    3000
gtatttctgg aggcttccca ttcagtcttg gatgccagcc tcaccaaggg cggcccatct    3060
tgctgacctc accaagggag gcccgtctca ctgccctgat ggcgcagaat cggctgtacg    3120
tgtggaatca gaagtggccg cgcggcggca gtgcaggctc acacatcaca gcccgagcac    3180
gcctggctgg ggttcaccca cagaaacgtc ccaggtctcc caggccaggt gccgcattgg    3240
ttcccgaggg ttgtcagaga tagacactca tgcgactaac atcgggctat gtgtttgatt    3300
caccccaggg tgcattgttg aaggttgggg agattggagg agatgcttgg gggacaatga    3360
ggtgtcccag ttccttggat gatagggatc tcggcctaag cgtgagaccc ctcctacagg    3420
gtctctggca ggcacagagc ctgggggctc ttgcatagca catgtgtatt tctggaggct    3480
tccccttcgg tctcaccgcc ccgatggtgc agaatcggtt gtagttgtgg aatcggaagt    3540
ggccgcgcgg cggcagtgca ggctcccaca tcacagctca gcccgcccc agctgaggtt    3600 cacccgcgga aacgtcccgg gtcacgcaag ctaggtgccg caaggttcac gggggtagtg    3660
agggatagaa cactcatggg agccacattg gctacgtgt ctgattcacc ccagggtgca    3720
ctattgaggg ttggggagat gagatacttt ggtgacaatg aggtgtcccc attctttgga    3780
tgatggggat ctcggcctca gcgtgaggcc cctcccacag gtctctggc aggcacagaa    3840 actgggggct cttgcgtagc acatgggtat ttgtggacgc ttccccttct gtctcaccac    3900
ccggatggca cagaatcggt tgtaagtgtg gactcaaaag tggccgcgcg gcggcagtgc    3960
aggctcacac atcacagccc aagccctccc tggatggggt tcgcccgcgg aaacgtcctg    4020
ggtcacccaa gccaggtgcc gcagggttct cggaggtctt ctgggaatag gacgctcatg    4080
ggagccacac cacgtcttcg tatcgggcca tatccacggc cgcgtggccc caggtcacac    4140
tctgagggct tcagtgtcat ggcctgggac tcaagtcacg cctacccgcg tgatgagcac    4200
agcaaattcc aacaaaagct tatactttcc acatccatcc cagagcacag atccgactaa    4260
ggacagcccc caaatcccga gccttttct gaactgacaa ttgcctcccc agtgaacact    4320
ctgagcttgt caatcttaag tggccagaca ttaacattcc cattcagtgc aggtttgaga    4380
tgctaattta ggagcttgag atgctaaaga gctgggagtg ccactgctgc tttattctgg    4440
ggtctaggat ccttgtgttg gctgagataa tctgctaatg tgggtgcagc agacatcccg    4500 cggtttgtg aatcgataaa ggatgggat caatggtgtt tgtgcactgt gcggtctgtg    4560
cccaattgcc tgccttgtgc tgtggaatct gtacacctgg ccaacatgtg cttgtgtgag    4620
cctgacagtg cattttccag agcctcacct cggctctgcc ctgaggctc tgtgctgctg    4680 gaatcagact caaggacctc atcagaggac catggccccg tatcacctgg gtcaggcact    4740
gaagctggga caggagagca gagacttcca aaatgaggga tccctgtgtt ctgaggtgat    4800
catgactggg acccaaggac tcaagcgcat gctccagagg gaatcgtttc ccacaaggcc    4860
tttggcagga acagggatcc tgggagcctg ccaagcagag cgcacagtgt tcctggagtc    4920
tcgctgccca gatgccacgg aatcagttga aggtatggaa acacaggtgg ccacgtggta    4980
gcagggcagc tcaggcgtc atagcccgag cccggctacc tgtggtttgc ctgcagaaac    5040
atcccgggtc aacaggccag gcaccgcatt ggttcgcgag ggtcatcggg ggtaggaccc    5100
ttgtacgagc cacatcgggc tacgtgcctg attcacccca gggtgcactg ttgaaggttg    5160
gggagatgag aggagatact tgggggacag tgaagtgtcc ccattctttg gatgatgggg    5220
```

```
atctcggcct cagcgtgaga cccctcccac agggtctctg gcaggctcaa gagcccaggg    5280
gctcttgcat agcacatgaa tatttctgga ggcttcccct tcagtctcac cacccggatg    5340
gtgcagaatt ggttgtagct gtggaatcgg aagtggccgc gtggcggcag tgcaggctca    5400
cacatcacag cccgagccca ccccagctgg ggttcgcccg cggaaacgtc ccgggtcccg    5460
caagccaggc gccgcagggt tcacgggggt catcagggat aggacattca tgggagccac    5520
atcgggctat gtgtctgatt caccccaggg tgcactattg agggttggga agatgagagg    5580
agatgcttgg gggacaatga agtgtcccca ttctttggat gatgggatc ttggcctcag     5640
ggtgagatcc ttcttgcagg gtctatggca ggcacagagc ccgggggctc ttgcatagca    5700
catgtgtatt tctggaggct tccccttcag tctcaccgcc cggatggcac ggaattggtt    5760
gtagttgtgg aatcggaggt ggctgcgcgg cggcagtgca ggctcacaca tcacagcccg    5820
agcccgcccc agctggggtt cgcccgtgga acatcccag gtcatccaag ccgggcgcca     5880
cagggttcac aggggtcgtg aggtatagga cactcatggg agccatatcg gctacgtgt    5940
ctgattcacc ccagggtgca ctgttgaagg ttggggagat gggaggagat actagggaa    6000
caatgaggtg tcccagttcc atggatgatg gggatctcgg ccctagtgtg aaacccttct    6060
cgcagggtct ctggcaggca cagagcccgg gggctcttgc atagcacatg ggtatttctg    6120
gaggcttctc cttcggtctc accgcctgga tggcacggaa ttggttgtag ttgtggaatc    6180
ggaagtggcc gcgcggcggc agtgcaggct cacacatcac agcccgagcc cgccccaact    6240
ggggttcgcc cgtggaaacg tcccgggtca cccaagccac gcgtcgcagg gttcacgggg    6300
gtcatctggg aataggacac tcataggagc cgcaccagat cttcaggtcg gcattatcc    6360
acagccccgt ggccccgggt cacactccga gggcttcagt gtcatggcct gggactcaag    6420
tcacgcctac ttatgtgatg atcacagtgt gttccaccaa aatcttacat tttccacatc    6480
tatcccagag cacagctccg actccgtcta aggacagccc ccaaatcccc agccttttac    6540
tgaactgaca attgcctccc cagtgaacac tctgatctcc tcagccctaa gtggccagac    6600
attaacattc tcattcaatg caggtttgag gtgctaattc aggagcttaa gatgctaaag    6660
agctgggagc gccactgctg ctttattctc tggtccagga tccttgtgtt gctggagata    6720
atccattatc gtgggtgcag cagacaccct gcggcttgtg gactcggtac ggggtgggga    6780
tcctgatggg gttaggatgt tcgatggctc gggtgtgctc cacgctcagg gatcatcacg    6840
tccggccggc ggtagttggc acgtggagag gtgaatttgc ccacaggtgt tccccgtgcc    6900
tgcgcattgc tggcagcacg accggatcct gtgctagccc ctcccacaat gcctggagca    6960
ggagcgaggg gcctggggag ccgccttgcc tggagcattt gtatttccgg agtatttcct    7020
gagtctcccc ttgggtcttg ggtgctgtcc ccagtgagcc catctcccag cgatggcaca    7080
gaatcggttg tggctgtgga gacggaaatg gccgagaggc ggcagtggtg actcacatca    7140
cagtctgaag gtgacccaag gctggactcc acttttagca aaatgtgggg gtctgccttg    7200
gtctcctaac ttgggggtcc actcatggaa aagcctgaga attttcatgc catggaaatt    7260
cccccatgtc gtgggttca cgcacgacaa agcccggcgg tcagtgctca gcaggcaagc     7320
actcagccct ttccggtggg gccatgggaa cagagggttt gccgaaggcg cggccagccc    7380
ttccacatcc cagagggcct gctgcgtgat tggacccgtg aactctgggt cccttggccc    7440
tggtgctccc cttcacggct ttgacactcg agacttgagg tgaaccccag ggactgcagg    7500
gccccaacaa ccctcaccaa aggccaaggt ggtgaccgac ggaccacag cggggtggct     7560
gggggagtcg aaactcgcca gtctccactc cactcccaac cgtggtgccc cacgcgggcc    7620
```

```
tgggagagtc tgtgaggccg cccaccgctt gtcagtagag tgcgcccgcg agccgtaagc    7680
acagcccggc aacatgcggt cttcagacag gaaagtggcc gcgaatggga ccggggtgcc    7740
cagcggctgt ggggactctg tcctgcggaa accgcggtga cgagcacaag ctcggtcaac    7800
tggatgggaa tcggcctggg gggctggcac cgcgcccacc aggggg tttg cggcacttcc    7860 ctctgcccct cagcacccca ccctactct ccaggaacgt gagttctgag ccgtgatggt    7920
ggcaggaagg ggccctctgt gccatccgag tccccaggga cccgcagctg gccccagcc    7980 atgtgcaaag tatgtgcagg gcgctggcag gcagggagca gcaggcatgg tgtccctga    8040 ggggagacag tggtctggga gggagaagtc ctggaccctg agggaggtga tggggcaatg    8100
ctcagccctg tctccggatg ccaaaggagg ggtgcgggga ggccgtcttt ggagaattcc    8160
aggatgggtg ctgggtgaga gagacgtgtg ctggaactgt ccaggggcgga ggtgggccct    8220 gcggggcccc tcgggagggc cctgctctga ttggccggca gggcagggggc gggaattctg    8280 ggcggggcca ccccagttag aaaaagcccg ggctaggacc gaggagcagg gtgagggagg    8340
gggtgggatg ggtgggggt aacgggggaa actggggaag tggggaaccg aggggcaacc    8400
aggggaagat ggggtgctgg aggagagctt gtgggagcca aggagcacct tggacatctg    8460
gagtctggca ggagtgatga cgggtggagg ggctagctcg aggcagggct ggtggggcct    8520
gaggccagtg aggagtgtgg agtaggcgcc caggcatcgt gcagacaggg cgacatcagc    8580
tggggacgat gggcctgagc tagggctgga aagaagggg agccaggcat tcatcccggt    8640
cacttttggt tacaggacgt ggcagctggt tggacgaggg gagctggtgg gcagggtttg    8700
atcccagggc ctgggcaacg gaggtgtagc tggcagcagc gggcaggtga ggaccccatc    8760
tgccgggcag gtgagtccct tccctcccca ggcctcgctt ccccagcctt ctgaaagaag    8820
gaggtttagg ggatcgaggg ctggcgggga gaagcagaca ccctcccagc agaggggcag    8880 gatggggca ggagagttag caaaggtgac atcttctcgg ggggagccga gactgcgcaa    8940
ggctgggggg ttatgggccc gttccaggca gaaagagcaa gagggcaggg agggagcaca    9000
ggggtggcca gcgtagggtc cagcacgtgg ggtggtaccc caggcctggg tcagacaggg    9060
acatggcagg ggacacagga cagaggggtc cccagctgcc acctcaccca ccgcaattca    9120
tttagtagca ggcacagggg cagctccggc acggctttct caggcctatg ccggagcctc    9180
gagggctgga gagcggaaag acaggcagtg ctcggggagt tgcagcagga cgtcaccagg    9240
agggcgaacg gccacgggag gggggccccg ggacattgcg cacaaggagg ctgcaggggc    9300
tcggcctgcg ggcgccggtc ccacgaggca ctgcggccca gggtctggtg cggagagggc    9360
ccacagtgga cttggtgacg ctgtatgccc tcaccgctca gcccctgggg ctggcttggc    9420
agacagtaca gcatccaggg gagtcaaggg catgggcga ccagactg ggcgaggcgg    9480 gcggggcgga gtgaatgagc tctcaggagg gaggatggtg caggcagggg tgaggagcgc    9540
agcgggcggc gagcgggagg cactggcctc cagagcccgt ggccaaggcg ggcctcgcgg    9600
gcggcgacgg agccgggatc ggtgcctcag cgttcgggct ggagacgagg gtgagttttt    9660 cccctctgc caccctcagc ccccaccgc ccctccccac acaaccaaca cgttctcccc    9720
acacgactct ctcgttctcc ccacagccag gtctccagct ggggtggacg tgcccaccag    9780
ctgccgaagg ccaagacgcc aggtccggtg gacgtgacaa gcaggacatg acatggtccg    9840
gtgtgacggc gaggacagag gaggcgcgtc cggccttcct ggtgagcgtg tctgccctcc    9900
ctgcgtcagg acgcggccct gcccagaccg cccgccggg ccaccatctc actgcccga    9960 cctctgtctt ctacagaaca ccttaggctg gtggggctgc ggcaagaagc gggtctgttt   10020
```

```
ctttacttcc tccacggagt cggcacacta tggctgccct ctgggctccc agaacccaca    10080
acatgaaagg tgaggggctt cctgccacac ttggggtggg gggcacgcga gaggagctga    10140
gtgggacctc actccttccc catccacaga aatggtgcta cccagctcaa gcctgggcct    10200
ttgaatccgg acacaaaacc ctctagcttg gaaatgaata tgctgcactt tacaaccact    10260
gcactacctg actcaggaat cggctctgga aggtgagcac cagcgctcct tccggaagcc    10320
tccaggcccc cgagcaccct gcccccatcc cacccacgtg tcgctatctc taggtgaagc    10380
tagaggaacc agacctcatc agcccaacat caaagacacc atcggaacag cagcgcccgc    10440
agcacccacc ccgcaccggc gactccatct tcatggccac ccctgcggt ggacggttga     10500 ccaccagcca ccacatcatc ccagagctga gctcctccag cgggatgacg ccgtccccac    10560
cacctccctc ttcttctttt tcatcctcct gtctctttgt ttctgagctt tcctgtctt     10620 ccttttttct gagagattca aagcctccac gactctgttt ccccgtccc ttctgaattt     10680 aatttgcact aagtcatttg cactggttgg agttgtggag acggccttga gtctcagtac    10740
gagtgtgcgt gagtgtgagc caccttggca agtgcctgtg cagggcccgg ccgccctcca    10800
tctgggccgg gtgactgggc gccggctgtg tgcccgaggc ctcaccctgc cctcgcctag    10860
tctggaagct ccgaccgaca tcacggagca gccttcaagc attccattac gccccatctc    10920
gctctgtgcc cctccccacc agggcttcag caggagccct ggactcatca tcaataaaca    10980
ctgttacagc aatttgtctc gaggactctg gaatccgggc tgtgggcatg atgtggggga    11040
ggccagcctt gggcagaggg gggctggggg gcatggggag gagtacatga aaaggggat     11100 gggggttcca gggtggggga ttctgggatg ggtgcagcgc agcacacacc aggggtgggg    11160
tgagcacagg gtgtgtggac ctcaggggtg cagggcaggc ggtcagcatg cagtgatggc    11220
agtggagggg ctgtgggacc aggggcttca cagactgggc ggggctggg cttgcggagg     11280 gggcctgcgc tctgaggcag gggtcgggga ccaccaaacc atcccgagc gagtgcctcc     11340 tgtcgcccca aagtcccatc agaatgacgc cttggtgctg ccccagacc cctgaagccc     11400 gggctaggtg actggggtag agctggccat ggccgctctg ggaggcccac aaggtgctct    11460
gggcgacccc accccgacag gggcacgaac cccgcgccag tcccgttcct gctccccttt    11520
tgctgtgggt gggagccggg gccacgccgg agggacggcc ccacacaagg agccagggg     11580 ttgtggggga gccggtgggc ttctcagtgg gcaggtggcc ttggggcaga ggtcctaagg    11640
aggccagggg accaggagga gggaggaaga agttgagggt tgccacaggg aggaggtgag    11700
gaggagcggg agggcccagg gtgagggct ccccgggctcc ctccccgggg tcttgctgct    11760
ggagctccaa gaaccccggt atgcaggggt tcgctcccca ggtgccaagg cagcccactc    11820
atgggttccg ggtcagcttc cccgcagagg ccagtggccg gcagctccct cagccaggcc    11880
tcccagctcc cggcccctcg ctgtgcaggc gctgggaaca caaggggcag ccctggaaa     11940 taagggtggg gtcccggcct ccccattcct tccccctcc ccctgcctt caccccat       12000 tcccagtgca cagagctgtc aggaaaattc ctccccgact gacaaagaac agacaggaag    12060
gcggttaggg acgcccctcc cctaccggcc cagccgccct tggggtcttg gtgtccaggg    12120
cggaagagca gggtggttcc ccacgtccct tgggtctggc ctccctctg caccctctct     12180 tgcccctcc ccatccagct gtgggccctg ggactgtca gagaccgagg ggtttccagg      12240
gacacacttg tgtgctaaaa cctgggcggg tggtcacccc ccaggatgca tgtagacatc    12300
cggtgaggga gtctcttgaa gtctctggga tggtgccct gggactggct gccatctcat     12360
ggaggaggtc agaggtcgct ggggccagcc cagggtgagg ccgcattcat cttcctgacc    12420
```

```
ctacaggcca atttgactta cccaagtggg ttttggccgg caggatgaag taacccatcc    12480
attacatgtc aagagttagg tctataaacg gcctttatta taaacatcca actctgcagg    12540
aggtttacaa agcagggctc aggagataaa agccggcttc cccaggtggc ggctgcaggg    12600
tgcggcaggc agcccagggg gtgcccaggg tggcggggca gggaaccgt agggagggg     12660 agaggggcac ccagaaaacc tctcctggag aacatggaag actctgccca cttcaaatcc    12720
ctgcctgggg aaggacacat gggaatgggg ccggggaaa aggcgggcca cctcgggcct    12780
tcgtcacctg tgtcagctcc tagggattgt ctcctcctgg tcacttggag agaacaggcg    12840
tgctggacac gtccacatct ctgggcccgg ggtgtatgaa tgacacgctt gctctggagt    12900
ttccacctgg gagctgtatg gggacagggc tgttcctcct cacacccgct ggggaaggga    12960
cacaggcctt tggtggccc ccaccatctc ccagcactgc ccatggctgt gcccacgctg     13020
gctgccccct gagagcagga cgtgtactca ggggcagcgc ctacctctgg gcagcccagg    13080
tttctctgct ccctgcagcg gaacgggctt cctaggcag ttcctggggt ggtgtccta     13140 gggcagcccc tgagtgctgg aggggctctg ggccacaggc cctgaaacag ggaggtggtg    13200
ggggcagcgt tcagggggct gaaccctcagg gtgaggcggg caggcgggga gccacaggcc    13260
cgggggcccc gcagcaggtg ctcagcctcg gagcctcctg ccgcacccccg ggcggggc     13320 tgggagcccg cccgagcccc tagctctgag cgacctgcca ggttggaatg tgtgtttatc    13380
tttggcccaa cccgatttcc tgctttttag aaaagggggct tagagagggt tgttagacag    13440
gctccaggca ccccaacacc caaaggcact ttgaaaacgc ccctgcactg acttcagtgc    13500
ggagaagcaa acgggctgga atttcactcc caaacccccaa catggggggtg gcggggccgg    13560 ggtgagggtt gtggctgcct gcaaaggtgc caggaaatct ggggagggag gaacttccac    13620
cgttcaggga gaccctgagg gtgccctggc ttctggccac gtcccagacc ctgttaggca    13680
ccgaggtctt cacacccaga ccctccaccc acccaagttt ctgcggcacg tttaggttga    13740
gtgaagacca agtcatccag ttagagaaga ggacttgagg cgcgtgctgc tgctgtggcc    13800
acgctggacc ttcggtgcac gcatctcctg gcgagtcccc tgtggctctg tgggccgtac    13860
acacccgggg cacgcgacct cagctacctt gtcaccgagg acgtgcatcc acagctgtgc    13920
gtctgtgcct gggagcgggg tctccacttg gtgggtctct gcatgctgac cagttaaccc    13980
gccttttcgg gctgtggagg gcgtgggtcc tgtccggccc ggagatgctc cgcggggtgt    14040
gtgtgtgatc gtggccctgt agcggggtgg tgttccctgg agggtggacc cctgagcctg    14100
gctgtgtgtg gctcgtgtct cagcatgaat tccgtgaccc aggagcacgt tttcaggcag    14160
ggattagggg cagctgggtg tgggaggcag gcacttggta taccaccgaa tggagacaga    14220
aaatcccaac tctacgaagg aagtgaagtc ccttcaacag ggacaaagcg atgttttggg    14280
tctgactaca atgcaccctg ggaagtctca aagaaaacag tcggggactc aaggagggca    14340 gcccctctc cccgacccccg agctcccagg aagataaatg atttcctcct ctctagagat     14400
gggggtggga tctgagcact cagagccaag ggcgcagtgg gtccgggcgg gggcctcctc    14460
ggccctccca acatggggc caggaggtca gcccctcaac ctggacccccg gctgggtctc    14520 agggaatggt ctcccccagt ggcccagctt gcttgtgttt tcagatgggt gtgcatgggt    14580
gtgtgtgtgt gtgtgtgtgt gtgtgtgtgt gtgtgtgtgt gtgatgcctg acaagcccca    14640
gagagccaaa gacctgagtg gagatcttgt gacttctcaa aagggggatt ggaaggttcg    14700
agaagagctg tggtcagcct tgctctccct taaggctgtg gtaaccacac taggcatagc    14760
ataggcctgc gccccgtccc tccttccctc ctccgcgcct ctcctttctc tttctccccc    14820
```

```
ctctaccccg ctccctggcc tgctcctggt gacaccgttg gcccccttcc agggctgagg    14880
gaagccagcg ggggccccct cctggaagcc cacctgcagg ccggcttgct gggaaggggc    14940
tgctctcgca gaggctcccg cccgccctgc agccgtttcc tggaagcagt cgctgtgggt    15000
attctgttcc ttgtcagcac tgtgcttgca aagaaagcag acactgtgct ccttgtcctt    15060
agggagcccc gctccatcac ccaacacctg gctggacaca ggcgggaggc cgggtccgcg    15120
gggagcggcg cggggctggg gccggaccag taaacacaca cggcgccag gcactgcagg    15180 ctcctcctcc tcctcctgcc cagcgcctct gctcacaggc acgtgccaag cccctaggcc    15240
aggaggccca gcagtgggtg cagagcaagc tcctgggaag ggggtgcagg gcggaccccc    15300
ggggagaagg gctggcaggg ctgtgggga cgctgaccgt gggccccacg ttgcagaaaa    15360
ctggctgcct ggctggaaga tggggagat gccaagcctc tgaggcagca cgagcagggt    15420
gcatggaggc cggggcgcgg ggaggctgca ctgcagcatg caccccaaag cccagaggga    15480
gtggagacca ggccctggaa tcgagaagca gaaaggcggc ttggaggcct cggaaccggc    15540
tgacctccaa cagagtgggg ccggccctgg aggcaaagag gtgcccgggg tccggccctg    15600
cctgggggag ctatgtgtca tgggcagcca caggatatgt agccagctct gagcatatgg    15660
acccagggca gggctgcaag gcagggcagg ggagacagac gggggagcaa ggagcagaga    15720 ggggggcctca ggctctccca ggaggaacat tctcccgaca ggaggaagag acggcccagg    15780
ggtgactgtg gggagccatg gtggcagctg gggtcgtggc agatgggaga gaggctggcg    15840
aggtgaaggt gcaggggtca gggctctggg gcccacatgc ctgtgggagc aggcaggccc    15900
agggctctcc gccactcccc actcccgctt ggctcatagg ctgggcccaa gggtgggtg    15960 ggatgagcag gagatggggc ccagggggca agcagggccc caaagacatt tagaaaaacc    16020
ggtttatgca ggcagcattc agagcaggcg gcgtgcgtgg cggggggccct gggagcacag    16080 agaggcacac gtagggcccc cgaggggctc cccattggcc ggcagtgaca tcacccctgt    16140
gtgtcaacag tgatgtctgc agctccggcc agccagggtt tatggagcga gacccagccc    16200
ggcctgggcc ctcactcccc aggcccacac actagcccac tgttcagggt ccggggtggc    16260
ggcatggcct gggggtcctg gcaccgctgc tcctctgccc accctaactt cccggcatgg    16320
cggctgcccc ctctgagcgt ccccaaccag taagtgtggg gccagcaggc ctgccgtcct    16380
cctcctcttc cctctagaga gaaacgtgga ggtcctgggg ctggggcgc tcatagccct    16440 gtgacacagg tgcatggggt caggggtccc agaatggccc ctgggaagga cctcagctgg    16500
gccggcggct ctaggcttca ggggtctgtc tgcacagggg ctagccctc ccagacctct    16560 gtgaagccag tacgggcctc ccctccctgc cccgtgctct gtccggtgct tcctggactg    16620
cactgcgggc cactggtgag agggtggaca gggaagggcc gccgtggtgc ctgttcctgc    16680
ccacctggct gtgtggtccc ctccaagtag ggacaaccct tctgagggct tgggggcacc    16740
ctggggttgc cagggcctcc cagagccctg tgagcccctg gggggtctgg cctgatgccc    16800
ccctccacgt ccagggccgg ctgtggccca gaacccagc ttcccagcag gccggtgtgc    16860
ggtggtgacc cagaggaggc ctcgcctcca ctgaggggcc accgacctct gccaggccac    16920
agagaccccc aaaggagtct gaaaggctgg agacccgggg ctgggaccag gtgggacttt    16980 cccacgagc cgtccccagg cccagctggg gacacgtccc ccttctctcc agacacaccc    17040
tgcctgccac cacgacacac cggcctgttg ggggtctctt ttaagtgctt gccactctga    17100
ggtgactgtc cctttccaaa gaggtttctg gggcccaggt gggatgcgtc ggcctgagca    17160
ggaggatctg ggccgccagg ggctggggac tgtctcctgg ggaaggaagc gcctgggagc    17220
```

```
gtgtgtgctg acccaggacc atccaggag gcccgtctgt ggggcaagcg ggaagggagc   17280
ggctggagag gcttggccgc ccccgccctg cctcccattc cttagctcca tgcctgtcaa   17340
cctctgtcac ccagtgagtg atgtccaggg gccctggaaa ggtcacagca tgtttgagcg   17400
gggtgagaga gaggggaaag gcgggggcgg ggaaaagtac gtggaggaag ctctaggccc   17460
aaggaaggag aaagggttct gggagggagg gagccactgg ggccgccggg aaggtccctg   17520
cctgctgctg ccacccagaa ccctcgcctc ttagctagcc cccgcagccc cagcctttct   17580
ggcctgtgcc cctctccccc atcccagct gtcctgtgca accaggcctt ggacccaaac   17640
cctcctgccc cctcctctcc ctcctcaccc tcccaatgca gtggtctcca gcctggctct   17700
gccctgccgc agtcccctcc cctcattcca ggcctagagc ctccagtccc ggtggccccc   17760
agcccgaggg tgaacggcct caccctgggt cgtgggacag agggcacgtt catcaagagt   17820
ggctcccaag ggacacgtgg ctgtttgcag ttcacaggaa gcattcgaga taaggagctt   17880
gttttcccag tgggcacgga gccagcaggg gggctgtggg gcagcccagg gtcaaggcca   17940
ggctgtgggg ctgcagctgc cttgggcccc actcccaggc ctttgcggga ggtgggaggc   18000
gggaggcggc agctgcacag tggccccagg cgaggctctc agcccagtc gctctccggg   18060 tgggcagccc aagagggtct ggctgagcct cccacatctg ggactccatc acccaacaac   18120
ttaattaagg ctgaatttca cgtgtcctgt gacttgggta gacaaagccc ctgtccaaag   18180
gggcagccag cctaaggcag tggggacggc gtgggtggcg ggcgacgggg gagatggaca   18240
acaggaccga gggtgtgcgg gcgatggggg agatggacaa caggaccgag ggtgtgcggg   18300
cgatggggga gatggacaac aggaccgagg gtgtgcggga cacgcatgtc actcatgcac   18360
gccaatgggg ggcgtgggag gctggggagc agacagactg ggctgggctg ggcgggaagg   18420
acgggcagat gggatcccaa ggacatggaa tttcggacct tctgtcccca ccctctctgc   18480
tgagcctagg aacctctgag cagcaggaag gccttgggtc tagagcctag aaatggaccc   18540
ccacgtccac ctgcccagcc tagacccca gcattgaagg gtggtcagac ttcctgtgag   18600
aggaagccac taagcgggat ggacaccatc gcccactcca cccggccctg ccagccctg   18660 cccagtccag cccagtccag cccagccctg cccttcccag ccctgcccag cccagctcat   18720
ccctgcccta cccagcccag ccctgtcctg ccctgcccag cccagcccag cccagccctg   18780
ccctgccctg ccctgccctt ccagcccctg accttcccag ccctgcccag cccagctcat   18840
ccctgcccta cccagctcag ccctgccctg ccctgccctg ccctgcccag ccctacccag   18900
cccagccctg ccctgccctg cccagctcag ccctgcccac cccagcccag cccagcccag   18960
catgccttct ctggctggag agcacaggct tgaccttaga aagaggctgg caacgtaggg   19020
ctgaggccac caggccactg ggtgctcacg ggtcagacaa gcccagagcc tgctcccctg   19080
ccacgggtcg gggctgtcac cgccagcatg ctgtggatgt gcatggcctc agggctgctg   19140
gctccaggct gcccccgccc tggctcccga ggccaccct cttatgccat gaaccctgtg   19200
ccacacccac ctctgagctg tccccgctcc tgccgcctgc accccctgag cagcccctg   19260 tgtgtttcat gggagtctta gcaaggaagg ggagctcttc aatcttgcca gtcagggtgc   19320
tgtctgctga gtaagtgtcc ccgtgctgtg ccccaatgtc cccatccttt ggcaaacagc   19380
catcagcctg tggatcctgc actcccatgc ggtgggagag ggagacctgg gctcacctga   19440
gcctccccac aagccaggga gaggggctgc ccaatggcgg gaggccccca tggatcccaa   19500
acggcagttg cccgcactcc tacccaggaa ctttgtctgt gatgaacagt aaggaataag   19560
gaagcgggtg agaaagaagg aaggaaaggc ggtggggggc atggcggggg gcggggaggg   19620
```

```
tgtttggaaa gttccagaaa agagtcactt caccagaaag gccacaagct ccccgtgccc    19680
ccagcccctg ctcggctccg aggtgaagga cttggagcgt cgacgctggc gtggggacca    19740
gctgttctcc ttgagtttgt ttccttcagt tccttccggg cctcaccctc ctcttcctgc    19800
cacacacaca cttttttcct ttttaaattg ttttatttgg ggccaggtgt ggtggctcac    19860
acctgtaatc tcagtatttt agaaggccaa ggtgggcaga ttgcttgagt ccaggagttg    19920
gagaccagcc tgggcaacat agtgagaccc catctctacc aaatatcagc caggtgcggc    19980
ggcgcgcacc tgtattccca gctatgtggg agactgaggt gagaggatca cgtgagccca    20040
ggaggttgag gctgcagcaa gccatgatca taccactgca ctccagcctg gcaagagag    20100 tgacaccctg tctcaaaaaa aaaaaaaagt agaaaatttt attttaaaaa attgttttaa    20160
catttgagtg ctacaactgt ccaaggagga gcagacggcc cgtgtcagac agcctgaagc    20220
ctgactgtct gcgatcaacg gccccgtgcc agctgtgtgc agcagtttgg cctggcctga    20280
tgcctctgtc cttggcacca gctcacagcc cgtgcccata acagacctgg ggcaccgaag    20340
gaagggcaga tccagccccc acctgccctg ggtctgaaga tctcccagga ggctccatgg    20400
ggtgccttga gtgggagggg ctggccgata gccttgagga attggcacgg acatgcagag    20460
aggggcatgt cccaaactcg gggcgctgtg gcctccagct gccaggaggt agatgtgttc    20520
tgacttctgg gttcccacca ccagaactgc aggggatatg aagcaagctg gacttgggga    20580
gacatctctg ctcgagtgca cgttggcctg atgacgactg ctcttgggtt cacgggttcc    20640
aggctctgcc cgggagcctc atgcaaactg gtcccgttct acagacgagg aaactgaggc    20700
acagagtgat tacggctgtc cctgagctcc tgcagccagt aaggtgatac accaggatgt    20760
gttcccaggt tgtccgctgg gctcagtaac acagtctcaa ctgccctgtg acactgcgtg    20820
tctgtgcttg tggggaaggt gaccagaggc cccctttcct ccacgcggtg agcctaccag    20880
caaggagaca gtcctcaggt gtgaggatga gcctcgtagt aggcacagag aaacaggagg    20940
aaccttctgg aaggtgaagc ctcccacggc tgggactctt ggagaagggc ggatctctgt    21000
ccactcctgc ccaatcccca gcacagacag agcaagcagg acagagggcc caacgtccca    21060
ggatactgca gagctcaaag gagggcagag agcatcgccc cacatgggcg ccgggagaaa    21120
ggtgggcggg gtgctcaggg gcccctggcc gtcctgaagt ttgcctcaga gaggtgtggg    21180
cttctcctcc ctcccataca cagtgtctct gaggatgaac tgccatgtgc ccggcgggga    21240
tgccgtccct ggcccttgct gagtgcctct gggacgaggt cagctgagcc tgccatccta    21300
actcagacac catctcactc tccaagtccc ttctcggtga cacgggggc cttgcaccca    21360 cctcccagcc cccacacacc tgagggggtc cccgttcccc taccccgtgg ctccaccacg    21420
ccccacgcat cctacctgag ggacagaggg gactgtgaga tgcccccac aggctggttt    21480 tcctcttttct cccataacag gcccagcaaa ttctcacctc cagaggccag gtctgccccg    21540
tcaggtctta ggaaatacag ccctacttcc atccagcaca ccaacccaag gaagtgcctc    21600
ggagccctgg ggcccgaggg gggcctggcc ttggtctcac ggcggcagct ccacctggag    21660
aggagtgaac tcaagccagg acgccccgtc tccacagcgg aaaccgtgtt gccggctgct    21720
ccctcctggg gactctgggc ctgaggttcc tgtgggagtt gggggataga ctgagtccta    21780
tggaggtgcc cctctcctcc ccgcccagtg gagcttgggg tggggacagg cgaagacagg    21840
gtgagaagca cggggcattc cccctccaca cagcgctgag aaagtaaggg agcatccaga    21900
aaacggtgcc cacttccgcg tcaggcggat atcacgggca ccagctccag gtgaccctag    21960
cccagccaga gaacaaggac caggttgtgc cgcaaagccc gtgtccgctc cctcccgcct    22020
```

```
gggaccactg tggcgagggg aagggagcgt ggtggccctc tcctgactcc tgaggcctga   22080
agtccaagct cccggccctc aggcaggcca gggtctagac accgctgccc caaacacacc   22140
ccccagtccc cgcccgcagg cttcctgcag gatccccccag tgcacctggg ggctgaggag   22200
agtgagcagg gcgcaaagaa gcttcgtcgg gagggcggtc cccacccgcc ttggacccccc   22260
ggggatagtg tcctggggcc tgggctcaga tgcaccctgg gaggaacggt gcgggggctg    22320
tttttttgctc caagaggaca ttgcctcagc agagggctgc cgagctggga ggacccacag   22380
tgcaaggccg cagaaccccc taggaagcct cagagccttc aggttccggg ctgaggctgt    22440
gggcgtggac ccttgtgcaa accccactgg aagaaaaacc ttacagctca ggaggaggag   22500
gggcccccacc cgctcccaga gcccgtaaac gaggggtggt gcccacatga ggcctgggga   22560
agggctgggg ctgggacacc ccttcaccac ccccagatac cccaggcagc ccctccctcc    22620
acagagagac ccactgggcc tgaccctgcc ctgggcacag ggtcgagcca gggacggccc   22680
gtgggagaaa gacggcttca tgggccgctg gccgggccag gtgcgtcctt ccccagttct    22740
aggtggcaaa tggggtgggg ccagagcctt ctggctaggg aagacactgg cctggttggt    22800
gtggcagggg cagcgaagga gggtcaaagg ccactctggc ctggaagatc cccagccacc   22860
tggacggggg tagccaggcc tggtccctgc ccccactctc caagggggtcg gggcagccgg   22920
gcagagccag taagtgtttg ttttcagatg acatttgtaa agaaaaacag cctcccacac   22980
tgcttgaccc tgtgtctgga atgtggggag gcaaacagct gtgcccttcc cagaccctgc    23040
acagccctg gtggggcagg gccctggtgg gagcagggcc cagaggtaca gcctggggag   23100
gcaccggcca ttgtggttgg agcgcggcag ccaggctctg ggctctgttc cgggcctcac    23160
tgtgtcccca gtggggtgcc gccaccaccc cccagcctg ggccccgccg gtcagacacc    23220
cgcagggaca gcttgtcttg gctagctggc tacagcacct cgctggagtc cagcagacac   23280
gcgctcccgt gcgcacgctg cgccccaggc cagccctaac gccgctgctc gggtcaggcc   23340
ccccgcctgc cgtgggctgc tggctgcctt ggcccgcccc agctctctcc gcgcccctgc    23400
ctccagggag ccctcctcga ggactccagc cacccaagct cagcagggcc agcccgagcc   23460
cctgccccac ccagcctgtg tggagggtcc tcagcccccct gatcccccag accctccgg    23520
cagaggctgg gtccctgggg cttggggaaa gccggctcca tggcccctgg cctggatgat    23580
ttcccagagg ccggtcccct gccaagtgcc tggtgaccct tgttcctacc tggctgccca   23640
tggtcctttg tgcgacccccc gcccacagcc caggagctgg gcaggagact ctgattgggt   23700
ggcagcagag ccatcctagg gctgcccctg accctggccc tgaccctgcc ctggagcctc    23760
gtttccaaat cttgcctcat gctttcgcca gaccccgtgtg gccccttccc gaccctggag   23820
tgcccctggg gcttcctgga aaggcctctc ctttgctcac agttgggtgc cggacttcac    23880
cagcattgac cacccgaagg cgcagggaca ccccgcagt ccctctcctg ggggtcccat    23940
caccaactcc ccatgggcgg gatatcagaa gaattctctg cgcaggtgct ccgcccttc    24000
aggcacaggg gagggcggct caggggccaa cggcagacgt tggtgcctgc ccctgcagcg   24060
gggtgcccca tgctgagaca gcacacacgg ggacactcc gggcctcggt ccaccctcca    24120
tgtggcaaat gaggtgcttg gcggggcttc ttaactcttc accctgggct ccccacgggt    24180
cccttcccctt cccccttgggg gccccggccc caggtcccca aggcctagac ctgcctctgc    24240
caccctcaga gcaaggatgc gctgcagagg gagaggggct gcagctcggc cccagagctc    24300
cggcttcctg tctcccagac cacaaatcac taaaggccgt gggtcctggg acattgaagg   24360
cccaggaagc tccttgtgtt gagttaaaca tagcggagca gaggcatgga gctggcattt    24420
```

```
cccacgctta cgaccactgt gctacgggct ggggtggggc tgggaatcag cttcccctgc   24480
gccccgccat cccttgtcca gagggacccg tgggaaggcc aggttgaaga gttaagaagc   24540
cccgccgagc acctcatttg ccacacggag ggcggaccga ggcccggagt gtccctcttg   24600
cgcactgtct cagcatgggg caccccgctg caggggcagg caccaacgtc tgctgctggc   24660
ccctgagcca ccctcccctg tgcctgaagg cccagcactt ccagggctgc ccgagctgag   24720
gacctgtgca gagaactctt ctaccccca cagaggaggc tgagggtcg aggcggctgc     24780
gggagcccca gggggccacc acacagccat gcctgcccct ctcctcggtg ggtgtagaaa   24840
gctcttaaat ggtggaaaaa caagggcatg gccacattgc acaggcacag aaggttccag   24900
aaggagtgaa acaatggcat ggagggagca gagcctgggc cggtgggggc acagggatga   24960
ggccagtgaa ggccacgggt tgggggtgc cctgaagcca acgacccat ccttatcgcc       25020
tgtgtctctc tgcacacagc gtctcgtctg caaagttagc tgagcaaacg ccaggagcca   25080
agggtcgagg caacgatatc cgtggggcca ttcacaccc ctttgcctgc cccatcaaga     25140
cctgctttcc tggttgaaat ccaactcacg atttgccccc ggggcccagc agccctaccc   25200
aatggagcag ctgcacccac agtgcccagc ttcccaggcg acaggggct tggtgagcct     25260
tcctgtcccc actggagcat ggccggagtg attttctgct tctgctgcag atcaccctgg   25320
tgggagcagc tgtaatcgca ttatccccag ttatgcctcc actgggcact ggggtaggga   25380
caggactgcc aggacacgat tccatttacc taacgccagt ggagccctgg gggctctcct   25440
aggtccacgg ggaggggtgg ccatctctct aggcccaggg accccaggac aggggtagaa   25500
aaccacggga gagttaagga gttaaggcca gaaggggcca gtccggccaa gtggggcaaa   25560
gctgtccacc gttgggcagg gcacgactga ggggcggtgt ggggaacagc tgctcatctc   25620
ccccaggccc atgcccgtga tgaactgtgt gactaccccc aggatcagtc aggaagcttg   25680
gcccaggagc ctgtgcagac ctaacagcca gctccagccc cgaggcaggg cagctgtgct   25740
ccagagggct cccggggccg cactgtccct cccaggtgga caccctcgtg gcacgtacgc   25800
ccctgctctc agccctctcc ttcactggat gaagagactc gggacccgca gaggtgggtg   25860
gcgggcagag gaggtggagc tggtctgaga cgcaagacgt ggcctgtgga ttctaggagc   25920
aactggtggc ttccaaggtc ccccaccac tccacacatg ttcccaaacc ccgttttgca     25980
gatgaggatg gcaggctcag cacagggggcc catgtctctg tcaccaggca aggtgggggg   26040
gctctagggc cagaatcgct cccacctcca gccggggatc agaggtctct ggttagcagc   26100
cgaggcgagc gggacacagg ctgagggatg gggacagctg ctcgcccggc acagacaagg   26160
ctccccctccc catgctggag accccggctg cccatcagt cacggcccac ccaggaccat     26220
gcaatcatcc tccacttctc ctaatcctcc tgccagcttc ttcccaagag tccaagcagt   26280
tggatgcatt ttctaaattc tcaggccact gctgtttcct cctcaaattc cttgtccccc   26340
acccgtggcc cctcccagc catgggaaag gactgctgcg gcctcccac aggcctgtgc     26400
acgggtgggg ctgcgtccag gcagctgtga ggtaccgggg acccaggggt aagagccccg   26460
attacagggg cgtcatggga aagtggcgag gggaggccac ccaggccccc accacagcc     26520
ccgctccaca tcctcccctg atctctggcc ctggaaagaa tcagatggga cccccagcag   26580
cagtcacttg agtcccactg ccaccggctg tgctgaggat gcccactggg ccgtgctgtg   26640
gccacctggc ttgcagtgtg ggcaccaagg tatcggccca gattcctacc catcagagca   26700
ccagcacagg gccgagccag tgccacagag cccctgggct gcagcacgtc ctgcacgtcc   26760
cacagaccgg cctgccggga gggagggtg ctgcccaggg ctcggtgccc tcccggaagg     26820
```

```
ggcttcagtg gggctgtttg ccaggtggtg gctctgacgc aggagaggac agatgggcag   26880
agcccgaggg cagccctggc caggtgcgta cagtggtggc tgtgacgccc tctcccacgc   26940
ctgtctctgg gtccaggagg agtgatgatc tccaggctcc agaggactag aacagcagg    27000 caggctcgct gctgataacg gggacttctc cacctggtgg ggagtgatga ggcaagaccg   27060
gatggcaggc cccaggcctc tcctctccag ggacagccat catctcctcg cctgtgcagg   27120
tctcaatcag tcagtgatta acgcaaccag caaccagcac tttattgccg gttgtgaaga   27180
tctggaggac atgcgggtcc ccggggccac agccttcccg catgggtgag cagtaagctg   27240
tgcaattagc cctcaggccg tcatcgccag gccctgcctt tgttcctcca cctgccgccc   27300
gccggaagcc tcccacaacc tggccagcct gctctttctc cccctccact ctgacccctt   27360
cctcctcagg gccctgacat gcagctatct ggcacccagt ttcaatacct ttttctttct   27420
tttttttttt ttgagacaga gtttcactct ggttgcccag gctggagtgc aatggctcga   27480
tttcggctca ccgcaacctc cgcctcctgg gtccaagtga ttctcctgcc tcagcctctg   27540
agaagctggg attacagaca tgcgccacta cgcccagcta gttttgtatt ttttgtagag   27600
acacggtttc accatgttgg tcaggctggt cttgaactcc tgacctctgg tgatccaccc   27660
acctcggcct cccaaagtgc tgagattaca ggtatgagcc accgagccgg gacttctttt   27720 ctttttcтттт tcttttttcc agccctcaac tatccgtttc attaaaaaat tcagaattct   27780
ctcccctgcc tgccaggatg ggacccaaaa ctcgggcaat aggcctgccc gagttgtggc   27840
cctgggcctg tccccgacaa gtcaccctac gttttccatt ccaccatcct ctctctgcac   27900
ctcaagcacc gtgaaccctc tcccacctgc ctgacctcgc cgtctccaaa ggagaacctt   27960
tcttgtgtca tcccgccctc tctaggcccg ccgtctgcct gggggctgcc ctggtggctg   28020
tgctgtgtct cccactgctg tgcgcacggt gctgcctgct ctttgcctca gaggcactgg   28080
agcccatgtg ctcggggggg tgtggccttc gaacactgtg agtccccaca tcttgcctcc   28140
agaggccaca gctggcctgg gccaagcctg gccacttcc tctgcagtga ccaagagcag    28200
ggctgcctcg agggtttcgg ggcaggagag agggaacaaa tctcctggag gcagatgggg   28260
gccacaggga ggctggaggc ctcgaacccc tcccagagag ccagtggagg gatgctgcct   28320
ggcagatggg agatggcagg cgggtgctcc aggggctcct ccctccttgt agcaccttgg   28380
acatgttttg ttttattatg gtgaaaatat gtaacaaaac tagccattat agccattgag   28440
ccactgagcc actgagccac ggagccacgg agccatggag cacacacatc agtggcactc   28500
agtccattct cactgctgcg cagccatcgc caccatccac ctcagacctc ctccctcttc   28560
ccaaactgaa gctccctgaa ggtgcccagc ctccttgcca gtagatgaga tggggaggca   28620
gccctgctcg accaaggagg cagaagtctt gattgttctc cctacagtcc cacgggaagc   28680
acctgcagca gggccctggc tggacagacg gccacaaggg gtgtggtgca gtgatcgggt   28740
gccctggcct gggcaggaga gtggcgccct tggcctgccc agcccctgcc tgcggccgc    28800 ctgacagcca aggggagctt caccttccag cctctggctg tcattagctg ctcccggtgg   28860
gaggtgggac cggcagggga agctcagtcc cacagccagt gaggatccag gctcaagcgg   28920
aaccacctgg acctcattat tcttaagtgg tccagtctga agtttggga agaggggagg    28980 aaaaaactgc caatcccag gctggggag ccccaccccc tcttcaagcc agcactgaag     29040
ccctgggggt ttcagccaca atggagagct aaaccgggcc caccccaggg cccaggaggg   29100
gcatctgtag aggggttcagc cccaggagga cttggaggtc aggcaagcca acgggagttc   29160
agagcttagg aggggtgaga ggtcagactc tggtcctttc tcatcacctg gggtccgtct   29220
```

-continued

```
gtccttccag gtcacctggg ctgtctacag tcaaggccag tctgacaggt gggatggtgc    29280
ttcccagcaa ccccaccctg aggagaaccc tgctgcctct ccctgctctc cacccccagc    29340
acaggccccg ggaagcctcc agctgatgac gacaccagga tggtgctgag tggaccctgg    29400
ggccagcatc acaaggcacc caggacccca gaccacccag ccacacccca ggctacgagg    29460 aggggggcgct ccggcgaggc tggggtgcct tcaaggtgca tcctagcaac atcctccacc   29520
tgcaggaggg acactcggtc acagcttggg gaggatgtgc tcagacggca taggaaggat    29580
ttgctcagac cccatgggga ggatttgctc agaccccgtg gggaggactt gctcagaccc    29640
catggggagg acttgctcag aacccatggg aggacatgc tcagacccg tggggaggac      29700 atagaccccg tggggaggac ttgctcagac cccgtgggga ggacatgctc agaccccatg    29760
gggaggactt gctcagaccc cgtggagagg acatgctcag accccgtggg gaggacatga    29820
tcagaccccg tggggaggac ttgctcagac cccgtgggga ggacatgctc agaccccgtg    29880
gggaggactt gctcagacc ccgtggggag gacttgctca gaccctgtgg ggaggacatg     29940
ctcagaaccc atggggagga cttgctcaac ggcataggaa ggatttgctc agaccccatg    30000
gggaggattt gctcagaccc cgtggggagg atttgctcag accccgtggg gaggacatgc    30060
tcagaccccg tggggaggat tgctcaggc cccatgggga ggacttgctc agaccccgtg     30120
gggaggattt gctcagaccc cgtggggagg acatgctcag accccgtggg gaggatttgc    30180
tcagaccccg tggggaggac ttgctcagac cccgtgggga ggatttgctc agaccccagg    30240
caggcatcat gaatgcgccc agcccggacc ccagactggt agctcctacc acacgcggag    30300
cagcagaggc tggcaagagg gactcaggac ttgggctggg gacagagggc cctgcacagc    30360
tctggggtcc tgacccaatc ctgcatttcc atagagagct gcctgggcac ccatgctgag    30420
ggtccctgca cccctggtg tatcggagac ccttcccca cccctatcc cccgccactg       30480 agacacagga atgtacagga tggctgtgag ggcagaggca ggcccagggc gcagcaggca    30540
gggctgggcg gggctgggga tctgcaggag gttggccctg gagatgggac atgtctggac    30600
cctcggtgtc atcacctcta tgttttgacc actgagcaaa attacactaa atgaagcaca    30660
aattagccaa ggggacagtc gactctgtcc tttcttctta atccctctgg ctcagggttt    30720
cccagcctgg acagcctgtc cgaggggaag gctgcccaag ggacacggg catcggtccg      30780 gggacattca ggcagtgacc aatccctggc caccctggtg tgtgcccggc aatgtgggcc    30840
ttttcccaga cagccagtgg gggagcggct gctgtgggtc cctgagtctt agccagatgg    30900
tcaaggatag gacaatgatg gagacccgca tgcggccgca tccatgggta aggaggcgg     30960 aacggaggac agctctgcca tcccctcagc cagccatgaa aagcaaccct ttcccctaag    31020
gccccagcac caccttggag gccaccatgg gctggagccc agcacagcca ccatcgcatc    31080
ttggctgtcc agctcaggac ggccagttcc aaggcgtcca ggctggagct ctggggcgg     31140 aagagcacaa gctcctgaag agcctctggt ccagccctgg cagcggaggg ccaggtgaga    31200
gcctgttgag ggctctgagg actccaggag ggactggctg aggacaccgg tggggtaat     31260 acctcccct ccaatggccg ctcgcaggag gcaattccca gagcccgct ccatgggcca      31320 ccaggtaccc agagcctcat ttagaaatgg ccatgcctcc ccacaggccc ccgctgggat    31380
cctggtgctt caaatgtcct gctgtggtcc caggaggag caaaaccccc tcccagtcag     31440
gaagcatcct caaccgcatc taattccaga tgctacctcc caccttggct ttccaggaga    31500
cggagaacgg agccggcccc tctccaaggc cccgaggccc ggcagggcac ccctcggagc    31560
agataagctc accctgctc ccaggacaag caagctcctg ctgaggctct gctactgcta     31620
```

```
attggccctt gggataagca gacctgtcca ggaaagaacc ctctccctga tctcctggcc    31680
ccagccccat ccggccggga gttctgactt aagcaaataa tcagtccagg gaattggagg    31740
ctcaacagaa tcgtcctcca ggaatctggt cttcgttcct ccaccctcct cctcccgtct    31800
ccgcccgggg tcttgagatc aacagcaagg ttttgcactc gtagggcttc cccggagaca    31860
ccctccagcc tcaacccaga ggagatgggt gcctgggccg tgaccoctca cacaagagga    31920 ccaagcccag agaggagacg ggaagccatg cgcccggcca gctggggtct gcgatggact    31980
cagtggggtc cagccctcct cactccaagg ggagctggga gccgacccgg tgagggaggg    32040
catcctggga aagtgacagg aatcaggaa tggccctggg gctccggacc tcctctgatg     32100
gagtcattca aggcccttgg cagagctggg catcctctgg ccccaggga ataaggtccc      32160 ctcactccac cacagaacag catctgggta cctacctgtt ggccatgggc agagcaaaac    32220
tctctcctgg accccagtgc ccagagccct ggccttggga gggagctgtg catcctcagg    32280 agccccccg ggctgccccc caccaccctg caggcagctc accctcccac cccaccagct     32340
gcaggtgcgg acacgtgtct tctccttccc caaatgctcg ttctgcacct gcttcgggag    32400
ggcagtcctg cctgctcaca gcccagccct gcccgaactc ctggccatgt gtggaaacac    32460 acggcgtta gaacatggca tcccggttcc cttctatgtt caggaagacg acacccatct     32520
ggctgagggg atggcagagc ccctctcccc acagccccct ctgcagtgca gctctccttt    32580
cctctccccg catgcctctt cccgagggca gccccttctc tccatcagga tcgcatgcct    32640
cttctcgagg gcggcccctt ctctccatca ggatcaccct tcctgggctc cggggtgcaa    32700
cgggcgggcg ctgtttcccc caagccctcc cttcctccct cggggtgggg ccctttcctc    32760
caggctcttc tccgtctcct ggtctctgcc atctcccaaa acccattcta tttctccaca    32820
tgtctacctc gtcccccatc cgtctccatt ctcctagtct cccgcctgcc agcccggccc    32880
tggcaccagc cacttggcag cctcctcctc ctcctcccag aaccttctct ttccttcctg    32940
gtcccatctc aaactgcagc aagctggtcg aaaggtgaga ccaggctggg aggagctgtg    33000
ggccacggag atggtggccg ggggaggtat gggaggtggg agggcaggcg ggccaggtgg    33060
ggagcagggc atcttgccat gggaagggct ggaggaaaca ccgcatccag ggatggccag    33120
agctcgcctg gagcccctga aggtcttgct tttagagccg ggtggggctg ctgtgtggcc    33180
aagccgggcg agtggcccca tcccgggtcc tgggctcctg gcgtctgccc tggagcccac    33240
catgttgcag tactgtgtgg ccgtccattg ctgctctctt cactgtatga ccgggggttc    33300
cctctgtgcc cctcaaagcc ccaacttgcc tggactttgg gtctgcagct ggcgcatggg    33360
aatcttccca catggcagcg tagggtgact atggagccga ccaaggctgc caaggtctta    33420
cttgagtaga agacttccat cctgagcgat cctgttggcc ggtcctccgg atccagcctt    33480
cctgggaatg cggccaccca caggactcca agcgggtctg gggtctctgg tcccccaggt    33540
tgaccacccc ttgctgcagc tgctccggaa acagaggggtg ctgccctggc cattttgctc    33600
cttgctgggt gtctgggagg gctgcgaggg gaggaagaag ggcagggaga ggtgagagac    33660 ccagagaag ggggaaggag tctcaaagga ggggagggac ggccggccag cactgtggcg     33720
cagtgtgcag gagggaaca tggcggtgcc cggcacgagg tggggtgcgg ggcagccctg      33780
gagccctggc tgcctctccc agcagtgggt ccggcactag ctagccagct gagcttgctg    33840
tgtttggagt ctgcagaaag tgctgccccg ccaagcccca caggccaagc caggcccgag    33900
ggacaggaag gagcatgggg ccttcactca ctgcccagcc cggggcacgg ccggcccatc    33960
tcccatttcc agggccatcc ggggaacggg cacgccccgg atacttactg ccctgtcact    34020
```

```
ggaggttagc atcctccctc gtccggtgcc ctgcccaggt ggctgttacc tcccctacct    34080
cctccaagac cctgagcagg gggagaaaga aagtggacag aggcacccga cctcctgacc    34140
tgagtgtggt cccgctttg ttccccttc ctctgccccc agttctcact gcgaaggagg      34200
agagggctca cctggggtgg ccccacgtgc ctgccagcct tggtccaaga ctgcagagaa    34260
gggtccctga ggaggtgggg agaacccaga ggcagatcct gagggtcttc cctgaaagag    34320
gagggctggt gggcagcagg aagatccggg attgtgccct cagctgccct ctctgtcctg    34380
acgtgtcacc cgctaagggt catgggccaa ggagggaacg ggcaatgtct gggagccata    34440
gagttgggat ggcccggcca ggctgggtgt ggggtctgtt ggggatccca ggtgagggga    34500
aggaattggg agtggacctg gcccgaggc aggttgggtg gctggtgcaa ggcagagggc     34560
tggcccgggg ggcattctgt cctggttcct ctgtcccctc acccagttcg tgagcatccc    34620
tcgtggagca ggccccaggg agatcacggg cggcgggtgg gcagatggag tgcaatatcc    34680
cccaaggaaa gtgtgttgtg agtggtgga gggcagggcc ggagaggccc cagctgtgga     34740
gcaggacgct ggagggctca gggcagccga gccagggccc ggggcagccg caaagtggca    34800
ctgtgttctt ttgggccgga ccagagccca ggcagtgtca ggaggtggat ggtgtggaag    34860
agagaggagt tccaggggcg cactggggg ccctctgtgt ggctggaagg tggagggcg      34920
ctgggtggaa gggctggctt cgggctggcg cttgggcta aggcaggctt gcaggggctg     34980
gctcctgaac ccacgcatgg cgagaagtat gggctggagc ggccacagca ttggggaaag    35040
acagatggga gggctggaca ggaagcaggg ctgtggccag gccggggccc cggggaggaca   35100
gggacgagtg gtggacgtga gggtgcagag gagcaaagtc caggacttgg cccggatcgg    35160
gatgctcagg aggctgggga tgctcggagg aaagcaatgg gggagcccgg ctgcctgccc    35220
caccctgcc accctcagct ccttctgccc gccaggactc ccaggctcca tcaggtgccg     35280
cagcaccctg gctgcgacat aacgaggtgg gacagggtca gcaaggtgac ttctcgtgcc    35340
ccagtgtttg caaatcccca aaatgaccca acagacaagc tcgaggctgg attttccaag    35400
agggcccctt caagtaccaa aggacacaaa gagcaggccc ttctgagtct gcggcccaca    35460
gatggcagca cgggccccgg accccaggac caccttgggc acagagcggc tgggcccagg    35520
aggctggcct ctcccgggga tcccacggct ggcctgcggg gctgcagcaa acacgtgcag    35580
ggctttccag agccccgcac agaacaaaga acaaaatggg gagagcaggg cctgggctga    35640
acggaccacg ggcgggtggg cggaggggca cagcggcatg gcacccactg ccaggccgag    35700
ggcagctgca gggggctggg ctggagcaga cccggggtgg gggtggggc tggaggaggc     35760
tctcacggcc ggaatcaata actcacactg ggggagggcg ggagacgttt gtggcggagc    35820
ggggaggggg tgccggacag ggtgtccctc caccccaag ttcaaagttt tatggcgagc     35880
aggcttgact tcctcccgcg tccctcctct ccaggtgtta tttgaaaaaa atacttttca    35940
aactacatgc tgaaaacttc agcatgaaaa tttaatgtca gaaactctgt aatctctttc    36000
ccagagataa gacccagccc ctcgaggagg ggcgaactcg atccctctaa cacagaaagc    36060
agacgccagg ccgggaaggc aggggcctgg cggcctcgct ggggaggct caggctcacg     36120
ctccctccct ccctcccacc cgcggctggg aggggtgac tgagagaggc cctgcagggc     36180
tggagctgca gggctgggc gaggggtccg gcaggagggg ccgtcctagt gcagcctgca     36240
ggcttcgggc cttcggaag cacatcctgc cgctctcccg cgtgcacccc gctccccgga    36300
acttggagtg ggtgccgctg ctgccaaggc tcgggtttcc atgacggctg aggccctgg    36360
ccctctcact cagaccctaa cttaggcctc gctgagggct caggttgtgg acagctaagc    36420
```

```
tggggaagga caacgtggcc accaccgccc acggcctttc tgaccggcag cgccgccctg    36480
ggttgggtgg cggggcgtc  ctgcacacac gactcctgag gtcaagcctg ggtgtggggg    36540
tcttggactc tgagctgcca ggcccgccgg gtcctggcct cagggagagg ggaacggagc    36600
tgccacacac ccggctcttg actcgatttc tctgtggggg acagacataa cttctccaag    36660
ctgtttccaa cagcccccac cctgaagacg gcctccacct cagacatcag acaacgcccc    36720
gagcccccc  tgcccagggc cgggagggca ggctgcccgg aaggagggtg gggctgcccg    36780
ggggctgggt gtgcgctcca gacctgtgtt ctgggactgc attccggggg aggggtggt    36840
gggaaggcgc catgtggagc aaaccggctg ggctgggggc aggaggcccc ccaagcgggg    36900
agagggaggc gtccgaccga ccgcactgct ctgctgcccc caccaggcag gccgaggccg    36960
gcatccccgg agaccgggac ctggtggccc agcccagcac tcctgaatga gcctgaggcc    37020
cccgtgtcct gagaggcagg gggctccctc ctttgtagcg gaaggagaca gaggcctcct    37080
aaaggggccg gacgcctgcc caaggcgcta gtcgcctgga agctcccaga atgtgggtgt    37140
gggagaggcc aaactgcttt ctccccaaac cccaaaatcc tgggtgaccc tgaacccggg    37200
cctgggcact tggccctgtc tgcccaagcc ccctaccggc cccccatgt  gctttgcgtg    37260
gtccgagccc agcgggtggg gcagggctgg cttgaggctg ccgagagggt ttctccccaa    37320
ccgtcctgcc ccctccaggg gacatgcaga gccagactgg tctgttgtcc tgtgtttgcc    37380
tgcctctccc ggtgttgccg tggtgatgac acaccaggca tggctgggag gggtcatacc    37440
tcaggcagac caagagtcct gcgtgtccac cacagacggc accccctcag gatgcccacg    37500
ccctggcccc cggctcccag gccttgtcga gaatgttcca tgagcctgac ggacaggcac    37560
gaggtccagc gtgtgaggcc caggccgctg ctccggcgcc tgcccttgca tccccacagc    37620
accccgccca gccaccctat ctgtcctcgg gtcccccca  gccgtctcag gtccaggctg    37680
ctgggtgtga aagcgccct  gggtttctgc tgtgtccctg cccctgacg  aggagcgctt    37740
ctcttcctgc acccacagcc ccacacagcc cctccacgcc ccagggtccc ccagccaacc    37800
cagcgtccta tctgctgctt gcagctgagc ctgcggcggg ggaccccagg caaatatgag    37860
gaagcctggg cagaaggtgg cccctgcaga agctgctgcc cacgtgcccc cgccccatgc    37920
tgccaggaga ggctcggacc tcaacaactt gggagtggca gaaatggtct ctgcatgacc    37980
agtgcggccc cttcttagcc ccttcctggg gcttccggag ggcctagcag cttccctggc    38040
tgggggctga ggggcctccg ggcggcgact cttggaaaag cctgaggtca gaagagttca    38100
gaaacgccgc tgctggctgg gtcctcttga ctgatgtgga caactgtgtc ccatctccct    38160
gagctatttc tgttttcgca ggagtcaggg gagggctgga actccggctt cccggcatcc    38220
cggcgggcaa ccagatacc  tcagataaag ggcattcctg gaggccttca tcacgctccc    38280
cgggcagctg ctggcccctc accctgcaca gtgggcacg  tcctccctga gccccgaggg    38340
aggctcggaa cacatagttt ccctgttatg taccagctga ggggcccggt ggatttagct    38400
ggggtgaggc ccaggggccc aggcgagcag gggatgttct cgtagggagg acagggctga    38460
gatgggaaga gcagctggtc ctaagcccca caggcccccc ccacagggtc ccctcagggc    38520
cccgagcctg ggttttattt tgggaggcac cttctagagt gtaagctgcc tcatcccgcg    38580
ggcacgcgtg gggtcgccca ggcctaggg  gatccttcag ccggctgtcc agctccggga    38640
ctctgggttc ccgggaaccc ttggggctg  atgttctgag catgtttgct ccgcagtgtt    38700
ctcagccaca cctgcaccct agcaggatgc cagagggctt ttcccagact tcagagctga    38760
ggcccgggcc tggcgggcgc ccctcctcc  agcaggacgg gaaccaacca ttcactcaag    38820
```

-continued

```
ccacgagcac cccacgggct gccctgaaga gctgttggga ggagagggtc catgatccca    38880
ggctctgaag acctctgtgc ccagcagcgg ggcctctgga gggtgaggag ggatgcgtat    38940
caggagcagt ccattgccgg ctggtggggt ttgttttgtt aaaccgaaag aaaaacagca    39000
gcagcagcac agagcccngg ggcagctgac ctcctgaagc caggcagggt gcctgggcag    39060
ggccccaaaa ccacagagga gccccagcca gccctctggg gagcagggtc aggcaccccg    39120
acagagggtg accaggacac acgacccggc ggccctgcag ccccccagca cctcctcact    39180
ggggaccagc ctgtcggcag gaggcagccc tgggggtcgg ggacacagtc ccaaggaagg    39240
ctaggacctg gaacgctcct taaggggtg agacacccct gggggcaga gctaggccct     39300
gaccagggtg gggactgcgg aggagctgag ctggctccaa tcggtgcatg gctggctgtc    39360
taggggcagc acagagggag gtcccatccc aggccagcag tggcaatgcc atctctgaaa    39420
aacggtccgt gccatgaggc ctgagcctcc ggtgcccttg cctggcatgc tctgccacac    39480
cgtggccgcg tgagggacag acagcgcggg acagaatccc acctggcagg gaggtggcag    39540
gcttgccatg tgccagcagg caccggggga ggaggggctg ggtatcgggg gcggggaccc    39600
tcagggcgaa gctcgatgtt aggcgggctt cttctggagg cccgtgtctc ctgggcaagc    39660
attatcatct ccacgtttta ttttattata ttattattta tgtatttatt gaaacagagt    39720
cttgctctgt cacccagggt ggtgtgcagt ggtgcaacct ccaccttcca ggttcaagtg    39780
attctcctac ctcagcctcc cgagtagctg ggattacagg cgcccaccac cacacctggc    39840
taattttgt attttagta gagacagggt ttctccatgt tggccaggct ggtctcgaac      39900
tcttggactc aagtgatcca cccacctcag cctcccaaag tgctgggatt acaggcatga    39960
gccactgcat ctggcctcgt ctccacattt tagacaaatc aagacaaagt gacagccagg    40020
ggcctcaggc ttgcaaggca gcagctcaaa gtggaaaccc ggactcctgg cccctcaccc    40080
aggccgcaca cccacagcca ggcctccctc ccagaagccg ccaccaggcc tgctccgggg    40140
ccccagcttc ctgtgctccc ggtccaggcg gtggccattg tctgccagcc attaggaacc    40200
agctggggga agtgccatgc cccagcccct gggcagccca tgtgtccctc ctacacccgc    40260
gggcagggcc ctcgagtccc aggtcccagt ggccagccat cggtcctctc actaaccgca    40320
ggatggccac tgaaggccag aagggtgggg gccttgggg ctacccgaaa atctctccca     40380
ccatggccca ggcccatggg cgttctgtgg ctccagcctg tggctcgggg tgggcggttg    40440
ggggctggg ttttctgacc ccggtggtgg tgaatgaaca gcagagcccc atctacgccc     40500
ccggcctgcc ggctcgctgg ccttcctaat gagcgtgtgt ttccagagcc ctttgatc     40558
```